US012767665B2

(12) United States Patent
Ying et al.

(10) Patent No.: US 12,767,665 B2
(45) Date of Patent: Oct. 20, 2026

(54) BIOTIN DERIVATIVES

(71) Applicant: LIFE TECHNOLOGIES CORPORATION, Carlsbad, CA (US)

(72) Inventors: Lai-Qiang Ying, North Potomac, MD (US); Stephen Yue, Eugene, OR (US); Bruce Branchaud, Eugene, OR (US); Yu-Zhong Zhang, Eugene, OR (US)

(73) Assignee: Life Technologies Corporation, Carlsbad, CA (US)

( * ) Notice: Subject to any disclaimer, the term of this patent is extended or adjusted under 35 U.S.C. 154(b) by 223 days.

(21) Appl. No.: 18/349,609

(22) Filed: Jul. 10, 2023

(65) Prior Publication Data

US 2024/0010657 A1 Jan. 11, 2024

Related U.S. Application Data

(60) Continuation of application No. 16/366,908, filed on Mar. 27, 2019, now Pat. No. 11,731,982, which is a division of application No. 15/390,820, filed on Dec. 27, 2016, now abandoned, which is a division of application No. 13/881,518, filed as application No. PCT/US2011/058455 on Oct. 28, 2011, now Pat. No. 9,567,346.

(60) Provisional application No. 61/510,949, filed on Jul. 22, 2011, provisional application No. 61/501,500, filed on Jun. 27, 2011, provisional application No. 61/495,070, filed on Jun. 9, 2011, provisional application No. 61/408,210, filed on Oct. 29, 2010.

(51) Int. Cl.

| | |
|---|---|
| ***G01N 33/58*** | (2006.01) |
| ***B01D 15/38*** | (2006.01) |
| ***C07D 403/12*** | (2006.01) |
| ***C07D 495/04*** | (2006.01) |
| ***C07K 1/13*** | (2006.01) |
| ***C07K 1/22*** | (2006.01) |
| ***C07K 16/00*** | (2006.01) |
| ***C07K 16/42*** | (2006.01) |
| ***C08B 37/00*** | (2006.01) |
| ***C09B 11/24*** | (2006.01) |
| ***C09K 11/06*** | (2006.01) |
| ***C12N 5/0783*** | (2010.01) |
| ***G01N 33/53*** | (2006.01) |
| ***G01N 33/532*** | (2006.01) |
| ***G01N 33/533*** | (2006.01) |
| ***G01N 33/543*** | (2006.01) |
| ***G01N 33/554*** | (2006.01) |
| ***G01N 33/569*** | (2006.01) |
| ***G01N 33/68*** | (2006.01) |
| *A61K 39/00* | (2006.01) |

(52) U.S. Cl.

CPC ....... *C07D 495/04* (2013.01); *B01D 15/3823* (2013.01); *C07D 403/12* (2013.01); *C07K 1/13* (2013.01); *C07K 1/22* (2013.01); *C07K 16/00* (2013.01); *C07K 16/42* (2013.01); *C08B 37/00* (2013.01); *C09B 11/24* (2013.01); *C09K 11/06* (2013.01); *C12N 5/0636* (2013.01); *C12N 5/0637* (2013.01); *C12N 5/0638* (2013.01); *G01N 33/53* (2013.01); *G01N 33/532* (2013.01); *G01N 33/533* (2013.01); *G01N 33/54353* (2013.01); *G01N 33/554* (2013.01); *G01N 33/569* (2013.01); *G01N 33/58* (2013.01); *G01N 33/582* (2013.01); *G01N 33/6803* (2013.01); *A61K 2039/625* (2013.01); *C07B 2200/11* (2013.01); *C07K 2317/20* (2013.01); *C07K 2317/92* (2013.01); *C09K 2211/1007* (2013.01); *C09K 2211/1088* (2013.01)

(58) Field of Classification Search

CPC ................ C07D 495/04; C07D 403/12; B01D 15/3823; C07K 1/13; C07K 1/22; C07K 16/00; C07K 16/42; C07K 2317/20; C07K 2317/92; C08B 37/00; C09B 11/24; C09K 11/06; C09K 2211/1007; C09K 2211/1088; C12N 5/0636; C12N 5/0637; C12N 5/0638; G01N 33/53; G01N 33/532; G01N 33/533; G01N 33/54353; G01N 33/554; G01N 33/569; G01N 33/58; G01N 33/582; G01N 33/6803; A61K 2039/625; C07B 2200/11

See application file for complete search history.

(56) References Cited

U.S. PATENT DOCUMENTS

| | | | |
|---|---|---|---|
| 3,949,064 | A | 4/1976 | Bornstein et al. |
| 4,529,587 | A | 7/1985 | Green |
| 4,584,191 | A | 4/1986 | Hostettler et al. |
| 6,525,203 | B1 | 2/2003 | Tino |
| 7,141,676 | B1 | 11/2006 | Wilbur et al. |
| 9,567,346 | B2 | 2/2017 | Ying et al. |
| 2005/0101485 | A1 | 5/2005 | Hoffman et al. |
| 2006/0051811 | A1 | 3/2006 | Cotton |

(Continued)

FOREIGN PATENT DOCUMENTS

| | | | |
|---|---|---|---|
| EP | 0094776 | A2 | 11/1983 |
| WO | WO-2009042544 | A1 | 4/2009 |

OTHER PUBLICATIONS

Sachon et al "Analogs of Substance P modified at the C-terminus which are both agonist and antagonist of the NK-1 receptor depending on the second messenger pathway" J. Peptide Res. vol. 59 2002 pp. 232-240. (Year: 2002).*

(Continued)

*Primary Examiner* — Catherine S Hibbert

(57) ABSTRACT

Biotin derivatives, methods of using the biotin derivatives and kits comprising the biotin derivatives.

15 Claims, 9 Drawing Sheets

(56) References Cited

U.S. PATENT DOCUMENTS

| | | | |
|---|---|---|---|
| 2006/0178507 A1 | 8/2006 | Berry et al. |
| 2008/0076909 A1 | 3/2008 | Schroeder |
| 2008/0255004 A1 | 10/2008 | Neurauter et al. |
| 2015/0072396 A1 | 3/2015 | Gee et al. |

OTHER PUBLICATIONS

Hirsch et al "Easily reversible desthiobiotin binding to streptavidin, avidin, and other biotin-binding proteins: uses for protein labeling, detection, and isolation" Analytical Biochemistry vol. 308 2002 pp. 343-357. (Year: 2002).*
Allert_et_al_2003 (Year: 2003).*
Slavoff_et_al_2008 (Year: 2008).*
Bodanszky, M. , "Synthesis of Biocytin-Containing Peptides", Journal of the American Chemical Society. 99(1 ), 1977, 235-239.
Carroll S., et al., "ACSD Labelling and Magnetic Cell Separation: a Rapid Method of Separating Antibody Secreting Cells from Non-Secreting Cells," Journal of Immunological Methods, 2005, vol. 296, pp. 171-178.
Chemical Abstracts Registry No. 258842-82-9, indexed in the Registry file on STN CAS Online Mar. 9, 2000.
Colinas R.J., et al., "Cell Separation Based on the Reversible Interaction between Calmodulin and a Calmodulin-Binding Peptide," Journal of Immunological Methods, 1998, vol. 212, pp. 69-78.
EP 11837225.9, "European Search Report", 13 pgs, Jul. 15, 2014.
Field, "Synthesis of 3'-N'Methylbiotin" Journal of Organic Chemistry (1978), 43(6), pp. 1084-1085.
Finn, F. et al., "Trifunctional Reagents for Derivatizing Sulfhydryl Groups", Bioorganic Chemistry. vol. 23, 1995, 152-168.
Flaster et al., CA 96:122496, 1982.
Flaster, H. et al., "Syntheses and Spectral Properties of 2-Thiobiotin and Biotin Derivatives", Journal of Heterocyclic Chemistry. vol. 18 (7), Nov. 1981, 1425-1436.
Griffiths, A. et al., "Optical sorting method applied to in vitro evolution", PCT International Application 13/881.518. Accession No. 2000:475784 Document No. 133:100420, 2000, 7 Pages.
Hirsch , et al., "Easily reversible desthiobiotin binding to streptavidin, avidin, and other biotin-binding proteins: uses for protein labeling, detection, and isolation", Analytical Biochemistry, vol. 308, No. 2002, 343-357.
Kumar, P. et al., "Base-Labile Group Protected Biotinphosphoramidite Reagents for Solid Phase Biotinylation of Oligonucleotides", Nucleosides & Nucleotides 15(7&8), 1263-1273, 1996.
Lavielle, S. et al., "A Total Synthesis of Biotin Based on the Stereoselective Alkylation of Sulfoxides", Journal of the American Chemical Society, 100 (5), 1978, 1558-1563.
Lowe Commentary entitled "Not AlphaFold's Fault," 2022, 6 pages.
McCormick, D. B. , "Accession No. 1970:74989", Document No. 72:74989, 1969, 1 Page.
McCormick, D. B. , "Chemical Syntheses and Biocytinase Specificity for Sulfoxides and Sulfone of d-biocytin (34246)", Proc. Soc. Exp. Bioi. Med., vol. 132, No. 2, Nov. 1969, 502-504.
Miyamoto, S. et al., "Absolute and Relative Binding Free Energy Calculations of the Interaction of Biotin and its Analogs With Streptavidin Using Molecular Dynamics/Free Energy Perturbation Approaches", Proteins: Structure, Function, and Genetics, vol. 16, 1993, pp. 226-245.
Ogita, T. et al., "On the Intermediacy of Carboxyphosphate in Biotin-Dependent Carboxylations", Biochemistry. vol. 27, 1988, 8028-8033.
"PCT/US2011/058455", International Search Report and Written Opinion mailed, Apr. 3, 2012.
Pubchem, , "CID 1 0448239", National Center for Biotechnology Information, http://pubchem.ncbi.nlm.nih.gov/summary/summary.cgi?cid-1 0448239, Oct. 25, 2006, 1-9.
Pubchem, , "Compound Summary for CID 1 0335693", National Center for Biotechnology Information http://pubchem.ncbi.nlm.nih.gov/compound/1 0335693, Oct. 25, 2006, 1-9.
Pubchem, , "Compound Summary for CID 23264086", National Center for Biotechnology Information, http :!/pubchem.ncbi.nlm.nih.gov/compound/23264086, Dec. 5, 2007, 1-11.
Pubchem, , "Compound Summary for CID 25133576", National Center for Biotechnology Information, http://pubchem.ncbi.nlm.nih.gov/compound/25133576, Jan. 19, 2009, 1-10.
Pubchem, , "Compound Summary for CID 254911 02", National Center for Biotechnology Information, http://pubchem.ncbi.nlm.nih.gov/compound/254911 02, May 27, 2009, 1-11.
Pubchem, , "Compound Summary for CID 83863", National Center for Biotechnology Information http://pubchem.ncbi.nlm.nih.gov/compound/83863#section= Top, Jul. 19, 2005, 1-14.
Sachon, E. et al., "Accession No. 2003:411669", Document No. 139:160249 2003, 1-7.
Sachon, E. et al., "Met174 side chain is the site of photoinsertion of a substance P competitive peptide antagonist photoreactive in position 8", FEBS Letters, vol. 544, May 6, 2003, 45-49.
Sachon et al. ('Analogs of Substance P modified at the C-terminus which are both agonist and antagonist of the N K-1 receptordepending on the second messenger pathway' J. Peptide Res. v59 2002 pp. 232-240) (Year: 2002).
Slavoff, S. et al., "Expanding the Substrate Tolerance of Biotin Ligase through Exploration of Enzymes from Diverse Species", J. Am Chem. Soc., vol. 130, Jan. 3, 2008, 1160-1162.
Wang, J. et al., "Ranking Ligand Binding Affinities With Avidin: A Molecular Dynamics- Based Interaction Energy Study", Proteins: Structure, Function, and Genetics, vol. 34, 1999, pp. 69-81.
Ying L., et al., "Design of a Reversible Biotin Analog and Applications in Protein Labeling, Detection, and Isolation," Chemical Communications, 2011, vol. 47, pp. 8593-8595.

* cited by examiner

BIOTIN DERIVATIVES

CROSS-REFERENCE TO RELATED APPLICATIONS

This application is a Continuation of U.S. application Ser. No. 16/366,908, filed Mar. 27, 2019, which is a Divisional of U.S. application Ser. No. 15/390,820, filed Dec. 27, 2016, which is a Divisional of U.S. application Ser. No. 13/881,518, filed Sep. 26, 2013 (now U.S. Pat. No. 9,567,346, issued Feb. 14, 2017), which is a U.S. National Stage Application of PCT Application Serial No. PCT/US2011/058455, filed Oct. 28, 2011, which claims the benefit of priority to U.S. Provisional Application Nos. 61/408,210, filed Oct. 29, 2010, 61/495,070, filed Jun. 9, 2011, 61/501,500, filed Jun. 27, 2011, and 61/510,949, filed Jul. 22, 2011, which disclosures are herein incorporated by reference in their entirety.

BACKGROUND

The interaction between biotin and avidin or streptavidin is considered to be practically irreversible. Biotin has a affinity constant, or $K_D$, for avidin of about $10^{-15}$ M. While the interaction provides an excellent means for capturing biotin-containing entities, releasing those entities once captured requires very harsh conditions, such as a strong acid, detergent, and/or high temperature. Such conditions include, for example, boiling in high salt; formamide and EDTA heated to 94° C.; 6 M guanidine, pH 1.5; and heating to at least 65° C. in the presence of salt, SDS, and EDTA. Such conditions are generally not suitable for purification of proteins or viable cells or viruses.

SUMMARY

The inventors have developed biotin derivatives that have reduced affinity for streptavidin. Thus, in some embodiments, the biotin derivatives can be separated from streptavidin under less harsh conditions than are required for biotin. Accordingly, in some embodiments, the biotin derivatives are better suited for applications in which it would be desirable to dissociate the biotin derivative from streptavidin under less harsh conditions, such as to maintain the structural integrity and/or viability of the moiety attached to the biotin derivative.

In some embodiments, biotin derivatives are provided. In some embodiments, a biotin derivative is provided that has the formula:

(I)

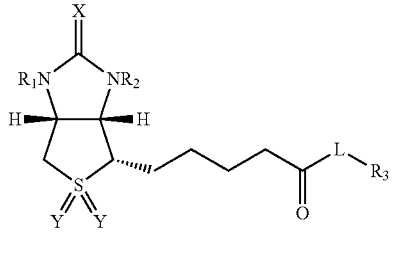

wherein:
X is S or O;
$R_1$ is selected from H and a derivative group;
$R_2$ is selected from H and a derivative group;

Y is O or absent;
L is absent or is a linker;
$R_3$ is selected from —$OR_4$, —$COOR_4$, a reactive group, a protein, a peptide, an amino acid, a dextran, a monosaccharide, a disaccharide, a trisaccharide, an oligosaccharide, a polysaccharide, a hormone, a lipopolysaccharide, a nucleotide, an oligonucleotide, a small molecule, a cell, a microplate, and a microparticle;
$R_4$ is selected from H and a derivative group;
wherein at least one of $R_1$ and $R_2$ is H;
wherein if X is O, at least one of $R_1$ and $R_2$ is not H, or Y is O.

In some embodiments, if $R_1$ is H, $R_2$ is a derivative group and if $R_2$ is H, $R_1$ is a derivative group. In some embodiments, $R_1$ is a derivative group. In some embodiments, $R_1$ comprises 1 to 8 carbon atoms, 1 to 6 carbon atoms, or 1 to 3 carbon atoms. In some embodiments, $R_2$ is a derivative group. In some embodiments, $R_2$ comprises 1 to 8 carbon atoms, 1 to 6 carbon atoms, or 1 to 3 carbon atoms. In some embodiments, X is O. In some embodiments, X is S. In some embodiments, Y is absent. In some embodiments, Y is O.

In some embodiments, a biotin derivative is provided that has the formula:

(II)

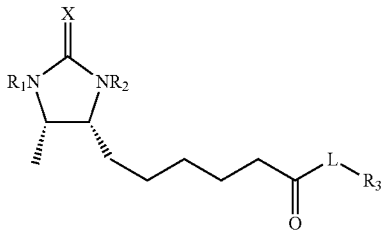

wherein:
X is S or O;
$R_1$ is selected from H and a derivative group;
$R_2$ is selected from H and a derivative group;
L is absent or is a linker;
$R_3$ is selected from —$OR_4$ or —$COOR_4$, a reactive group, a protein, a peptide, an amino acid, a dextran, a monosaccharide, a disaccharide, a trisaccharide, an oligosaccharide, a polysaccharide, a hormone, a lipopolysaccharide, a nucleotide, an oligonucleotide, a small molecule, a cell, a microplate, and a microparticle;
$R_4$ is selected from H and a derivative group;
wherein at least one of $R_1$ and $R_2$ is H.

In some embodiments, if $R_1$ is H, $R_2$ is a derivative group, and if $R_2$ is H, $R_1$ is a derivative group. In some embodiments, $R_1$ is a derivative group. In some embodiments, $R_1$ comprises 1 to 8 carbon atoms, 1 to 6 carbon atoms, or 1 to 3 carbon atoms. In some embodiments, $R_2$ is a derivative group. In some embodiments, $R_2$ comprises 1 to 8 carbon atoms, 1 to 6 carbon atoms, or 1 to 3 carbon atoms. In some embodiments, X is O. In some embodiments, X is S. In some embodiments, $R_1$ and $R_2$ are each H.

In some embodiments of the biotin derivatives of Formulae I and II, L is absent. In some embodiments, L is a linker. In some embodiments, L is selected from a polyethylene glycol linker and an oligopeptide linker. In some embodiments, the linker comprises a detectable moiety. In some embodiments, the detectable moiety is selected from a chromophore-containing moiety, a fluorescent moiety, an affinity tag, a chemiluminescent moiety, an enzyme, and an antibody. In some embodiments, the detectable moiety is selected from a chromophore, a fluorescent dye, a fluorescent protein, a phosphorescent dye, a tandem dye, a particle, a nanocrystal, a hapten, an enzyme and a molecule comprising an atom which is a radioisotope. In some embodiments, the detectable moiety is selected from a fluorescent dye, a fluorescent protein, a nanocrystal, an enzyme, and a molecule comprising an atom which is a radioisotope. In some embodiments, L-$R_3$ has the structure:

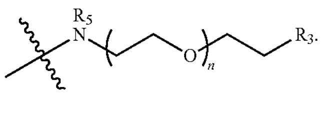

In some embodiments, $R_5$ is H or a derivative group. In some embodiments, n is an integer from 0 to 20.

In some embodiments of Formulae I and II, $R_3$ is —$OR_4$. In some embodiments, $R_3$ is —$COOR_4$. In some embodiments, $R_4$ is H. In some embodiments, $R_4$ comprises 1 to 8 carbon atoms, 1 to 6 carbon atoms, or 1 to 3 carbon atoms. In some embodiments, $R_4$ is $CH_3$. In some embodiments, $R_3$ is a reactive group. In some embodiments, the reactive group is selected from isothiocyanate, sulfonyl chloride, 4,6-dichlorotriazinyl, a carboxylate, a halo acetyl, hydrazide, a succinimidyl ester, a 4-sulfonyl-3,5-dichlorophenol ester, a maleimide, an iodoacetamide; an azide, and an alkyne, when L is a linker; or is selected from hydroxyl, hydrazinyl, N-hydroxysuccinimidyl, and 4-sulfonyl-3,5-dichlorophenol when L is absent. In some embodiments, $R_3$ is (a)

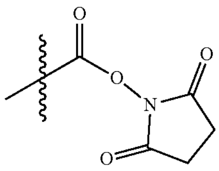

or

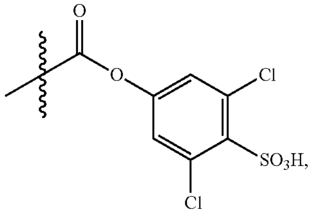

when L is a linker; or (b)

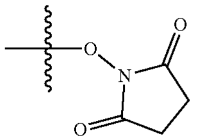

or

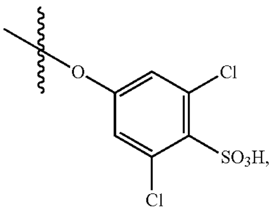

when is L is absent.

In some embodiments, $R_3$ is selected from a polypeptide, a peptide, an amino acid, a dextran, a monosaccharide, a disaccharide, a trisaccharide, an oligosaccharide, a polysaccharide, a hormone, a lipopolysaccharide, a nucleotide, an oligonucleotide, a small molecule, a cell, a microplate, and a microparticle.

In some embodiments, a biotin derivative has an affinity for streptavidin of between $1\times10^{-13}$ M and $1\times10^{-8}$ M.

In some embodiments, compositions comprising a biotin derivative and a solvent are provided. In some embodiments, the solvent is an aqueous solvent.

In some embodiments, methods of immobilizing a biotin derivative to a solid support are provided. In some embodiments, the method comprises contacting a solid support with a biotin derivative, wherein the solid support comprises a biotin-binding moiety. In some embodiments, the biotin derivative has an affinity for the biotin-binding moiety that is less than the affinity of biotin for the biotin-binding moiety. In some embodiments, the method further comprises contacting the immobilized biotin derivative with a molecule that has an affinity for the biotin-binding moiety that is greater than the affinity of the biotin derivative for the biotin-binding moiety. In some embodiments, the molecule is biotin. In some embodiments, the molecule is a biotin multimers. In some embodiments, the molecule is a biotin dimer or a biotin trimer. In some embodiments, the biotin-binding moiety is selected from avidin and streptavidin. In some embodiments, the solid support is selected from surfaces of polymer, glass, ceramic, silicone, metal, cellulose, and gel. In some embodiments, the solid support is selected from a microplate, a microarray chip, and a microparticle. In some embodiments, the biotin derivative comprises a group selected from a protein, a peptide, an amino acid, a dextran, a hormone, a lipopolysaccharide, a nucleotide, an oligonucleotide, a small molecule, and a cell.

In some embodiments, kits are provided. In some embodiments, a kit comprises a biotin derivative and/or a composition comprising a biotin derivative.

In some embodiments, methods of making biotin derivatives are provided. In some embodiments, a method comprises synthesizing a biotin derivative having the structure:

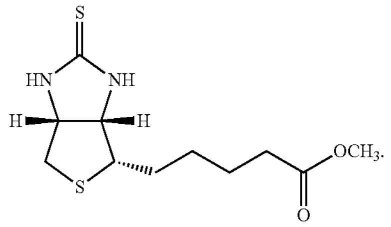 [SMILES: COC(=O)CCCC[C@@H]1SC[C@@H]2NC(=S)N[C@@H]21]

In some embodiments, the method comprises the step of reacting biotin methyl ester with Lawesson's reagent.

In some embodiments, a method comprises synthesizing a biotin derivative having the structure:

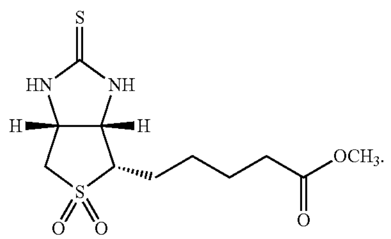 [SMILES: COC(=O)CCCC[C@H]1[C@H]2NC(=S)N[C@H]2CS1(=O)=O]

In some embodiments, the method comprises the steps of (a) reacting biotin methyl ester with Lawesson's reagent; and (b) oxidizing the ring sulfur atom with hydrogen peroxide.

In some embodiments, a method comprises synthesizing a biotin derivative having the structure:

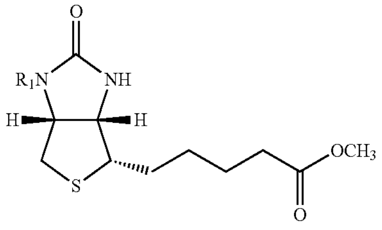

wherein $R_1$ is a derivative group.

In some embodiments, the method comprises the step of reacting biotin methyl ester with a secondary amine-reactive derivative group. In some embodiments, the secondary amine-reactive derivative group is selected from an iodoalkyl, a bromoalkyl, a chloroalkyl, and an alkyl chloroformate.

In some embodiments, a method comprises synthesizing a biotin derivative having the structure:

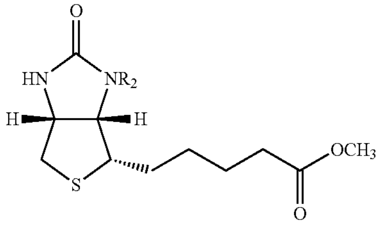

wherein $R_2$ is a derivative group.

In some embodiments, the method comprises the steps of (a) reacting biotin methyl ester with a secondary amine-reactive protecting group to make a biotin methyl ester comprising a protecting group on a ring nitrogen; (b) reacting the product of (a) with a secondary amine-reactive derivative group; and (c) removing the protecting group. In some embodiments, the secondary amine-reactive protecting group is selected from dimethoxytrityl chloride (DMTr-Cl), trityl chloride (Trt-Cl), benzyl chloroformate (Cbz-Cl), and allyl chloroformate (Aloc-Cl). In some embodiments, the secondary amine-reactive derivative group is selected from an iodoalkyl, a bromoalkyl, a chloroalkyl, and an alkyl chloroformate.

In some embodiments, a method comprises synthesizing a biotin derivative having the formula:

(I)

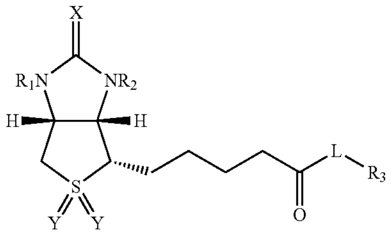

wherein:

X is S or O;

$R_1$ is selected from H and a derivative group;

$R_2$ is selected from H and a derivative group;

Y is O or absent;

L is absent or is a linker;

$R_3$ is selected from —$OR_4$, —$COOR_4$, a reactive group, a protein, a peptide, an amino acid, a dextran, a monosaccharide, a disaccharide, a trisaccharide, an oligosaccharide, a polysaccharide, a hormone, a lipopolysaccharide, a nucleotide, an oligonucleotide, a small molecule, a cell, a microplate, and a microparticle;

$R_4$ is selected from H and a derivative group;

wherein at least one of $R_1$ and $R_2$ is H;

wherein if X is O, at least one of $R_1$ and $R_2$ is not H, or Y is O.

In some embodiments, the method comprises the step of synthesizing a biotin derivative selected from:

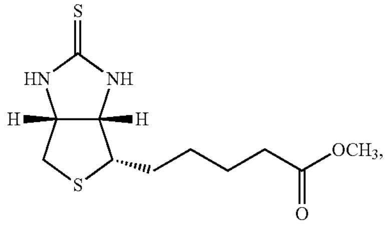

,

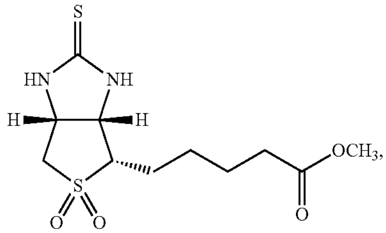

,

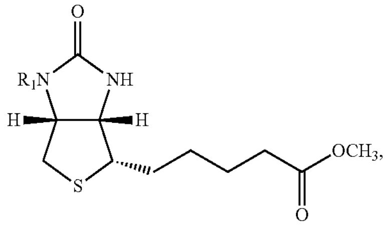

, and

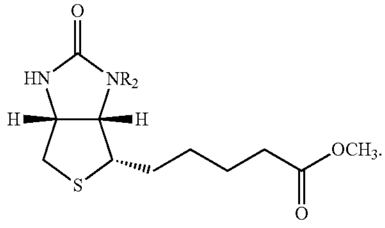

.

In some embodiments, a method comprises synthesizing a biotin derivative having the structure:

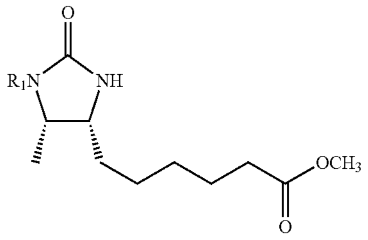

wherein $R_1$ is a derivative group.

In some embodiments, the method comprises the step of reacting desthiobiotin methyl ester with a secondary amine-reactive derivative group. In some embodiments, the secondary amine-reactive derivative group is selected from an iodoalkyl, a bromoalkyl, a chloroalkyl, and an alkyl chloroformate.

In some embodiments, a method comprises synthesizing a biotin derivative having the structure:

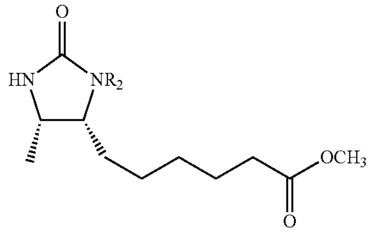

wherein $R_2$ is a derivative group.

In some embodiments, the method comprises the steps of (a) reacting desthiobiotin methyl ester with a secondary amine-reactive protecting group; and (b) reacting the product of (a) with a secondary amine-reactive derivative group. In some embodiments, the secondary amine-reactive protecting group is selected from dimethoxytrityl chloride (DMTr-Cl), trityl chloride (Trt-Cl), benzyl chloroformate (Cbz-Cl), allyl chloroformate (Aloc-Cl). In some embodiments, the secondary amine-reactive derivative group is selected from an iodoalkyl, a bromoalkyl, a chloroalkyl, and an alkyl chloroformate.

In some embodiments, a method comprises synthesizing a biotin derivative having the structure:

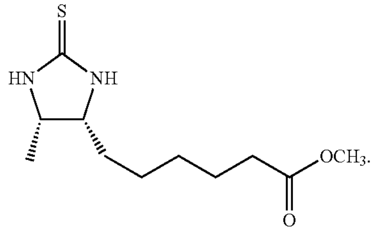

In some embodiments, the method comprises reacting desthiobiotin methyl ester with Lawesson's reagent.

In some embodiments, a method comprises synthesizing a biotin derivative having the formula:

(II)

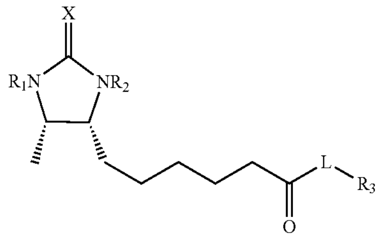

wherein:

X is S or O;

$R_1$ is selected from H and a derivative group;

$R_2$ is selected from H and a derivative group;

L is absent or is a linker;

$R_3$ is selected from —$OR_4$, —$COOR_4$, a reactive group, a protein, a peptide, an amino acid, a dextran, a monosaccharide, a disaccharide, a trisaccharide, an oligosaccharide, a polysaccharide, a hormone, a lipopolysaccharide, a nucleotide, an oligonucleotide, a small molecule, a cell, a microplate, and a microparticle;

$R_4$ is selected from H and a derivative group;

wherein at least one of $R_1$ and $R_2$ is H.

In some embodiments, the method comprises the step of synthesizing a biotin derivative selected from:

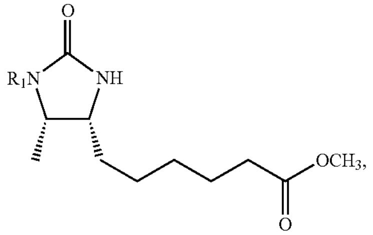

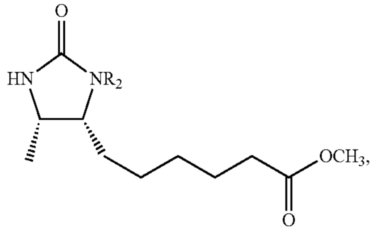

and

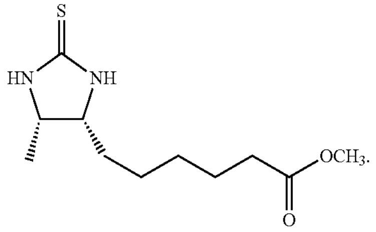 [SMILES: COC(=O)CCCCC[C@H]1NC(=S)N[C@H]1C]

In some embodiments, a method comprises the step of converting a compound selected from the group consisting of:

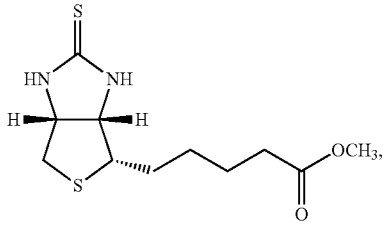

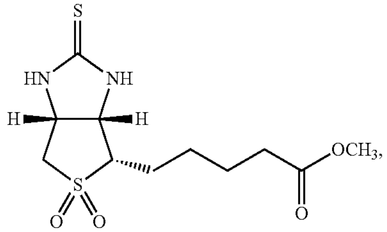

-continued

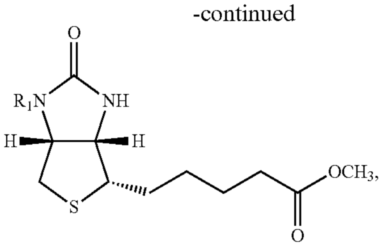

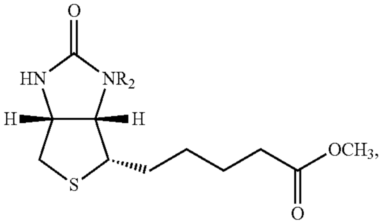

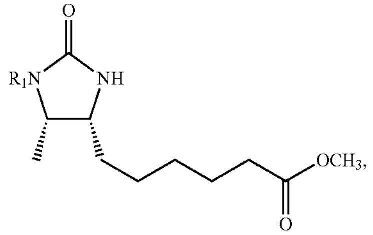

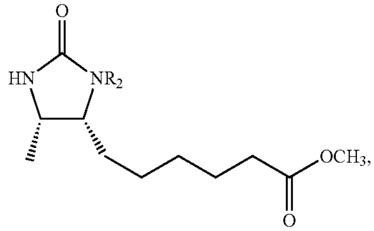

and

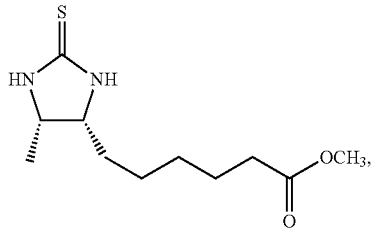

to form the biotin derivative.

In some embodiments, the biotin derivative made by this method has the formula:

(I)

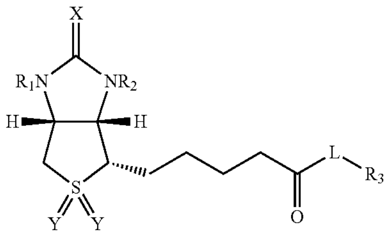

wherein:

X is S or O;

$R_1$ is selected from H and a derivative group;

$R_2$ is selected from H and a derivative group;

Y is O or absent;

L is absent or is a linker;

$R_3$ is selected from —$OR_4$, —$COOR_4$, a reactive group, a protein, a peptide, an amino acid, a dextran, a monosaccharide, a disaccharide, a trisaccharide, an oligosaccharide, a polysaccharide, a hormone, a lipopolysaccharide, a nucleotide, an oligonucleotide, a small molecule, a cell, a microplate, and a microparticle;

$R_4$ is selected from H and a derivative group;

wherein at least one of $R_1$ and $R_2$ is H;

wherein if X is O, at least one of $R_1$ and $R_2$ is not H, or Y is O.

In some embodiments, the biotin derivative made by this method has the formula:

(II)

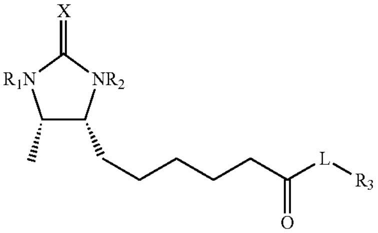

wherein:

X is S or O;

$R_1$ is selected from H and a derivative group;

$R_2$ is selected from H and a derivative group;

L is absent or is a linker;

$R_3$ is selected from —$OR_4$, —$COOR_4$, a protein, a peptide, an amino acid, a dextran, a monosaccharide, a disaccharide, a trisaccharide, an oligosaccharide, a polysaccharide, a hormone, a lipopolysaccharide, a nucleotide, an oligonucleotide, a small molecule, a cell, a microplate, and a microparticle;

$R_4$ is selected from H and a derivative group;

wherein at least one of $R_1$ and $R_2$ is H.

BRIEF DESCRIPTION OF THE FIGURES

FIG. 1A shows the fluorescence labeled protein distribution before and after streptavidin-coated agarose capture (left tube and center tube, respectively), and after release from the streptavidin coated agarose (right tube). FIG. 1B shows separation of the proteins in the cell lysate mixture (lane 1), in the supernatant following capture of the biotin derivative labeled protein (lane 2), in the wash (lane 3), and the purified protein released from the streptavidin coated agarose (lane 3).

DETAILED DESCRIPTION

Figure 1A:
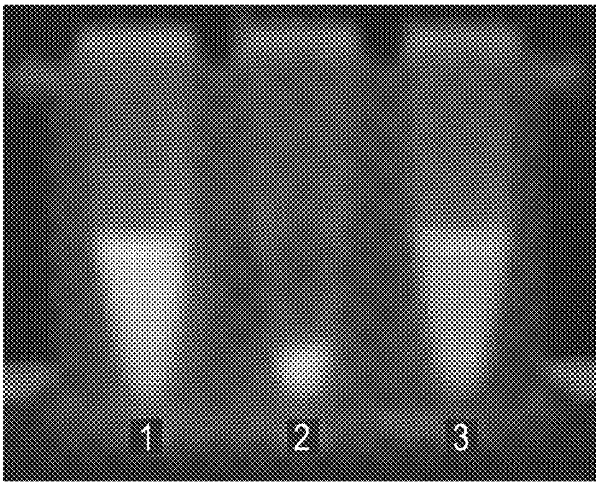
FIGS. 1A and 1B show purification of protein labeled with biotin derivative 21 from a cell lysate mixture.

The section headings used herein are for organizational purposes only and are not to be construed as limiting the subject matter described.

Unless otherwise defined, scientific and technical terms used in connection with the present invention shall have the meanings that are commonly understood by those of ordinary skill in the art. Further, unless otherwise required by context, singular terms shall include pluralities and plural terms shall include the singular.

Exemplary techniques used in connection with recombinant DNA, oligonucleotide synthesis, tissue culture, enzymatic reactions, and purification are known in the art. Many such techniques and procedures are described, e.g., in Sambrook et al. *Molecular Cloning: A Laboratory Manual* (2nd ed., Cold Spring Harbor Laboratory Press, Cold Spring Harbor, N.Y. (1989)), among other places. In addition, exemplary techniques for chemical syntheses are also known in the art.

In this application, the use of "or" means "and/or" unless stated otherwise. In the context of a multiple dependent claim, the use of "or" refers back to more than one preceding independent or dependent claim in the alternative only. Also, terms such as "element" or "component" encompass both elements and components comprising one unit and elements and components that comprise more than one subunit unless specifically stated otherwise.

Biotin Derivatives

The present invention provides biotin derivatives that are useful for applications in which it would be desirable to dissociate the biotin derivative from, for example, strepavidin under less harsh conditions, or where it would be desirable not to have such dissociation to occur. As used herein, the term "biotin derivative" includes, but is not limited to, derivatives of biotin or desthiobiotin which have a dissociation constant that is either less than or greater than the dissociation constant of biotin or desthiobiotin for either avidin or strepavidin.

In some embodiments, a biotin derivative is provided that has the formula:

(I)

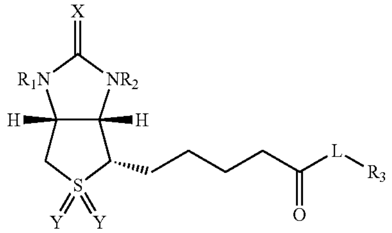

In some embodiments, X is S or O. In some embodiments $R_1$ is selected from H and a derivative group. In some embodiments, $R_2$ is selected from H and a derivative group. In some embodiments, Y is O or absent. In some embodiments, L is absent or is a linker. In some embodiments, at least one of $R_1$ and $R_2$ is H. In some embodiments, if X is O, at least one or $R_1$ and $R_2$ is not H. In some embodiments, if X is O, Y is O. In some embodiments, if $R_1$ is H, $R_2$ is a derivative group. In some embodiments, if $R_2$ is H, $R_1$ is a derivative group. In some embodiments, $R_3$ is selected from —$RO_4$, —$COOR_4$, a reactive group, a protein, a peptide, an amino acid, a dextran, a monosaccharide, a disaccharide, a trisaccharide, an oligosaccharide, a polysaccharide, a hormone, a lipopolysaccharide, a nucleotide, an oligonucleotide, a small molecule, a cell, a microplate, and a microparticle.

In some embodiments, a biotin derivative is provided that has the formula:

(II)

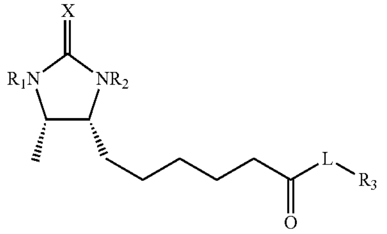

In some embodiments, X is S or O. In some embodiments, $R_1$ is selected from H and a derivative group. In some embodiments, $R_2$ is selected from H and a derivative group. In some embodiments, L is absent or is a linker. In some embodiments, if X is S, at least one of $R_1$ and $R_2$ is H. In some embodiments, if X is O, at least one of $R_1$ and $R_2$ is not H. In some embodiments, if $R_1$ is H, $R_2$ is a derivative group. In some embodiments, if $R_2$ is H, $R_1$ is a derivative group.

In some embodiments, $R_3$ is selected from —$RO_4$, —$COOR_4$, a reactive group, a protein, a peptide, an amino acid, a dextran, a monosaccharide, a disaccharide, a trisaccharide, an oligosaccharide, a polysaccharide, a hormone, a lipopolysaccharide, a nucleotide, an oligonucleotide, a small molecule, a cell, a microplate, and a microparticle.

The term "derivative group" as used herein refers to a substituted or unsubstituted straight chain, branched chain, cyclic, or a combination thereof, carbon radical that may be fully saturated, mono-unsaturated, or poly-unsaturated, and which comprises 1 to 12 carbon atoms (i.e., $C_1$ to $C_{12}$). Exemplary saturated groups include, but are not limited to, alkyl groups such as methyl, ethyl, n-propyl, isopropyl, n-butyl, t-butyl, isobutyl, sec-butyl, cyclohexyl, (cyclohexyl)methyl, cyclopropylmethyl, and homologs and isomers of, for example, n-pentyl, n-hexyl, n-heptyl, n-octyl, n-nonyl, n-decyl and the like. An unsaturated group is a group having one or more double bonds, such as alkenyl groups, or triple bonds, such as alkynyl groups. Examples of unsaturated derivative groups include, but are not limited to, vinyl, 2-propenyl, crotyl, 2-isopentenyl, 2-(butadienyl), 2,4-pentadienyl, 3-(1,4-pentadienyl), ethynyl, 1- and 3-propynyl, 3-butynyl, and the higher (i.e., having more carbon atoms) homologs and isomers.

The term derivative group includes groups that comprise one or more heteroatom substituents selected from O, N, Si, P, and S. Exemplary such derivative groups include straight chain, branched chain, cyclic, or a combination thereof, carbon-containing radicals, which comprise the stated number of carbon atoms and at least one heteroatom selected from O, N, Si, P, and S, and wherein the nitrogen, phosphorous and/or sulfur atoms may be optionally oxidized, and a nitrogen heteroatom may be optionally be quaternized. In some embodiments, one or more heteroatoms may be placed at interior positions of the derivative group, or at a position at which the derivative group is attached to the remainder of a molecule. Thus, derivative groups include, but are not limited to, alkoxy groups, alkylamino groups, and alkylthio groups.

The term derivative group also includes groups comprising carbon atoms substituted with one or more halogens in place of one or more hydrogens. Exemplary halogens that may be present in such derivative groups include F, Br, Cl, and I.

In some embodiments, a derivative group comprises 1 to 11 carbon atoms (i.e., $C_1$ to $C_{11}$), 1 to 10 carbon atoms (i.e., $C_1$ to $C_{10}$), 1 to 9 carbon atoms (i.e., $C_1$ to $C_9$), 1 to 8 carbon atoms (i.e., $C_1$ to $C_8$), 1 to 7 carbon atoms (i.e., $C_1$ to $C_7$), 1 to 6 carbon atoms (i.e., $C_1$ to $C_6$), 1 to 5 carbon atoms (i.e., $C_1$ to $C_5$), 1 to 4 carbon atoms ($C_1$ to $C_4$), 1 to 3 carbon atoms ($C_1$ to $C_3$), or 1 to 2 carbon atoms ($C_1$ to $C_2$). In some embodiments, derivative group is a saturated or unsaturated straight chain or branched chain carbon radical.

The term "linker" as used herein refers to a chemical moiety that links a biotin derivative of any one of Formulae I to VI to another molecule, such as a reactive group, a protein, a peptide, an amino acid, a dextran, a monosaccharide, a disaccharide, a trisaccharide, an oligosaccharide, a polysaccharide, a hormone, a lipopolysaccharide, a molecule on the surface of a cell, a nucleotide, an oligonucleotide, a small molecule, a molecule on the surface of a microplate, and a molecule on the surface of a microparticle. In some embodiments, a linker is a polymer or a biopolymer. Nonlimiting exemplary linkers include polyethylene glycol linkers and oligopeptide linkers (also referred to simply as peptide linkers). Many linkers are known in the art. One skilled in the art can select a suitable linker according to the intended application.

In some embodiments, a linker comprises a detectable moiety.

The term "detectable moiety" as used herein refers to a moiety that facilitates detection of a molecule, and would include any moiety detectable by any means known in the art. Nonlimiting exemplary detectable moieties include chromophore-containing moieties, fluorescent moieties, affinity tags, chemiluminescent moieties, enzymes, antibodies, and a molecule comprising an atom which is a radioisotope. Many detectable moieties are known in the art which include, but are not limited to, a chromophore, a fluorescent dye, a fluorescent protein, a phosphorescent dye, a tandem dye, a particle, a nanocrystal, a hapten, an enzyme, a molecule comprising an atom which is a radioisotope or an atom which is a radioisotope. Numerous fluorescent dyes are known to those skilled in the art and include, but are not limited to, coumarin, cyanine, benzofuran, a quinoline, a quinazolinone, an indole, a benzazole, a borapolyazaindacene and xanthenes including fluoroscein, rhodamine and rhodol. The presence of a detectable moiety is, directly or indirectly, detectable. For example, radiolabels that can be measured with radiation-counting devices; pigments, dyes or other chromogens that can be visually observed or measured with a spectrophotometer; spin labels that can be measured with a spin label analyzer; and fluorescent moieties (fluorophores), where the output signal is generated by the excitation of a suitable molecular adduct and that can be visualized by excitation with light that is absorbed by the dye or can be measured with standard fluorometers or imaging systems. One skilled in the art can select a suitable detectable moiety according to the intended use.

The term "reactive group" as used herein refers to a chemical moiety that is part of a first molecule that is capable of reacting with a "complementary group" that is part of a second molecule to form a covalent bond between the first molecule and the second molecule. Complementary group may also be called "complementary reactive group". In some embodiments, a reactive group is an electrophilic group and a complementary group is a nucleophilic group. In some embodiments, a reactive group is a nucleophilic group and a complementary group is an electrophilic group. In some embodiments, the reactive group is an azide and the complementary group is an alkyne. In some embodiments the reactive group is an alkyne and the complementary group is an azide. The term, "alkyne", includes, but is not limited to, a moiety comprising a terminal carbon-carbon triple bond, such as, for example, acetylene. The term also includes, but is not limited to, a moiety comprising an activated carbon-carbon triple bond, such as for example, cyclooctynes and difluorcyclooctynes, dibenzocyclooctynes, and aza-dibenzocyclooctynes. In some embodiments, a reactive group is part of a molecule selected from Formulae I to VI. In some embodiments, a complementary group is part of a second molecule selected from a protein, a peptide, an amino acid, a dextran, a monosaccharide, a disaccharide, a trisaccharide, an oligosaccharide, a polysaccharide, a hormone, a lipopolysaccharide, a molecule on the surface of a cell, a nucleotide, an oligonucleotide, a small molecule, a molecule on the surface of a microplate, and a molecule on the surface of a microparticle. In some embodiments, a complementary group is an amine.

Nonlimiting exemplary reactive groups include isothiocyanate, sulfonyl chloride, 4,6-dichlorotriazinyl, carboxylates, halo acetals (such as an acid chloride), hydrazides, succinimidyl esters (such as N-hydroxysuccinimidyl (NHS) ester), phenol esters (such as 4-sulfonyl-3,5-dichlorophenol ester), maleimides, an azide, an alkyne, and iodoacetamide, when L is a linker; or hydroxyl, hydrazinyl, N-hydroxysuccinimidyl, and 4-sulfonyl-3,5-dichlorophenol when L is absent. Nonlimiting exemplary reactive groups also include, but are not limited to, olefins, acetylenes, alcohols, phenols, ethers, oxides, halides, aldehydes, ketones, esters, amines, amides, cyanates, isocyanates, thiocyanates, isothiocyanates, hydrazines, hydrazones, diazo groups, diazonium groups, nitro groups, nitriles, mercaptans, sulfides, disulfides, sulfoxides, sulfones, sulfonic acid groups, sulfinic acid groups, acetals, ketals, anhydrides, sulfates, sulfenic acid groups, isonitriles, amidines, imides, imidates, nitrones, hydroxylamines, oximes, hydroxamic acid groups, thiohydroxamic acid groups, allenes, ortho esters, sulfites, enamines, ynamines, ureas, pseudoureas, semicarbazides, carbodiimides, carbamates, imines, azides, alkyne, azo groups, azoxy groups, and nitroso groups.

In some embodiments, a biotin derivative is provided that has the formula:

(III)

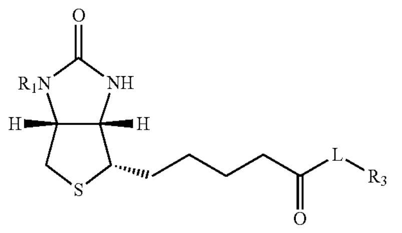

In some embodiments, $R_1$ is a derivative group. In some embodiments, L is absent or is a linker. In some embodiments, $R_3$ is selected from —$RO_4$, —$COOR_4$, a reactive group, a protein, a peptide, an amino acid, a dextran, a monosaccharide, a disaccharide, a trisaccharide, an oligosaccharide, a polysaccharide, a hormone, a lipopolysaccharide, a nucleotide, an oligonucleotide, a small molecule, a cell, a microplate, and a microparticle.

In some embodiments, a biotin derivative is provided that has the formula:

(IV)

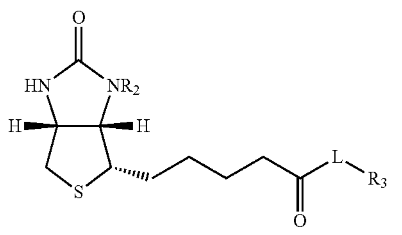

In some embodiments, $R_2$ is a derivative group. In some embodiments, L is absent or is a linker. In some embodiments, $R_3$ is selected from —$RO_4$, —$COOR_4$, a reactive group, a protein, a peptide, an amino acid, a dextran, a monosaccharide, a disaccharide, a trisaccharide, an oligosaccharide, a polysaccharide, a hormone, a lipopolysaccharide, a nucleotide, an oligonucleotide, a small molecule, a cell, a microplate, and a microparticle.

In some embodiments, a biotin derivative is provided that has the formula:

(V)

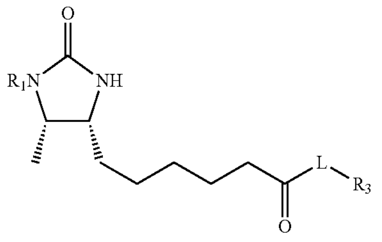

In some embodiments, $R_1$ is a derivative group. In some embodiments, L is absent or is a linker. In some embodiments, $R_3$ is selected from —$RO_4$, —$COOR_4$, a reactive group, a protein, a peptide, an amino acid, a dextran, a monosaccharide, a disaccharide, a trisaccharide, an oligosaccharide, a polysaccharide, a hormone, a lipopolysaccharide, a nucleotide, an oligonucleotide, a small molecule, a cell, a microplate, and a microparticle.

In some embodiments, a biotin derivative is provided that has the formula:

(VI)

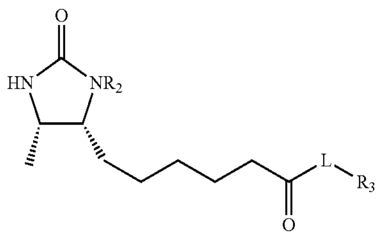

In some embodiments, $R_2$ is a derivative group. In some embodiments, L is absent or is a linker. In some embodiments, $R_3$ is selected from —$RO_4$, —$COOR_4$, a reactive group, a protein, a peptide, an amino acid, a dextran, a monosaccharide, a disaccharide, a trisaccharide, an oligosaccharide, a polysaccharide, a hormone, a lipopolysaccharide, a nucleotide, an oligonucleotide, a small molecule, a cell, a microplate, and a microparticle.

Certain nonlimiting exemplary biotin derivatives are shown in Tables 1, 2, 3, and 4. Table 1 shows certain nonlimiting exemplary biotin derivative structures in which L and $R_3$ are not specified. As noted above, L may be absent or may be a linker. Many different linkers and/or $R_3$ groups may be used in the structures in Table 1. One skilled in the art can select a suitable linker (or select the absence of a linker) and a suitable $R_3$ group according to the intended application.

Table 2 shows certain nonlimiting exemplary biotin derivative structures in which the $R_3$ group is not specified. One skilled in the art can select a suitable $R_3$ group according to the intended application. Certain linkers are represented in the structures in Table 2. Those linkers are in no way exhaustive of the possible linkers that could be used, for example, in the structures in Table 1, or in Formulae I to VI.

Table 3 shows certain nonlimiting exemplary biotin derivatives. Each of those biotin derivatives comprises the reactive group N-hydroxysuccinimidyl (NHS) ester as $R_3$. While those structures are shown with NHS, that representation is in no way exhaustive of the possible reactive groups, or $R_3$ groups, that could be used, for example, in the structures in Table 1, or in Formulae I to VI.

Table 4 shows certain nonlimiting exemplary biotin derivatives. Each of those structures comprises an ester group (—$COOR_4$), which may be a carboxylic acid when $R_4$ is H.
TABLE 1
Nonlimiting exemplary biotin derivative structures
| Compound | Structure |
|---|---|
| 29 | 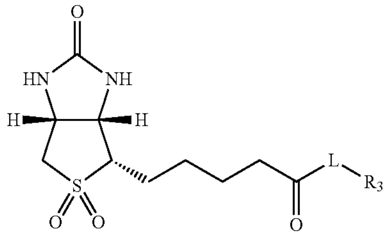 |
| 30 | 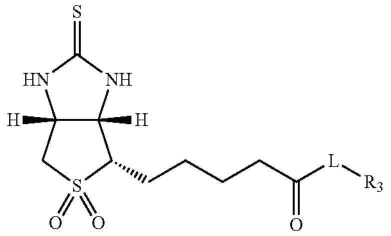 |
| 31 | 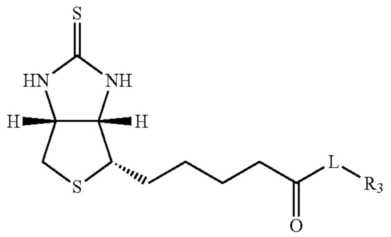 |
| 32 | 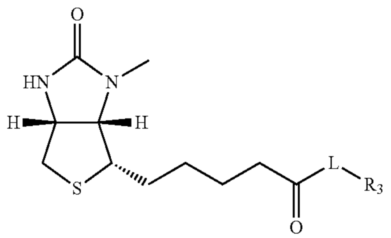 |
| 33 | 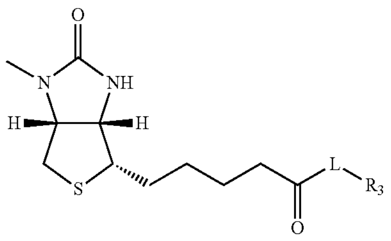 |
TABLE 1-continued
Nonlimiting exemplary biotin derivative structures
| Compound | Structure |
|---|---|
| 34 | 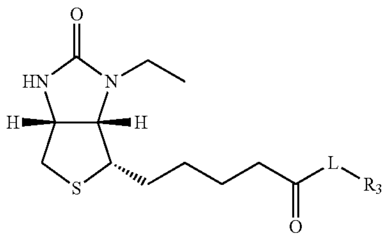 |
| 35 | 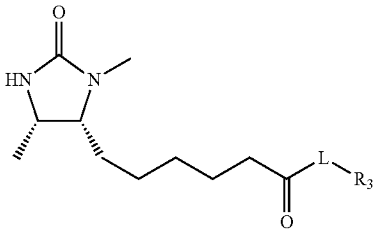 |
| 36 | 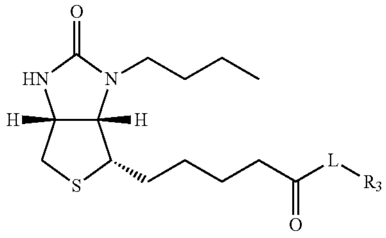 |
| 37 | 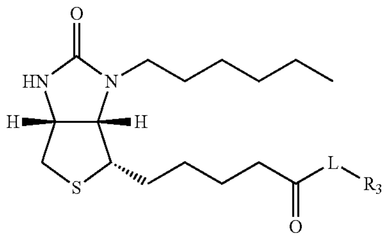 |
| 38 | 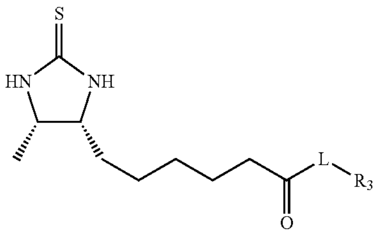 |

TABLE 2
| Nonlimiting exemplary biotin derivative structures | |
|---|---|
| 39 | 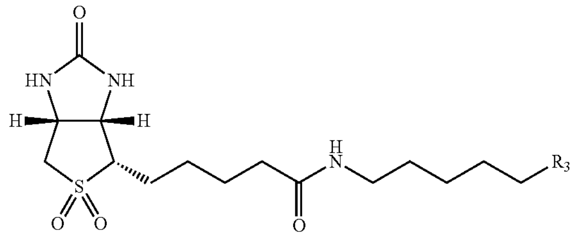 |
| 40 | 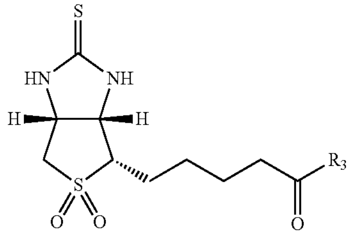 |
| 41 | 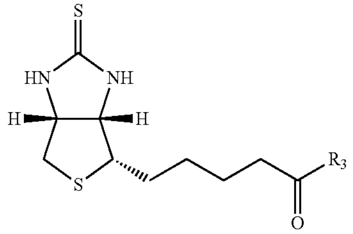 |
| 42 | 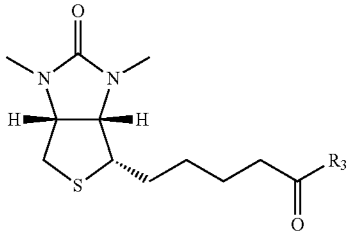 |
| 43 | 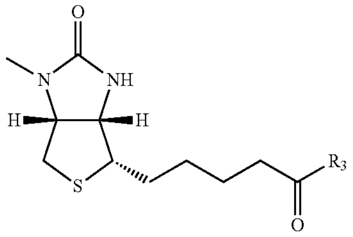 |
| 44 | 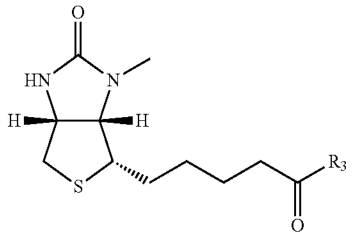

TABLE 2-continued
| Nonlimiting exemplary biotin derivative structures | |
|---|---|
| 45 | 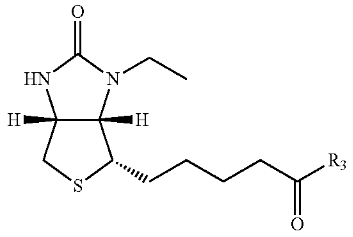 |
| 46 | 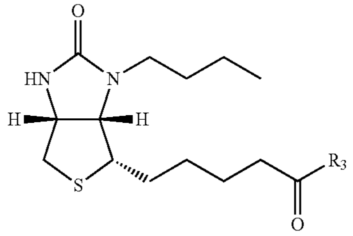 |
| 47 | 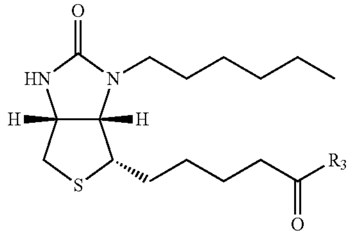 |
| 48 | 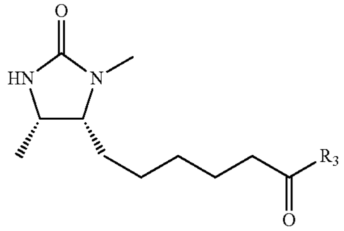 |
| 49 | 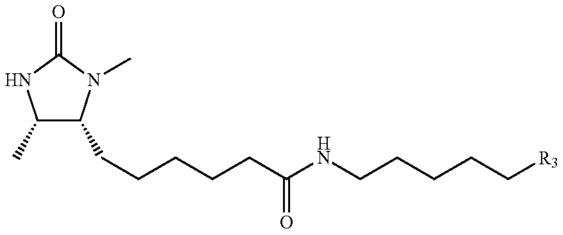 |
| 50 | 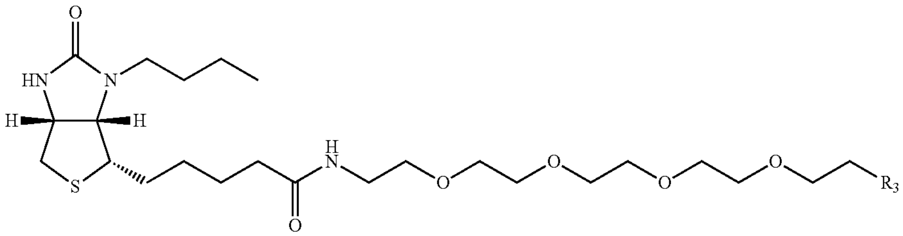 |

TABLE 2-continued
| Nonlimiting exemplary biotin derivative structures | |
|---|---|
| 51 | 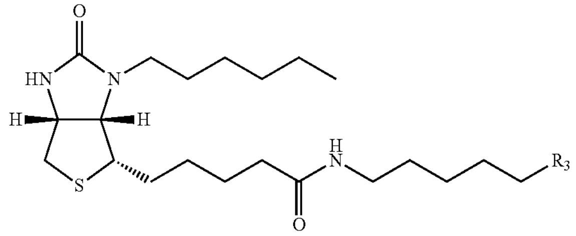 |
| 52 | 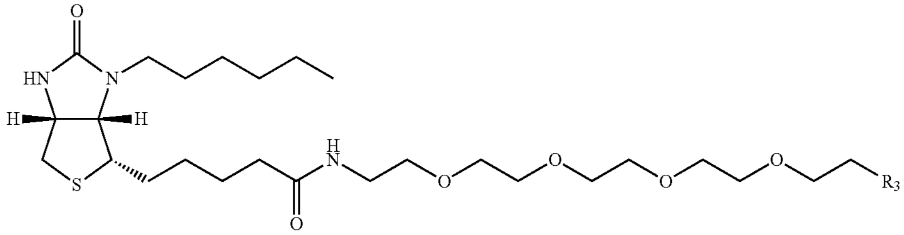 |
| 53 | 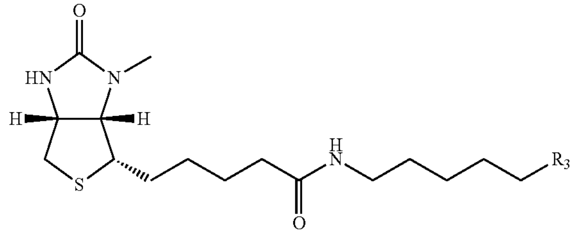 |
| 111 | 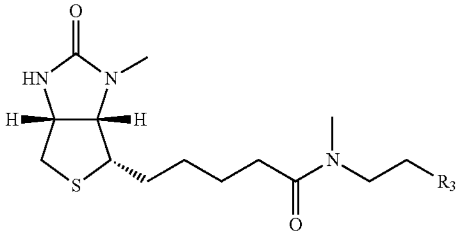 |
| 112 | 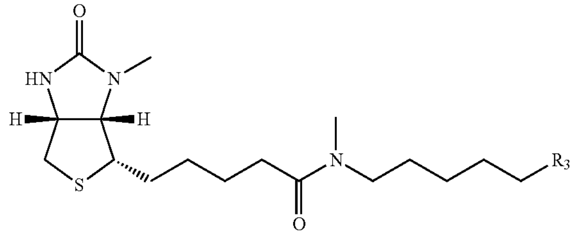 |
| 54 | 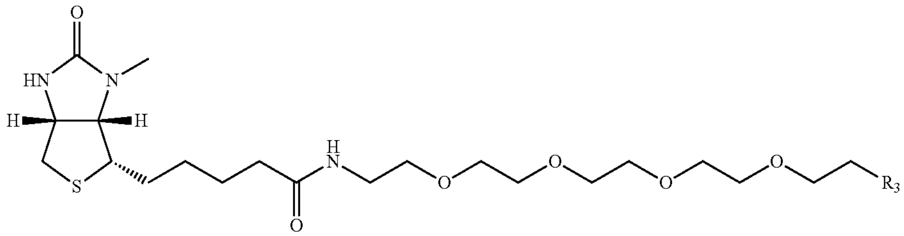 |

TABLE 2-continued
| Nonlimiting exemplary biotin derivative structures |
| --- |
| 55 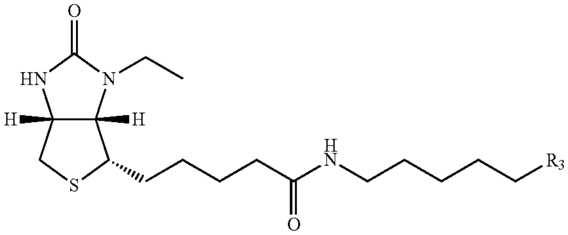 |
| 56 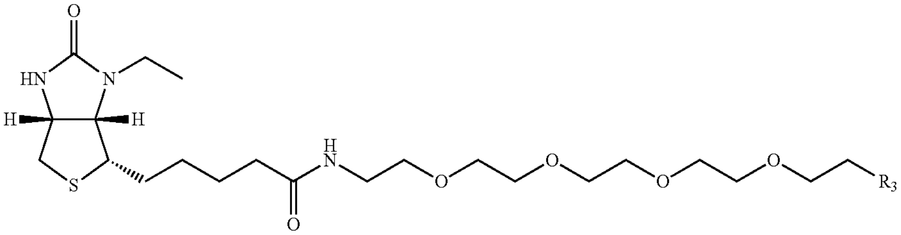 |
| 57 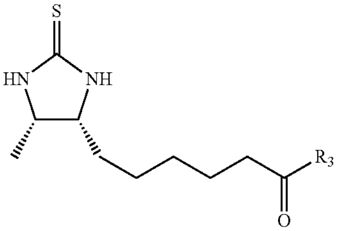 |
| 58 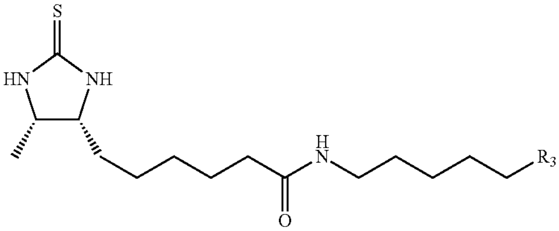 |
| 59 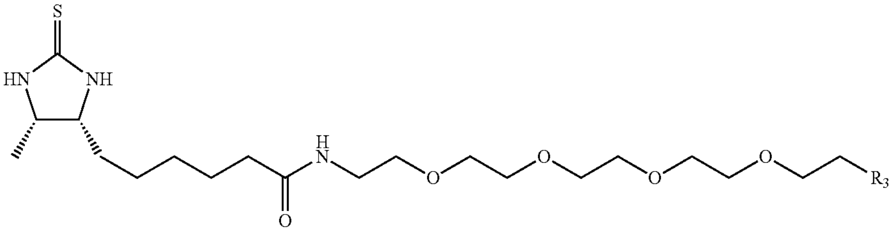 |

TABLE 2-continued
| Nonlimiting exemplary biotin derivative structures |
| --- |
| 60 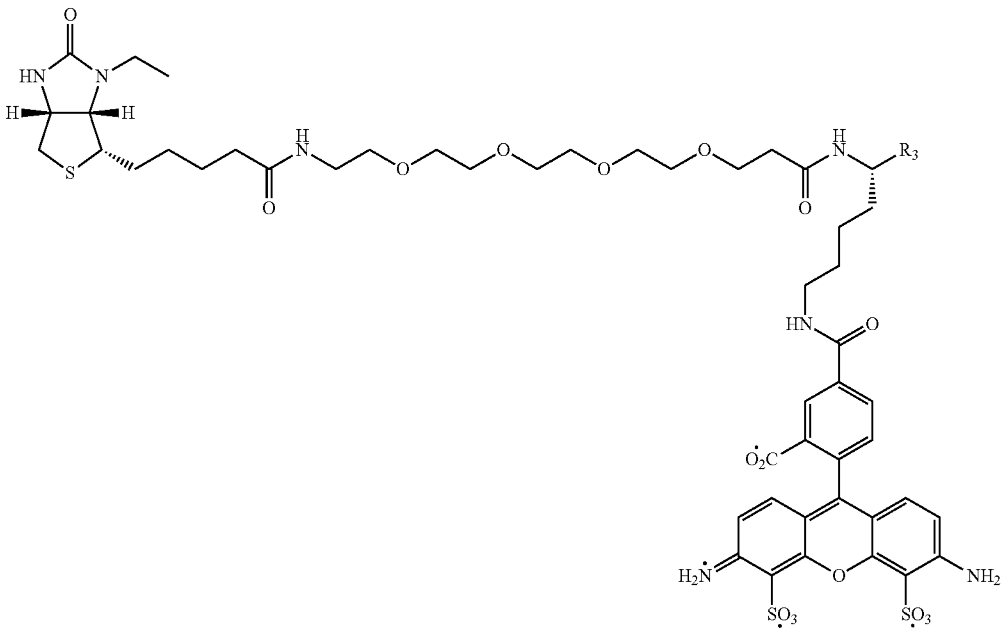 |
| 61 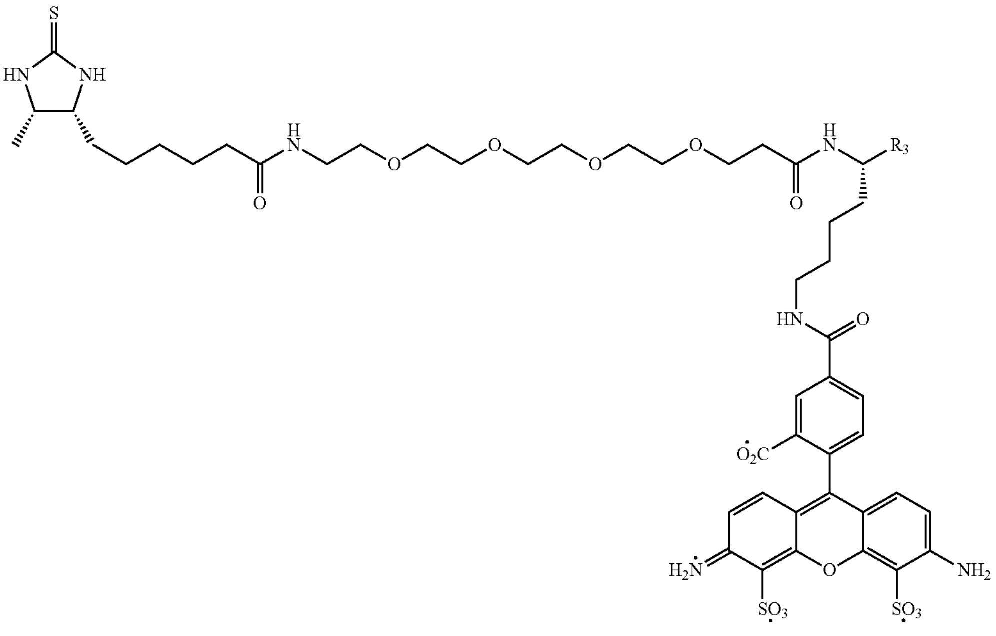 |

TABLE 3
| Nonlimiting exemplary biotin derivative structures | |
|---|---|
| 1 | 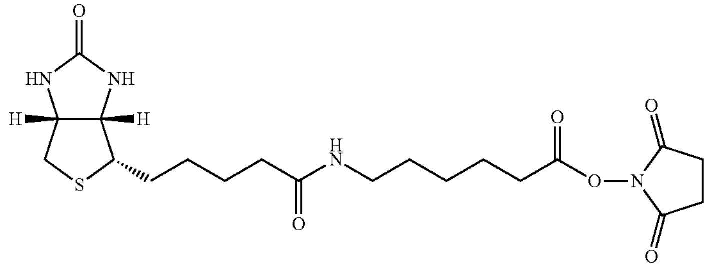 [SMILES: O=C(CCCC[C@@H]1SC[C@@H]2NC(=O)N[C@@H]21)NCCCCCC(=O)ON1C(=O)CCC1=O] |
| 2 | 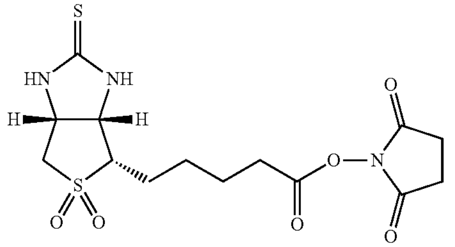 [SMILES: O=C(CCCC[C@H]1[C@H]2NC(=S)N[C@H]2CS1(=O)=O)ON1C(=O)CCC1=O] |
| 3 | 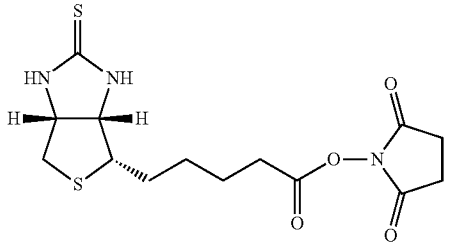 [SMILES: O=C(CCCC[C@@H]1SC[C@@H]2NC(=S)N[C@@H]21)ON1C(=O)CCC1=O] |
| 4 | 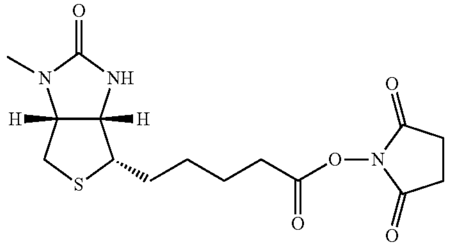 [SMILES: CN1C(=O)N[C@@H]2[C@H](CCCCC(=O)ON3C(=O)CCC3=O)SC[C@@H]21] |
| 5 | 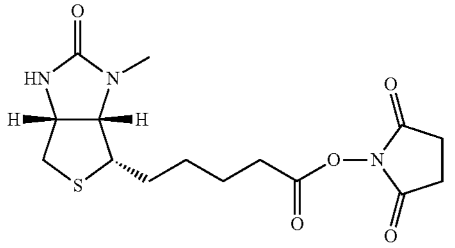 |
| 113 | 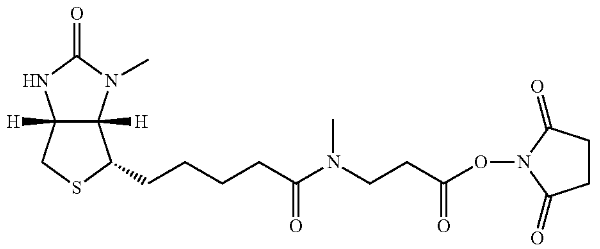 [SMILES: CN(CCC(=O)ON1C(=O)CCC1=O)C(=O)CCCC[C@@H]1SC[C@@H]2NC(=O)N(C)[C@@H]21] |

TABLE 3-continued
| Nonlimiting exemplary biotin derivative structures | |
|---|---|
| 114 | 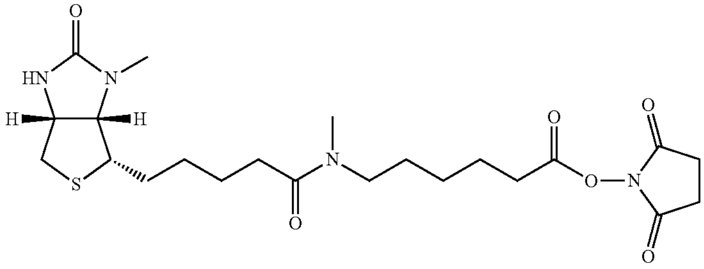 [SMILES: CN(CCCCCC(=O)ON1C(=O)CCC1=O)C(=O)CCCC[C@@H]1SC[C@@H]2NC(=O)N(C)[C@@H]21] |
| 6 | 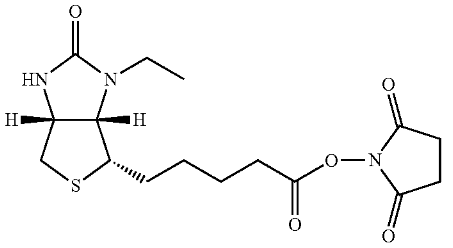 [SMILES: CCN1C(=O)N[C@H]2CS[C@@H](CCCCC(=O)ON3C(=O)CCC3=O)[C@H]21] |
| 7 | 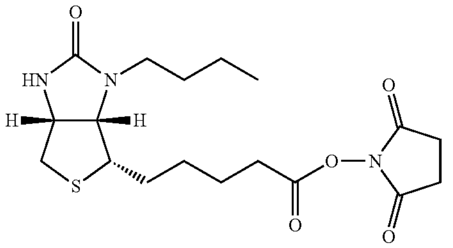 [SMILES: CCCCN1C(=O)N[C@H]2CS[C@@H](CCCCC(=O)ON3C(=O)CCC3=O)[C@H]21] |
| 8 | 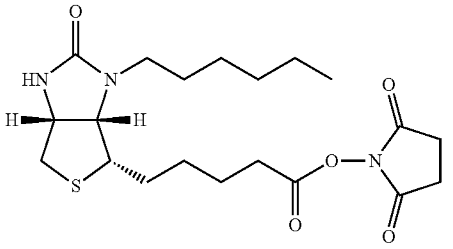 [SMILES: CCCCCCN1C(=O)N[C@H]2CS[C@@H](CCCCC(=O)ON3C(=O)CCC3=O)[C@H]21] |
| 9 | 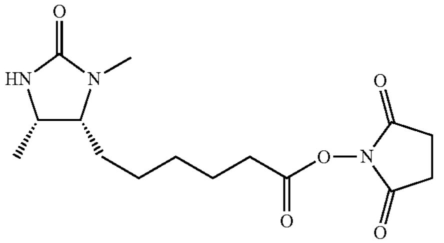 [SMILES: C[C@@H]1NC(=O)N(C)[C@@H]1CCCCCC(=O)ON1C(=O)CCC1=O] |
| 10 | 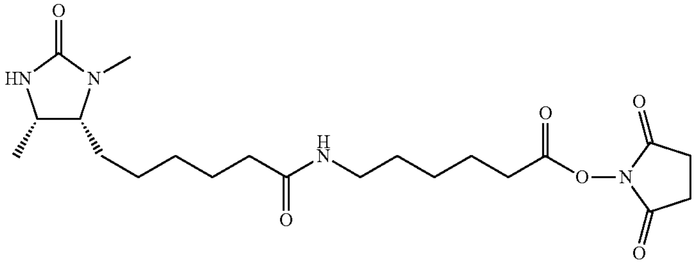 [SMILES: C[C@@H]1NC(=O)N(C)[C@@H]1CCCCCC(=O)NCCCCCC(=O)ON1C(=O)CCC1=O] |

TABLE 3-continued
| Nonlimiting exemplary biotin derivative structures | |
|---|---|
| 11 | 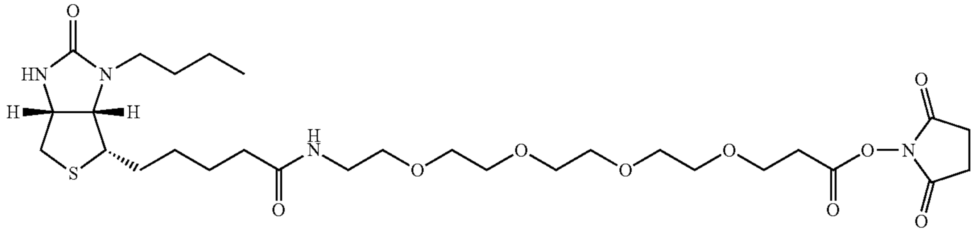 [SMILES: CCCCN1C(=O)N[C@H]2CS[C@@H](CCCCC(=O)NCCOCCOCCOCCOCCC(=O)ON3C(=O)CCC3=O)[C@H]21] |
| 12 | 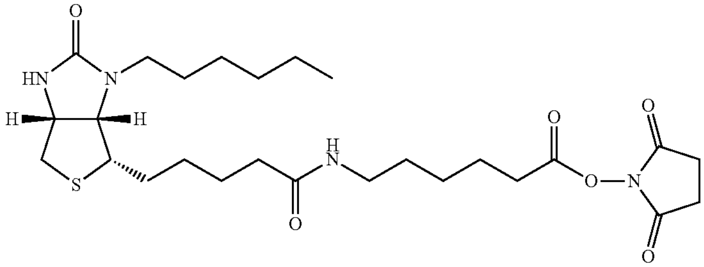 [SMILES: CCCCCCN1C(=O)N[C@H]2CS[C@@H](CCCCC(=O)NCCCCCC(=O)ON3C(=O)CCC3=O)[C@H]21] |
| 13 | 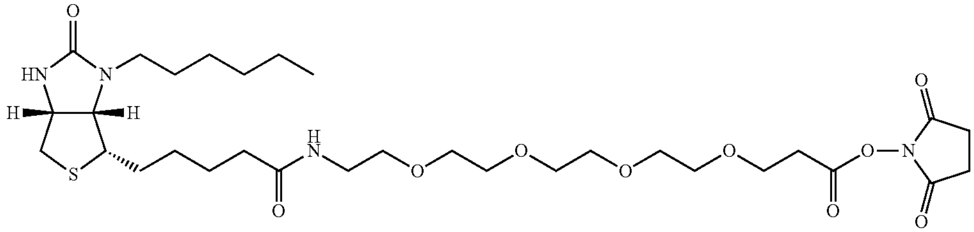 [SMILES: CCCCCCN1C(=O)N[C@H]2CS[C@@H](CCCCC(=O)NCCOCCOCCOCCOCCC(=O)ON3C(=O)CCC3=O)[C@H]21] |
| 14 | 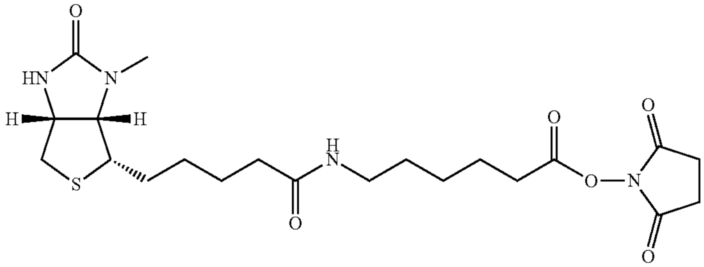 [SMILES: CN1C(=O)N[C@H]2CS[C@@H](CCCCC(=O)NCCCCCC(=O)ON3C(=O)CCC3=O)[C@H]21] |
| 15 | 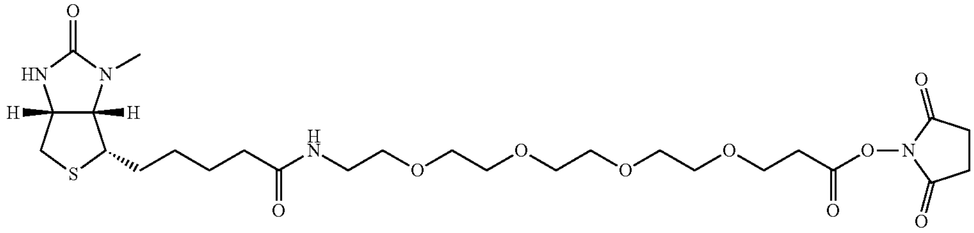 [SMILES: CN1C(=O)N[C@H]2CS[C@@H](CCCCC(=O)NCCOCCOCCOCCOCCC(=O)ON3C(=O)CCC3=O)[C@H]21] |
| 16 | 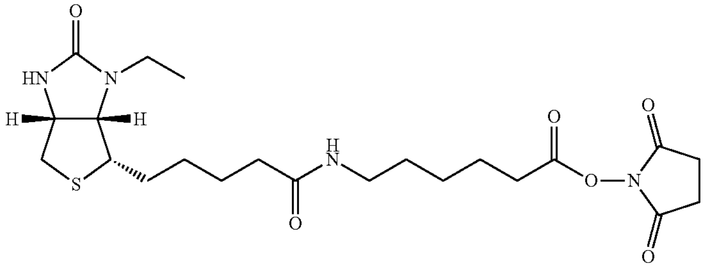 [SMILES: CCN1C(=O)N[C@H]2CS[C@@H](CCCCC(=O)NCCCCCC(=O)ON3C(=O)CCC3=O)[C@H]21] |

TABLE 3-continued
| Nonlimiting exemplary biotin derivative structures |
| --- |
| 17 |
| 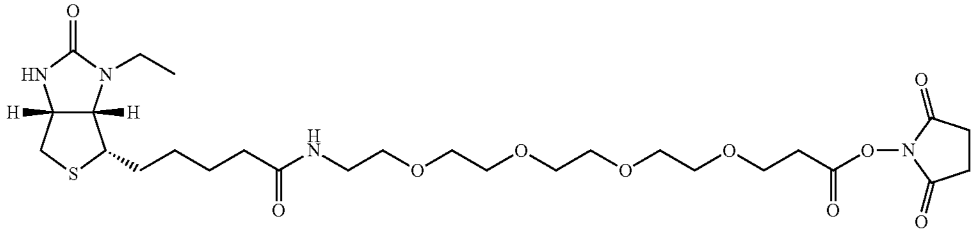 [SMILES: CCN1C(=O)N[C@H]2CS[C@@H](CCCCC(=O)NCCOCCOCCOCCOCCC(=O)ON3C(=O)CCC3=O)[C@H]21] |
| 18 |
| 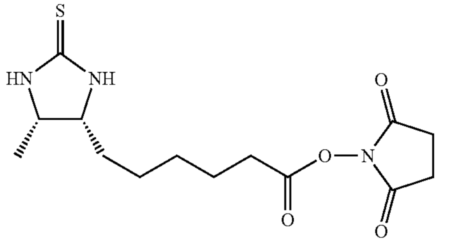 [SMILES: C[C@@H]1NC(=S)N[C@@H]1CCCCCC(=O)ON1C(=O)CCC1=O] |
| 19 |
| 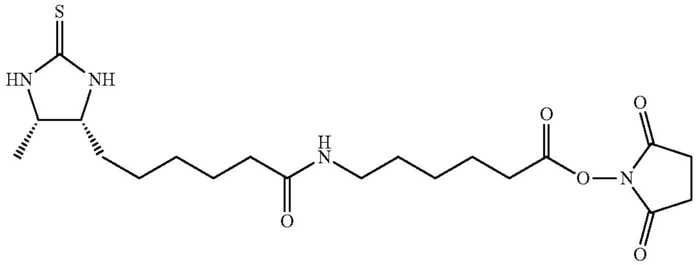 [SMILES: C[C@@H]1NC(=S)N[C@@H]1CCCCCC(=O)NCCCCCC(=O)ON1C(=O)CCC1=O] |
| 20 |
| 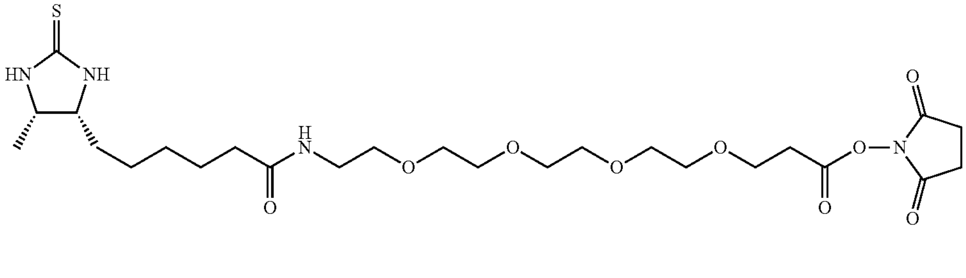 [SMILES: C[C@@H]1NC(=S)N[C@@H]1CCCCCC(=O)NCCOCCOCCOCCOCCC(=O)ON1C(=O)CCC1=O] |

TABLE 3-continued
| Nonlimiting exemplary biotin derivative structures |
| --- |
| 21 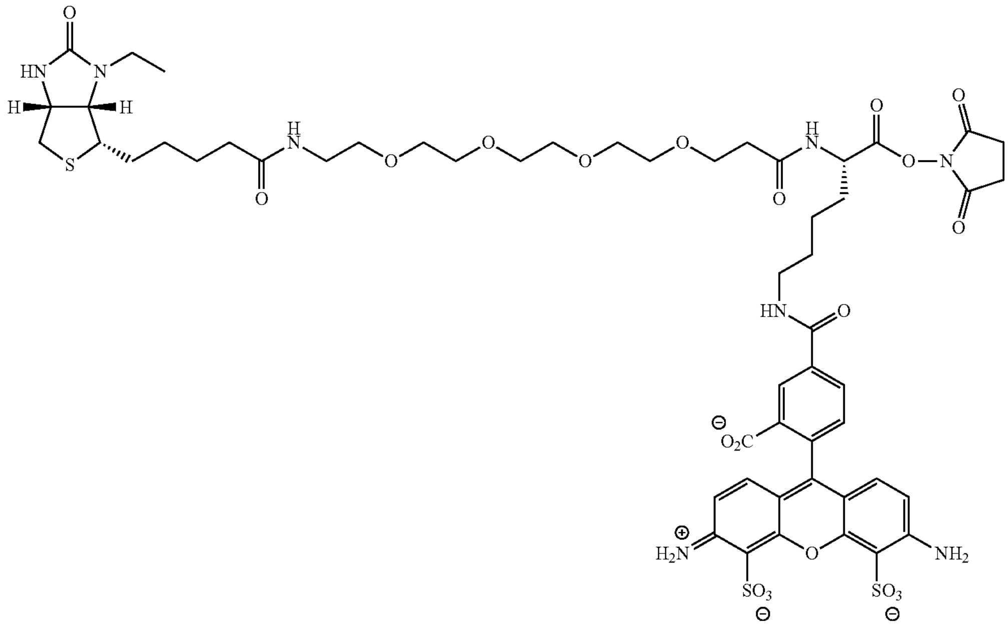 |
| 22 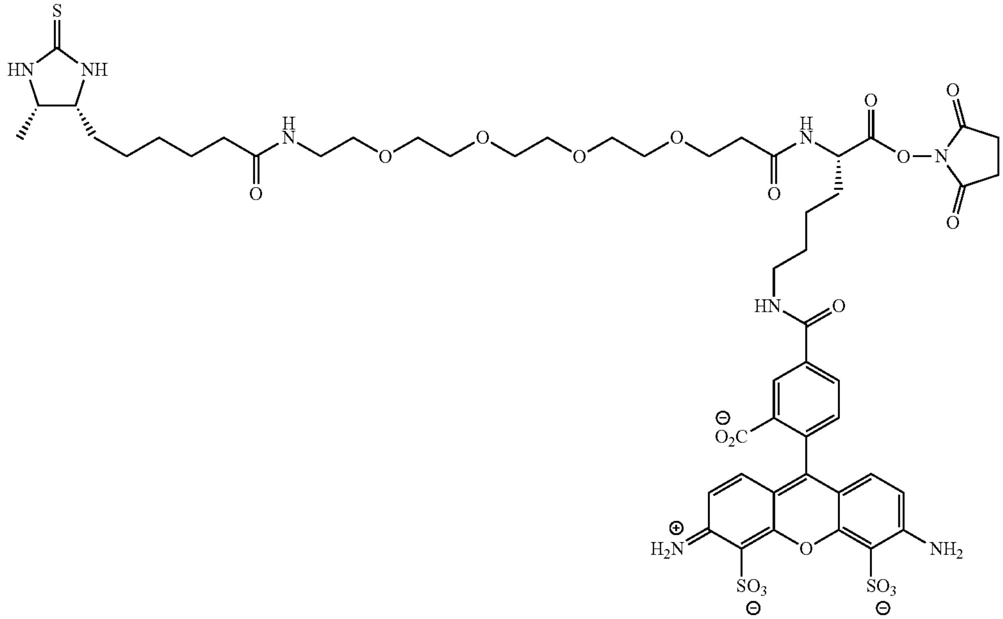 |
| 23 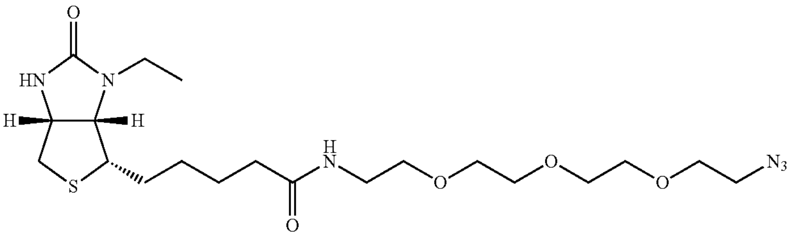 [SMILES: CCN1C(=O)N[C@H]2CS[C@@H](CCCCC(=O)NCCOCCOCCOCCN=[N+]=[N-])[C@H]21] |

TABLE 3-continued
| Nonlimiting exemplary biotin derivative structures | |
|---|---|
| 24 | 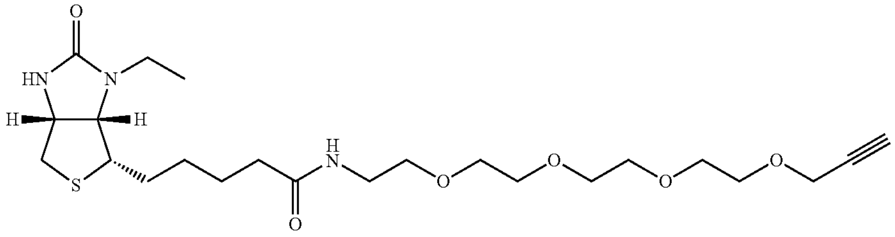 [SMILES: C#CCOCCOCCOCCOCCNC(=O)CCCC[C@@H]1SC[C@@H]2NC(=O)N(CC)[C@@H]21] |
| 25 | 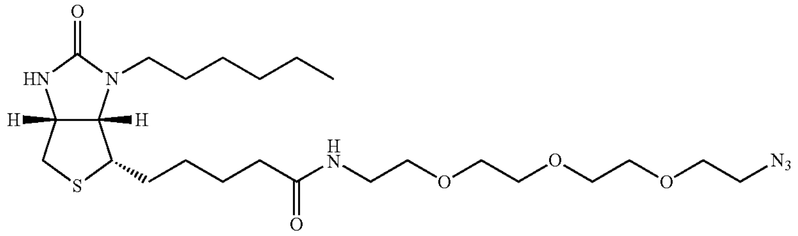 [SMILES: CCCCCCN1C(=O)N[C@H]2CS[C@@H](CCCCC(=O)NCCOCCOCCOCCN=[N+]=[N-])[C@H]21] |
| 26 | 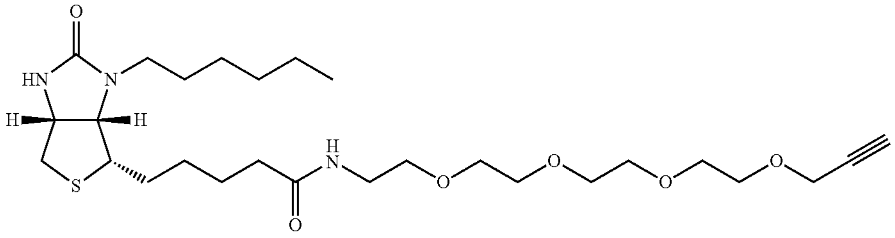 [SMILES: C#CCOCCOCCOCCOCCNC(=O)CCCC[C@@H]1SC[C@@H]2NC(=O)N(CCCCCC)[C@@H]21] |
| 27 | 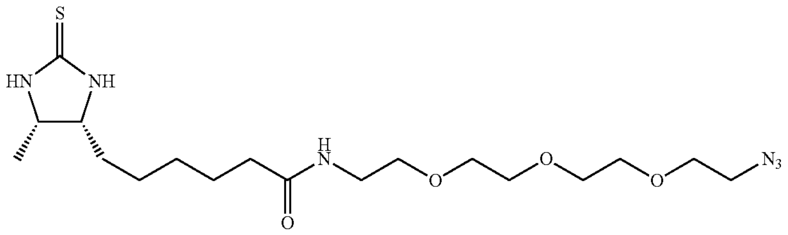 [SMILES: C[C@@H]1NC(=S)N[C@@H]1CCCCCC(=O)NCCOCCOCCOCCN=[N+]=[N-]] |
| 28 | 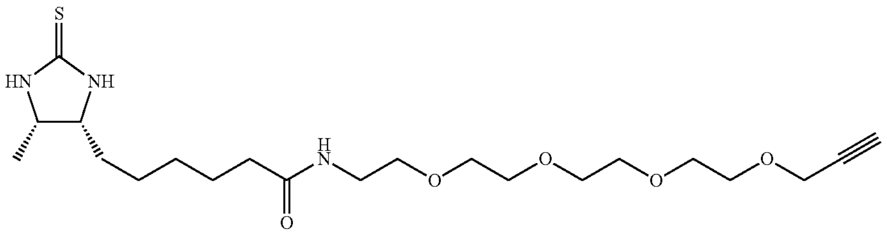 [SMILES: C#CCOCCOCCOCCOCCNC(=O)CCCCC[C@H]1NC(=S)N[C@H]1C] |

TABLE 3-continued
| Nonlimiting exemplary biotin derivative structures | |
|---|---|
| 118 | 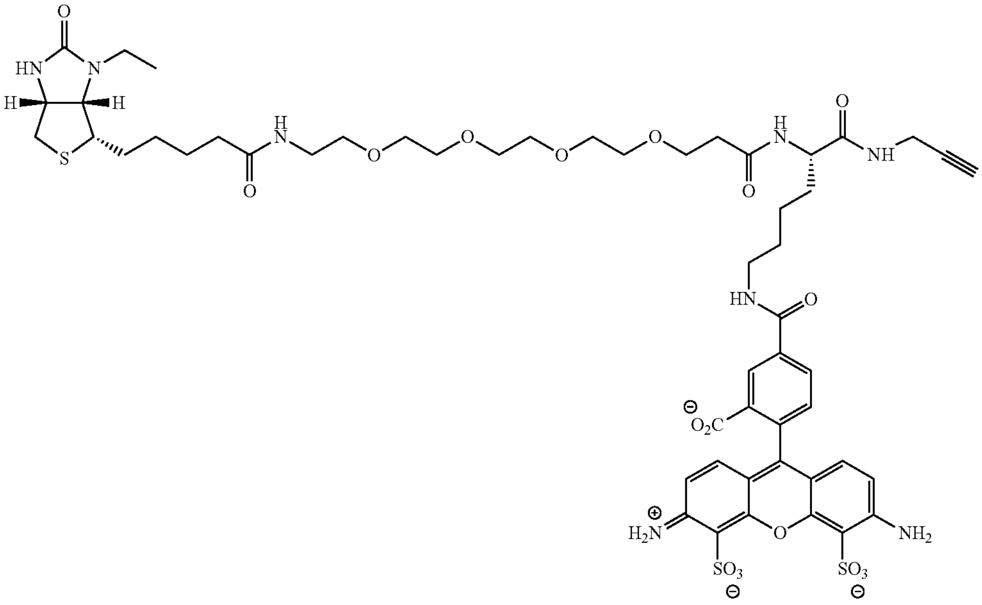 |
| 119 | 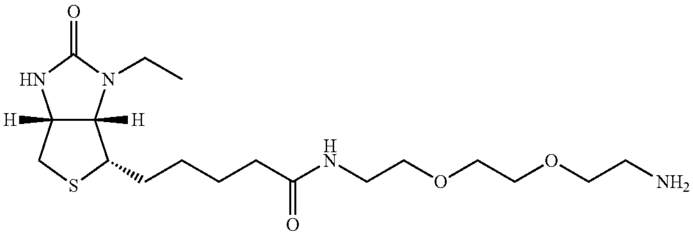 [SMILES: CCN1C(=O)N[C@H]2CS[C@@H](CCCCC(=O)NCCOCCOCCN)[C@H]21] |
TABLE 4
| Nonlimiting exemplary biotin derivative structures | |
|---|---|
| 88 | 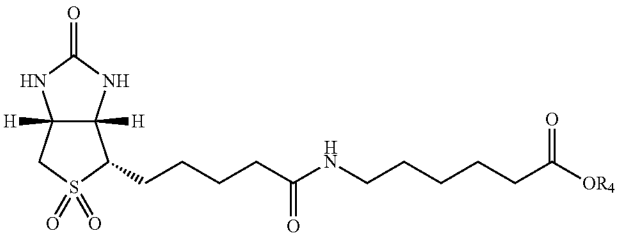 |
| 89 | 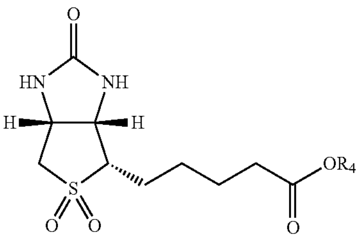 |

TABLE 4-continued
| Nonlimiting exemplary biotin derivative structures | |
|---|---|
| 90 | 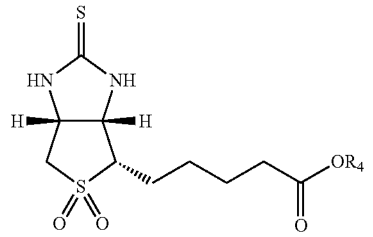 |
| 91 | 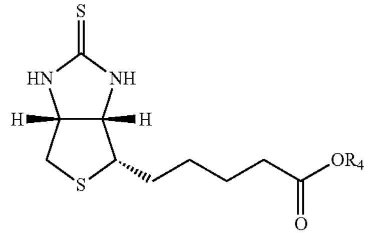 |
| 92 | 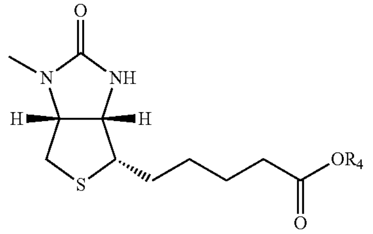 |
| 93 | 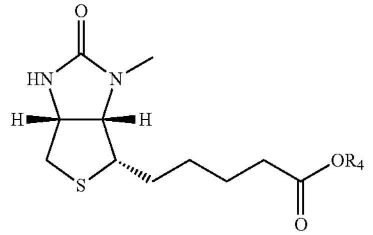 |
| 115 | 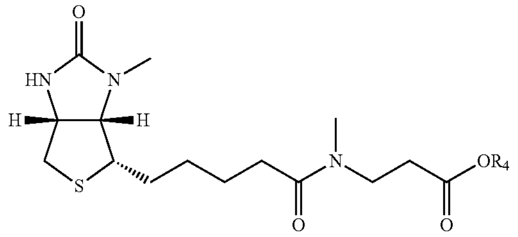 |
| 116 | 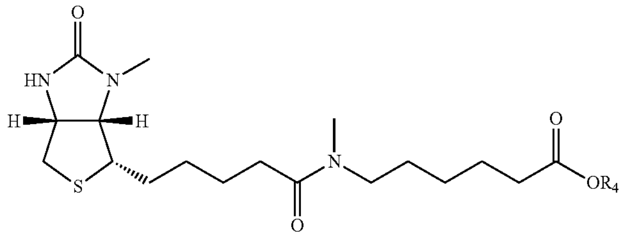 |

TABLE 4-continued
| Nonlimiting exemplary biotin derivative structures | |
|---|---|
| 94 | 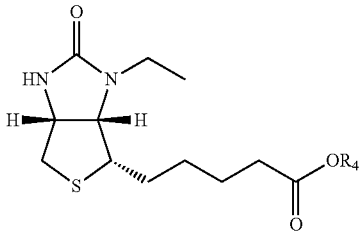 |
| 95 | 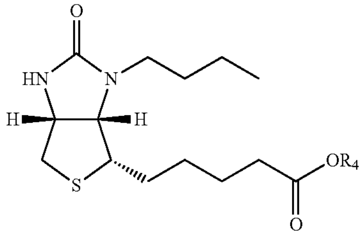 |
| 96 | 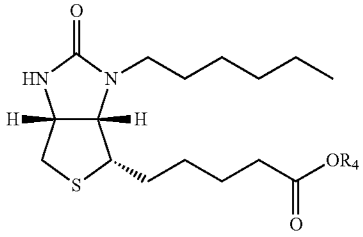 |
| 97 | 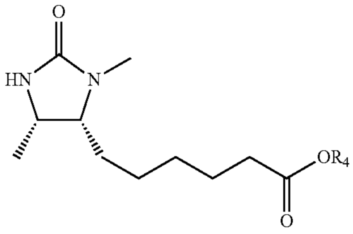 |
| 98 | 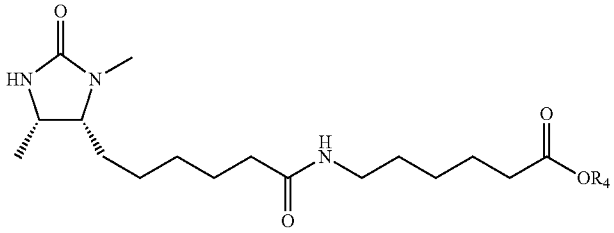 |
| 99 | 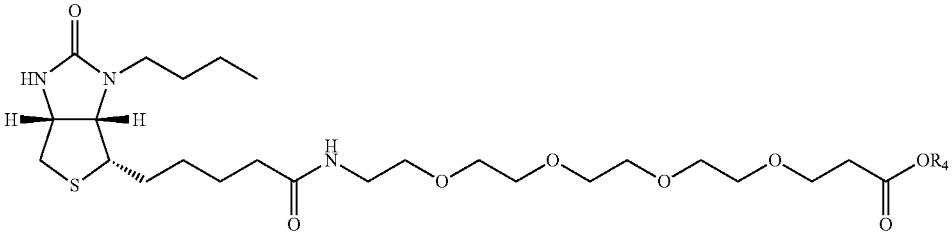 |

TABLE 4-continued
| Nonlimiting exemplary biotin derivative structures | |
|---|---|
| 100 | 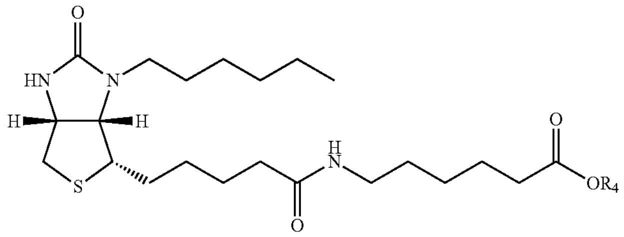 |
| 101 | 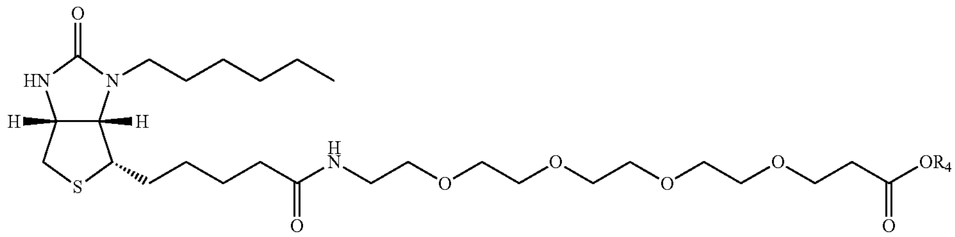 |
| 102 | 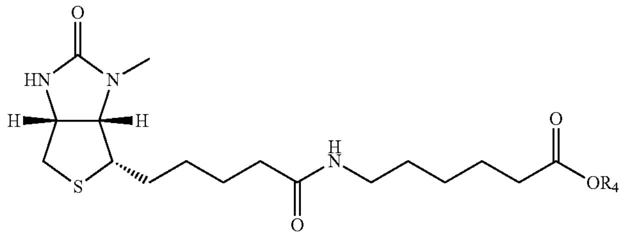 |
| 103 | 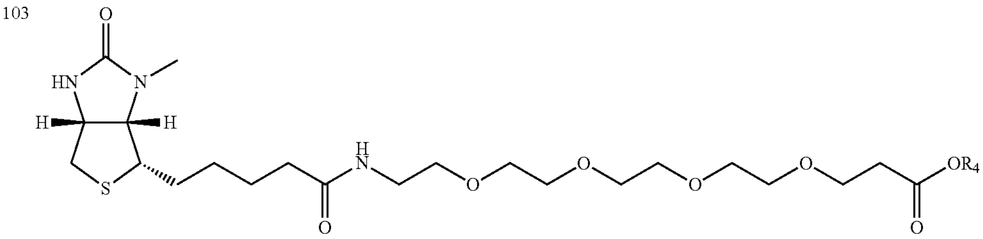 |
| 104 | 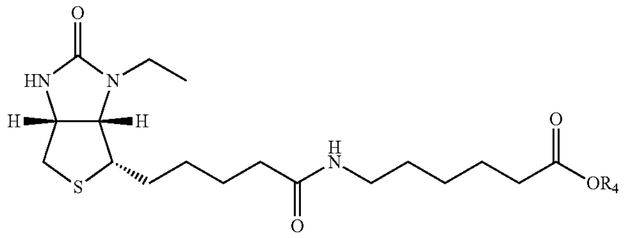 |
| 105 | 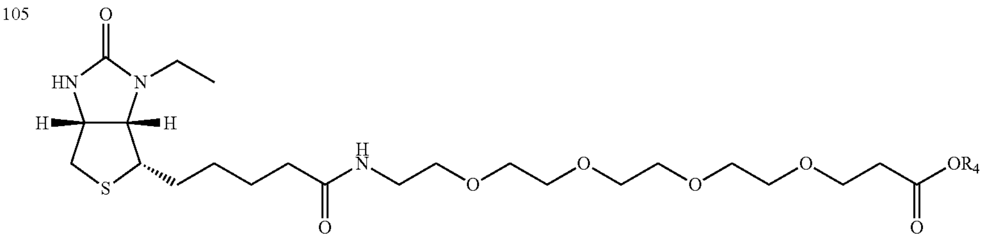 |

TABLE 4-continued
| Nonlimiting exemplary biotin derivative structures | |
|---|---|
| 106 | 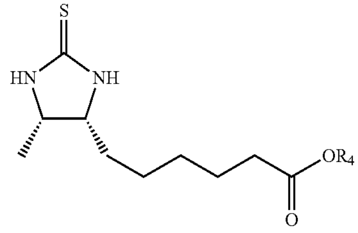 |
| 107 | 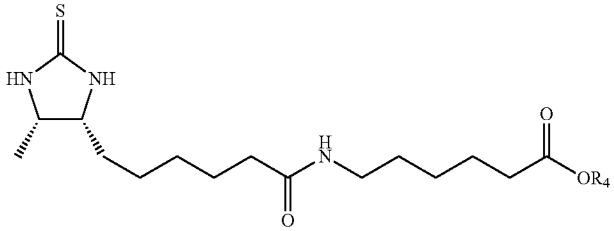 |
| 108 | 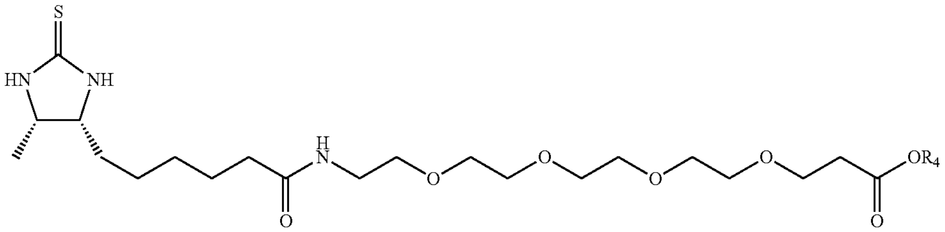 |
| 109 | 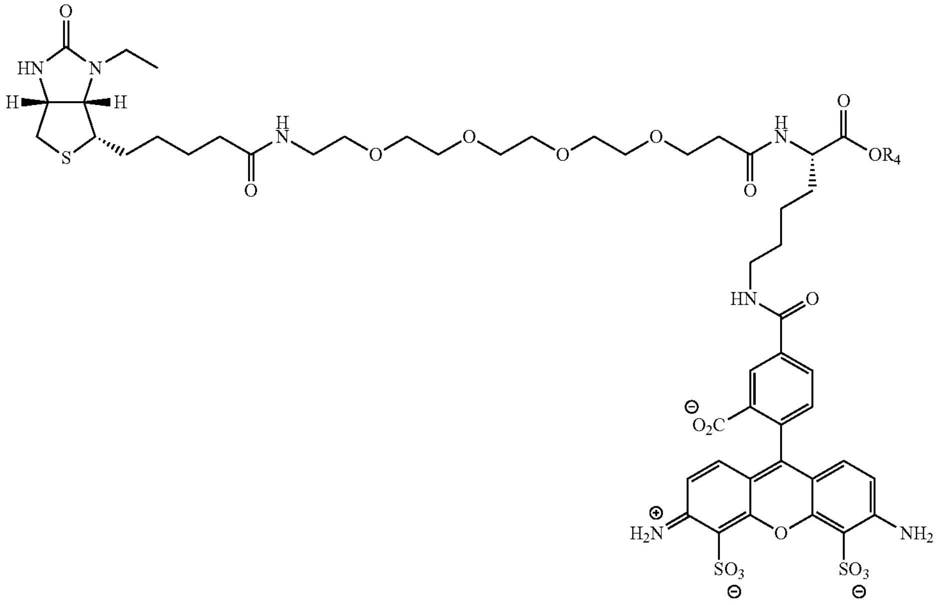 |

TABLE 4-continued

| Nonlimiting exemplary biotin derivative structures |
| --- |
| 110 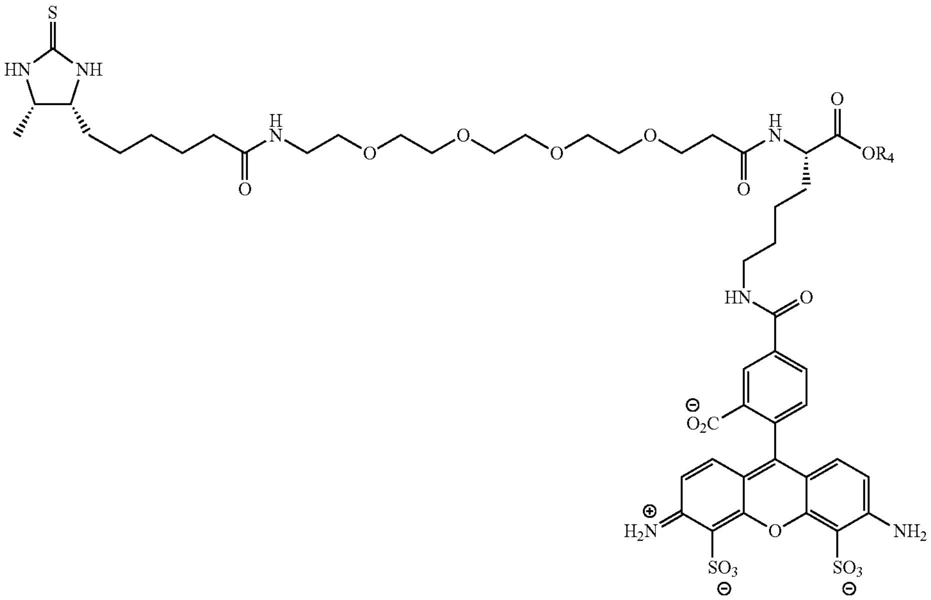 |

In some embodiments, $R_3$ is selected from a protein, a peptide, an amino acid, a dextran, a monosaccharide, a disaccharide, a trisaccharide, an oligosaccharide, a polysaccharide, a hormone, a lipopolysaccharide, a nucleotide, an oligonucleotide, a small molecule, a cell, a microplate, and a microparticle. In some embodiments, a protein $R_3$ group is an antibody. Such antibodies may be of any species, class, or subtype, and include chimeric antibodies, humanized antibodies, antibody fragments, such as Fab, Fab', $F(ab')_2$, Fv, scFv, single domain antibodies (sdAbs), etc.

In some embodiments, $R_3$ is —$OR_4$, wherein $R_4$ is selected from H and a derivative group. In some embodiments, $R_4$ comprises 1 to 8 carbon atoms, 1 to 6 carbon atoms, or 1 to 3 carbon atoms. In some embodiments, $R_4$ is methyl ($CH_3$). In some embodiments, L is absent and $R_3$ is —$OR_4$, wherein $R_4$ is defined as above. See nonlimiting exemplary structures in Table 4.

Exemplary Methods of Synthesizing Biotin Derivatives

In some embodiments, methods of synthesizing biotin derivatives of Formulae I to VI are provided. Nonlimiting exemplary methods of synthesizing biotin derivatives of Formulae I to VI are described herein, e.g., in Examples 1 to 11.

In some embodiments, a method of synthesizing biotin derivative 67 is provided.

67

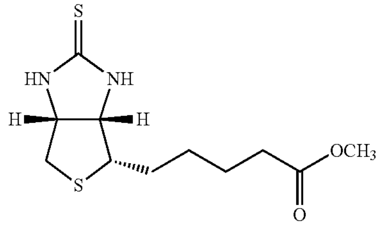

In some embodiments, the method comprises the step of reacting biotin methyl ester with Lawesson's reagent which has the structure:

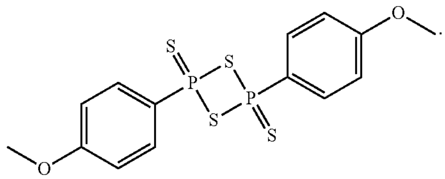

In some embodiments, the reaction is carried out in an organic solvent, such as xylene.

In some embodiments, the ring sulfur atom in biotin derivative 67 is oxidized to sulfone using, e.g., hydrogen peroxide or meta-chloroperoxybenzoic acid (mCPBA) to make biotin derivative 68.

68

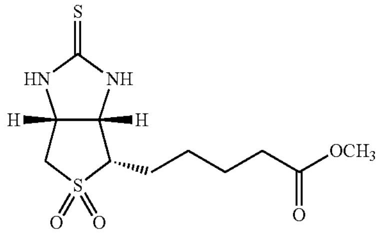

In some embodiments, methods of synthesizing biotin derivatives having the structure:

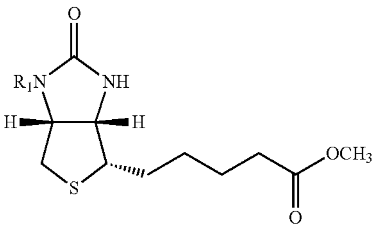

wherein $R_1$ is a derivative group, is provided. In some embodiments, the method comprises reacting biotin methyl ester with a secondary amine-reactive derivative group.

The term "secondary amine-reactive derivative group," as used herein refers to a derivative group comprising a chemical moiety that facilitates attachment of the derivative group to a secondary amine. In some embodiments, the chemical moiety that facilitates attachment of the derivative group to a secondary amine is a leaving group. Nonlimiting exemplary secondary amine-reactive derivative groups include iodoalkyls, bromoalkyls, chloroalkyls, and alkyl chloroformates. One skilled in the art can select a suitable secondary amine-reactive derivative group according to the derivative group to be attached and the particular application.

In some embodiments, methods of synthesizing biotin derivatives having the structure:

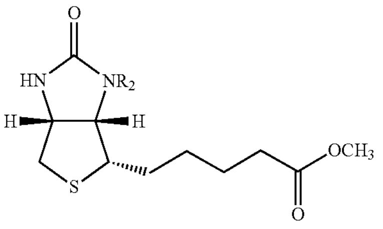

wherein $R_2$ is a derivative group, are provided. In some embodiments, the method comprises reacting biotin methyl ester with a secondary amine-reactive protecting group. In some embodiments, the method further comprises reacting the product (i.e., a biotin methyl ester comprising a protecting group on the nitrogen at the 5 position) with a secondary amine-reactive derivative group. In some embodiments, the method further comprises removing the protecting group.

The term "secondary amine-reactive protecting group," as used herein refers to a protecting group comprising a chemical moiety that facilitates attachment of the protecting group to a secondary amine. In some embodiments, the chemical moiety that facilitates attachment of the protecting group to a secondary amine is a leaving group. As used herein, the term "protecting group" refers to a chemical moiety that prevents a reactive group, such as a secondary amine, from reacting with a reactive species in a mixture, wherein the protecting group can be removed under conditions that do not otherwise alter the biotin derivative to which it is attached. Nonlimiting exemplary secondary amine-reactive protecting groups include dimethoxytrityl chloride (DMTr-Cl), trityl chloride (Trt-Cl), benzyl chloroformate (Cbz-Cl), and allyl chloroformate (Aloc-Cl). One skilled in the art can select a suitable secondary amine-reactive protecting group for a particular application.

In some embodiments, methods of synthesizing biotin derivatives having the structure:

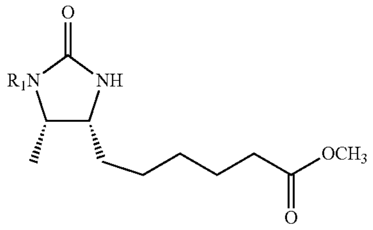

wherein $R_1$ is a derivative group, are provided. In some embodiments, the method comprises reacting desthiobiotin methyl ester with a secondary amine-reactive derivative group.

In some embodiments, methods of synthesizing biotin derivatives having the structure:

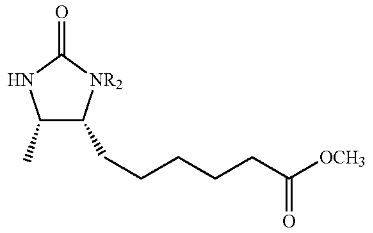

wherein $R_2$ is a derivative group, are provided. In some embodiments, the method comprises reacting desthiobiotin methyl ester with a secondary amine-reactive protecting group. In some embodiments, the method further comprises reacting the product (i.e., a desthiobiotin methyl ester comprising a protecting group on the nitrogen at the 5 position) with a secondary amine-reactive derivative group. In some embodiments, the method further comprises removing the protecting group.

In some embodiments, a method of synthesizing biotin derivative 79 is provided.

79

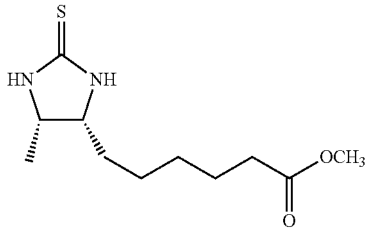

In some embodiments, the method comprises reacting desthiobiotin methyl ester with Lawesson's reagent.

In some embodiments, a methyl ester of a biotin derivative is treated with a base, such as NaOH, to produce the carboxylic acid of the biotin derivative. In some embodiments, the carboxylic acid of the biotin derivative is modified with a reactive group, such as an N-hydroxysuccinimide (NHS) ester, by reacting the carboxylic acid with a carboxylic acid-modifying reactive group.

A "carboxylic acid-modifying reactive group," as used herein, refers to a reactive group comprising a chemical moiety that facilitates attachment of the reactive group to a carboxylic acid. Nonlimiting exemplary carboxylic acid-modifying reactive groups include:

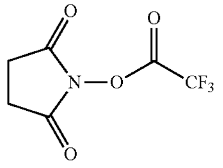 [SMILES: O=C1CCC(=O)N1OC(=O)C(F)(F)F]

2,5-dioxopyrrolidin-1-yl 2,2,2-trifluoroacetate;

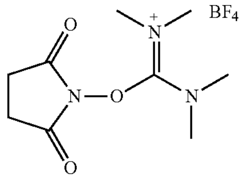

2-(2,5-dioxopyrrolidin-1-yl)-1,1,3,3-tetramethylisouronium tetrafluoroborate;

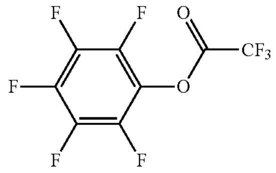 [SMILES: O=C(Oc1c(F)c(F)c(F)c(F)c1F)C(F)(F)F]

perfluorophenyl 2,2,2-trifluoroacetate; and

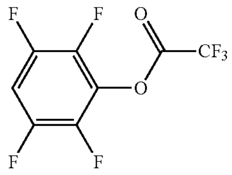 [SMILES: O=C(Oc1c(F)c(F)cc(F)c1F)C(F)(F)F]

2,3,5,6-tetrafluorophenyl 2,2,2-trifluoroacetate.

In some embodiments, a suitable linker can be incorporated into a biotin derivative by reacting a biotin derivative comprising an NHS ester with a linker group comprising a primary amine. For example, in some embodiments, a polyethylene glycol linker can be added to a biotin derivative by reacting the NHS ester of the biotin derivative with:

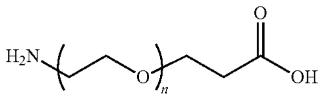

wherein n is an integer from 0 to 20. The carboxylic acid on the resulting biotin derivative may, in some embodiments, be modified with a reactive group as described above. Alternatively, a linker that comprises a primary amine at one location and a reactive group at another location may be reacted with a biotin derivative comprising an NHS ester in order to produce a biotin derivative comprising a linker and a reactive group.

In some embodiments, a reactive group on a biotin derivative is used to link the biotin derivative to a moiety selected from a protein, a peptide, an amino acid, a dextran, a monosaccharide, a disaccharide, a trisaccharide, an oligosaccharide, a polysaccharide, a hormone, a lipopolysaccharide, a nucleotide, an oligonucleotide, a small molecule, a cell, a microplate, and a microparticle (once linked, the molecule is still referred to as a "biotin derivative"). Many methods of using reactive groups to link compounds to such moieties are known in the art. Further, one skilled in the art can select a suitable reactive group depending on the moiety that will be linked to the biotin derivative. For example, in some embodiments, an NHS ester reactive group may be used to link a biotin derivative to a moiety comprising a primary amine (such as a peptide, protein, antibody, etc.). In some embodiments, an azide reactive group may be used to link a biotin derivative to a moiety comprising an alkyne by click chemistry. In some embodiments, an alkyne reactive group may be used to link a biotin derivative to a moiety comprising an azide by click chemistry.

In some embodiments, a linker of a biotin derivative comprises a detectable moiety. A nonlimiting exemplary method of attaching a detectable moiety to a linker group of a biotin derivative is shown in Example 9.

One skilled in the art can synthesize biotin derivatives of Formulae I to VI using the methods and reagents discussed herein, and/or the methods and reagents known in the art. It is within the skill in the art to select suitable reagents, reaction conditions, solvents, etc., for making a particular biotin derivative of any one of Formulae I to VI.

Exemplary Compositions Comprising Biotin Derivatives

In some embodiments, compositions comprising one or more biotin derivatives are provided. In some embodiments, a composition comprises one or more biotin derivatives in a suitable solvent. Solvents include, but are not limited to, aqueous solvents, nonaqueous solvents, and aqueous/nonaqueous solvent systems. Nonlimiting exemplary solvents include water, methanol, ethanol, dimethylsulfoxide (DMSO), dimethylformamide (DMF), dimethylacetamide, and N-methylpyrrolidinone (NMP). In some embodiments, a composition comprises one or more salts and/or one or more buffering agents. Many salts and buffering agents are known in the art. One skilled in the art can select a suitable solvent, one or more suitable salts, and/or one or more suitable buffering agents according to the intended application.

In some embodiments, a composition comprising one or more biotin derivatives is dry. That is, in some embodiments, the composition does not comprise a solvent, but comprises one or more additional components besides the one or more biotin derivatives. In some embodiments, a dry composition comprising one or more biotin derivatives comprises one or more salts and/or one or more buffering agents. In some embodiments, the dry composition is suitable for reconstitution in a solvent, for example, prior to use.

Exemplary Kits Comprising Biotin Derivatives

In some embodiments, kits comprising one or more biotin derivatives are provided. Such kits may comprise, in some embodiments, at least one composition comprising one or more biotin derivatives. In some embodiments, a composition in a kit is a dry composition, as discussed above. In some embodiments, a composition in a kit comprises a solvent, as discussed above.

In some embodiments, a kit comprises one or more additional components. Nonlimiting exemplary additional components include sample handling devices (such as pipettes, droppers, etc.), containers suitable for use in various instruments (such as cuvettes, microwell plates, etc.), buffers for certain applications (such as reaction buffers, elution buffers, binding buffers, etc.), other reagents (such as biotin for eluting the biotin derivatives, streptavidin-coated solid supports, and reagents to facilitate detection), and instructions for use of the biotin derivatives.

Exemplary Methods of Using Biotin Derivatives

In some embodiments, methods of immobilizing a biotin derivative of any one of Formulae I to VI are provided. In some embodiments, such methods comprise contacting the biotin derivative with a solid support that comprises a biotin-binding moiety. In some embodiments, methods further comprise eluting the biotin derivative of any one of Formulae I to VI from the biotin-binding moiety.

A "biotin-binding moiety," as used herein, refers to a moiety that specifically binds biotin. Nonlimiting exemplary biotin-binding moieties include, but are not limited to, avidin, streptavidin, and derivatives of avidin and streptavidin that specifically bind biotin. Nonlimiting exemplary derivatives of avidin and streptavidin include avidins and streptavidins with one or more amino acid substitutions, deletions, and/or modifications. Nonlimiting exemplary such derivatives are described, e.g., in U.S. Publication No. 2008/0255004; PCT Publication No. WO 01/05977; U.S. Pat. Nos. 6,022,951; 6,391,571; 6,312,916; 6,417,331; 6,165,750; 6,156,493; 5,973,124; and 5,168,049.

In some embodiments, where later dissociation may be desired, a biotin derivative selected from the biotin derivatives of Formulae I to VI has an affinity for a biotin-binding moiety that is less than the affinity of biotin for the biotin-binding moiety. Thus, in some embodiments, a biotin derivative selected from the biotin derivatives of Formulae I to VI binds a biotin-binding moiety with a $K_D$ of greater than $1\times10^{-13}$ M. In some embodiments, a biotin derivative selected from the biotin derivatives of Formulae I to VI binds a biotin-binding moiety with a $K_D$ of greater than $1\times10^{-13}$ M. In some embodiments, a biotin derivative selected from the biotin derivatives of Formulae I to VI binds a biotin-binding moiety with a $K_D$ of between $1\times10^{-13}$ M and $1\times10^{-8}$ M, between $1\times10^{-12}$ M and $1\times10^{-9}$ M, or between $1\times10^{-11}$ M and $1\times10^{-9}$ M, between $10^{-13}$ M to $10^{-4}$ M, between $10^{-12}$ M to $10^{-4}$ M, between $10^{-11}$ M to $10^{-4}$ M, between $10^{-10}$ M to $10^{-4}$ M, between $10^{-9}$ M to $10^{-4}$ M, between $10^{-8}$ M to $10^{-4}$ M, between $10^{-7}$ M to $10^{-4}$ M, or between $10^{-6}$ M to $10^{-4}$ M.

In some embodiments, where later dissociation is not desired, a biotin derivative selected from the biotin derivatives of Formulae I to VI has an affinity for a biotin-binding moiety that is less than or equal to $1\times10^{-13}$ M. Thus, in some embodiments, a biotin derivative selected from the biotin derivatives of Formulae I to VI binds a biotin-binding moiety with a $K_D$ of between about $1\times10^{-13}$ M to about $1\times10^{-15}$ M.

Nonlimiting exemplary solid supports include polymers (such as agarose, sepharose, cellulose, nitrocellulose, alginate, Teflon, latex, acrylamide, nylon, plastic, polystyrene, silicone, etc.), glass, silica, ceramics, and metals. Such solid supports may take any form, such as particles (including microparticles), sheets, dip-sticks, gels, filters, membranes, microfiber strips, tubes, wells, plates (such as microplates, including 6-well plates, 24-well plates, 96-well plates, 384-well plates, etc.), fibers, capillaries, combs, pipette tips, microarray chips, etc. In some embodiments, the biotin-binding moiety is associated with the surface of a solid support. In some embodiments, the surface of the solid support comprises an irregular surface, such as a porous, particulate, fibrous, webbed, or sintered surface.

In some embodiments, a solid support is selected from a microplate, a microarray chip, and a microparticle. In some embodiments, a solid support is at least partially composed of a polymer. In some embodiments, a microparticle solid support comprises monodisperse or polydisperse spherical beads. Monodisperse microparticles are substantially uniform in size (i.e., they have a diameter standard deviation of less than 5%), while polydisperse microparticles vary in size. In some embodiments, microparticles are composed of the same polymer throughout, or are core-shell polymers, in which the core of the microparticle is composed of one polymer, and the outer layer (or "shell") is composed of another. In some embodiments, microparticles are magnetic.

In some embodiments, a biotin-binding moiety is attached to a solid support through an amino or sulfhydryl group of the biotin-binding moiety. In some such embodiments, the surface of the solid support comprises a group capable of reacting with a free amine or sulfhydryl group. Nonlimiting exemplary such groups include carboxy, active halogen, activated 2-substituted ethylsulfonyl, activated 2-substituted ethyl carbonyl, active ester, vinylsulfonyl, vinylcarbonyl, aldehyde, epoxy, etc. Some such groups may require the use of an additional reactant to render the group capable of reacting with a free amine or sulfhydryl group. Nonlimiting exemplary additional reactants include cyanogen bromide, carbonyldiimidazole, glutaraldehyde, hydroxylsuccinimide, tosyl chloride, etc.

Many solid supports are known in the art, and one skilled in the art can select a suitable solid support according to the intended application. Similarly, if the solid support is not commercially available with a biotin-binding moiety attached to its surface, one skilled in the art can select a suitable method of attaching a biotin-binding moiety to a solid surface. Exemplary such methods are described, e.g., in U.S. Publication No. US 2008/022004 A1.

In some embodiments, eluting comprises contacting the immobilized biotin derivative with a displacement molecule. A "displacement molecule" as used herein is a molecule that has an affinity for the biotin-binding moiety that is greater than the affinity of the biotin derivative for the biotin-binding moiety. A nonlimiting example of such a molecule is biotin. The term "biotin" as used herein includes native biotin and non-native biotins, such as biotin methyl ester and biotin multimers, including, but not limited to, biotin dimers and biotin trimers. Nonlimiting exemplary biotins include the nonnative biotins described, e.g., in Wilbur et al., *Bioconjugate Chem.* 8: 819-32 (1997). In some embodiments, a biotin binds to the biotin-binding moiety with a $K_D$ of less than $1\times10^{-14}$ M. In some embodiments, a nonnative biotin is more soluble in aqueous solvents than native biotin. The term "native biotin" as used herein refers to a biotin having the structure:

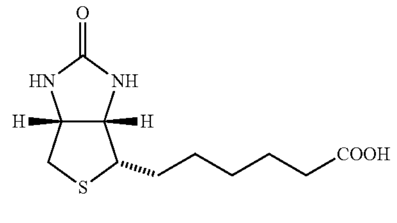 [SMILES: O=C(O)CCCCC[C@@H]1SC[C@@H]2NC(=O)N[C@@H]21]

In some embodiments, eluting comprises exposing the immobilized biotin derivative to concentrations of native biotin or non-native biotins, such as biotin multimers, sufficient to cause release, such as, for example, millimolar (mM) concentration, at room temperature or at 37° C. with mixing.

In some embodiments, the methods described herein are used for the detection, identification, determination, purification, separation, and/or isolation of an entity from a sample. In some embodiments, the entity is attached to a biotin derivative such that it becomes the $R_3$ group in any one of Formulae I to VI. In some embodiments, the entity is selected from a protein, a peptide, an amino acid, a dextran, a monosaccharide, a disaccharide, a trisaccharide, an oligosaccharide, a polysaccharide, a hormone, a lipopolysaccharide, a nucleotide, an oligonucleotide, a small molecule, a cell, or a microparticle. In some embodiments, $R_3$ is a moiety that binds to the entity to be separated from a sample.

In some embodiments, $R_3$ is an activity-based probe, which specifically interacts with a particular entity or class of entities, and, in some embodiments, becomes covalently attached to an entity upon binding. Nonlimiting exemplary activity-based probes are described, e.g., in Bachovchin et al., *Nat. Biotech.* 27: 387-394 (2009); Cravatt et al., *Ann. Rev. Biochem.* 77: 383-414 (2008); Fonović et al., *Curr. Pharmac. Des.* 13: 253-261 (2007); Kato et al., *Nat. Chem. Biol.* 1: 33-38 (2005); Patricelli et al., *Biochem.* 46: 350-358 (2007); Paulick et al., *Curr. Opin. Genet. Dev.* 18: 97-106 (2008); Saghatelian et al., *PNAS* 101: 10000-10005 (2004); Salisbury et al., *J. Am. Chem. Soc.* 130: 2184-2194 (2008); Salisbury et al. *PNAS* 104: 1171-1176 (2007); Wright et al., *Chem. & Biol.* 14: 1043-1051 (2007); Wright et al., *JACS* 131: 10692-10700 (2009); U.S. Pat. No. 6,872,574 B2; and U.S. Publication Nos. US 2009/0252677 A1 and US 2008/0176841 A1.

In some such embodiments, $R_3$ is an antibody that binds an entity in a sample. Thus, in some embodiments, a biotin derivative of any one of Formulae I to VI, wherein $R_3$ is, for example, an antibody or other entity-binding moiety, is used in the described methods to bind to the entity in a sample. The entity may then be detected, identified, determined, purified, separated, and/or isolated as desired.

In some embodiments, the sample is a biological sample. Such biological samples include, but are not limited to, blood and blood fractions and products, saliva, lymph, bile, urine, milk, feces, spinal fluid, semen, cells, proteins, cells comprising target proteins therein or thereon, cell extracts, fluid preparations of tissue samples, organ biopsy samples, etc. Other exemplary samples include, but are not limited to, water samples, fluid preparations of soil samples, food samples, etc.

In some embodiments, the methods described herein are used to detect, identify, determine, purify, separate, and/or isolate cells and/or viruses from a sample. Nonlimiting exemplary cells include prokaryotic and eukaryotic cells, including mammalian cells, non-mammalian animal cells, plant cells, insect cells, fungal cells, yeast cells, protozoa, bacteria, etc. Nonlimiting exemplary viruses include DNA and RNA viruses and retroviruses, etc. In some embodiments, the cells and/or viruses remain viable throughout the method. In some embodiments, the cells or viruses are propagated following separation, purification, and/or isolation using the method. In some embodiments, the cells and/or viruses are considered to have "remained viable" if, following application of the method, at least 75%, at least 80%, at least 85%, or at least 90% of the cells and/or viruses are viable (i.e., capable of propagating and/or carrying out cellular or viral processes).

In some embodiments, binding of the biotin derivative of any one of Formulae I to VI to an entity is used to label the entity, e.g., for detection. In some embodiments, the biotin derivative of any one of Formulae I to VI binds to the entity through the $R_3$ group, which comprises an entity-binding moiety. In some embodiments, the biotin derivative of any one of Formulae I to VI comprises a detectable moiety as part of a linker (or L group). Thus, in some such embodiments, following binding, the entity can be detected by association of the detectable moiety. Such detection may occur with or without (or before or after) purification, separation, and/or isolation of the entity by the methods described herein (such as binding the biotin derivative to a biotin-binding moiety).

As a non-limiting example, a biotin derivative of any one of Formulae I to VI comprising a linker with a detectable moiety and an $R_3$ group that binds to a factor on the surface of a cell may be bound to the cell in a mixture. Following binding, the mixture may be examined under a microscope to detect association of the detectable moiety with cells in the mixture. The cells may then be contacted with a microparticle comprising a biotin-binding moiety on the surface. The biotin-binding moiety may bind to the biotin derivative of any one of Formulae I to VI, resulting in association of the microparticle with the cells in the mixture. The cells may then be separated from the mixture by some property of the microparticles (such as, for example, by magnetic separation or gentle centrifugation). The biotin derivative/biotin-binding moiety interaction may then be interrupted (i.e., using an elution step). The cell will remain associated with the detectable moiety, but not with the microparticle. The cell can then be manipulated as desired, in some embodiments, with the detectable moiety still associated.

The claimed invention is in no way limited to the embodiments exemplified herein. One skilled in the art can envision many additional applications of the described biotin derivatives and methods.

EXAMPLES

The examples discussed below are intended to be purely exemplary of the invention and should not be considered to limit the invention in any way. The examples are not intended to represent that the experiments below are all or the only experiments performed. Efforts have been made to ensure accuracy with respect to numbers used (for example, amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Example 1: Preparation of 2,5-dioxopyrrolidin-1-yl 6-(5-((3aS,4S,6aR)-5,5-dioxido-2-oxohexahydro-1H-thieno[3,4-d]imidazol-4-yl)pentanamido)hexanoate (Biotin Derivative 1)

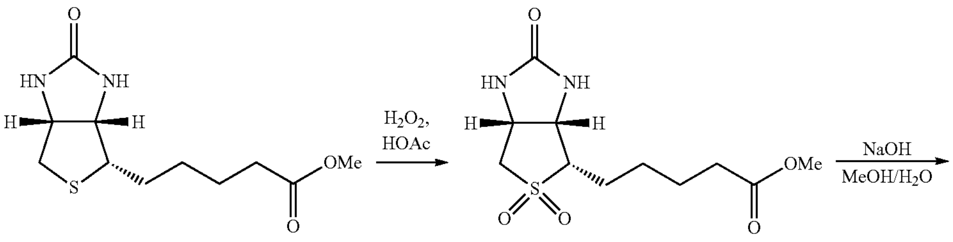

62 63

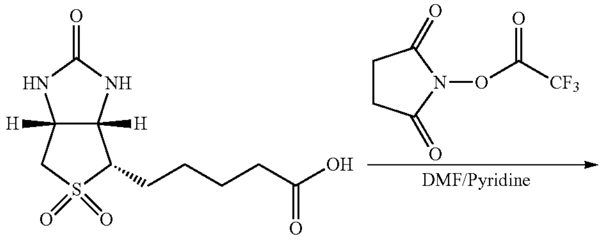

64

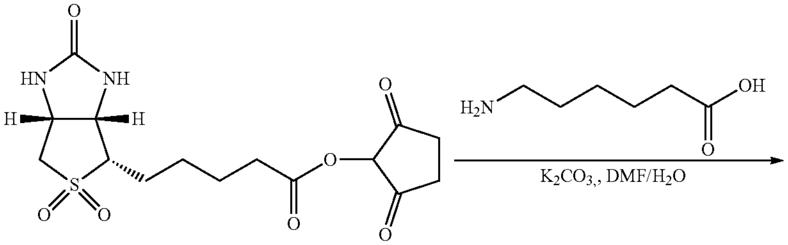

65

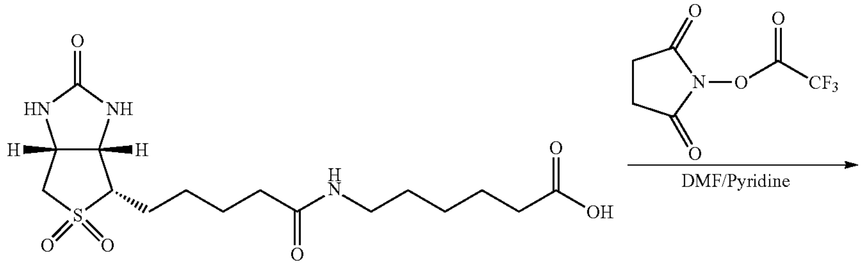

66

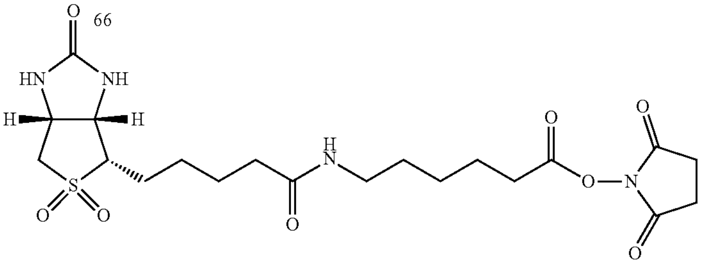

1

Biotin methyl ester 62 was oxidized to sulfone 63 using hydrogen peroxide, and then the methyl ester was hydrolyzed to free acid 64, which was converted to NHS ester 65. The NHS ester 65 was reacted with 6-aminocaproic acid to give 66, which was converted to NHS ester 1.

Example 2: Preparation of 2,5-dioxopyrrolidin-1-yl 5-((3aS,4S,6aR)-5,5-dioxido-2-thioxohexahydro-1H-thieno[3,4-d]imidazol-4-yl)pentanoate (Biotin Derivative 2)

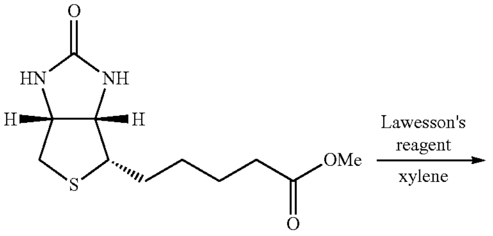

62

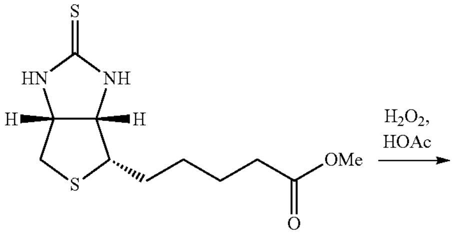

67

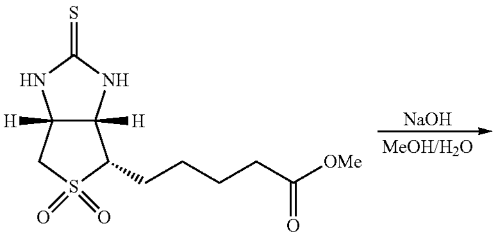

68

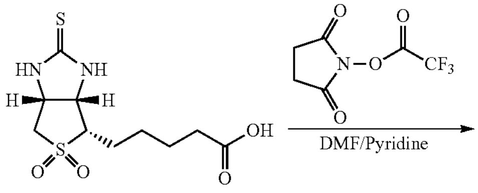

69

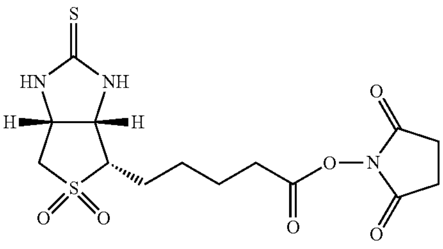

2

Biotin methyl ester 62 was converted to 67 using Lawesson's reagent (2,4-bis(4-methoxyphenyl)-1,3,2,4-dithiadiphosphetane 2,4-disulfide). The methyl ester 67 was oxidized to sulfone 68 using hydrogen peroxide. The methyl ester 68 was hydrolyzed to free acid 69, which was then converted to NHS ester 2.

Example 3: Preparation of 2,5-dioxopyrrolidin-1-yl 5-((3aS,4S,6aR)-2-thioxohexahydro-1H-thieno[3,4-d]imidazol-4-yl)pentanoate (Biotin Derivative 3)

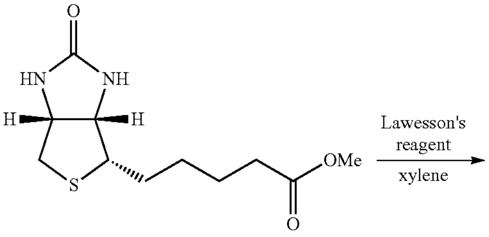

62

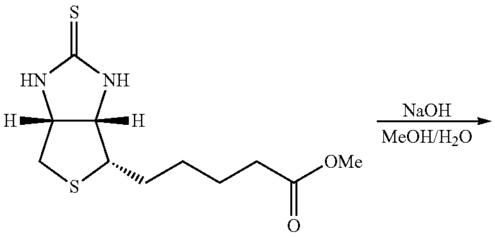

67

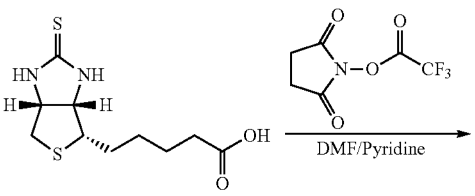

70

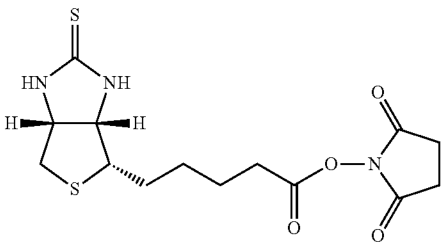

3

Biotin methyl ester 62 was converted to 67 using Lawesson's reagent. The methyl ester 67 was hydrolyzed to free acid 70, which was then converted to NHS ester 3.

Example 4: Preparation of 2,5-dioxopyrrolidin-1-yl 5-((3aS,4S,6aR)-1-methyl-2-oxohexahydro-1H-thieno[3,4-d]imidazol-4-yl)pentanoate (Biotin Derivative 4)

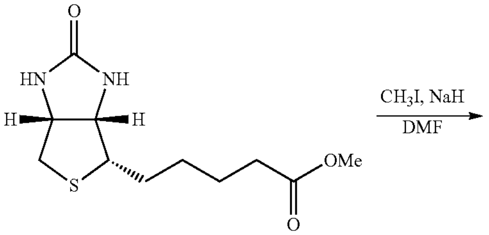

62

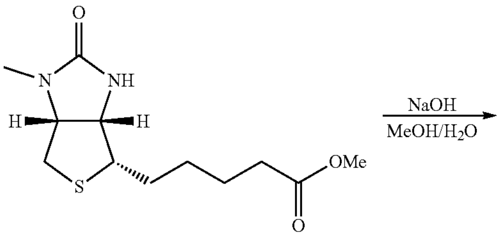

71

-continued

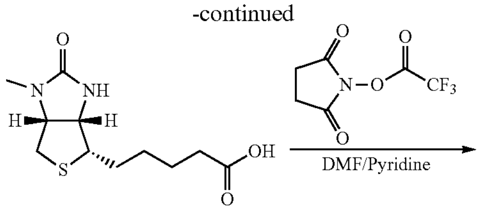

72

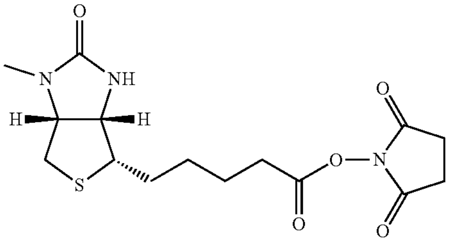

4

Biotin methyl ester 62 was selectively alkylated by iodomethane to give 71. The methyl ester 71 was hydrolyzed to free acid 70, which was then converted to NHS ester 4.

Example 5: Preparation of 2,5-dioxopyrrolidin-1-yl 5-((3aS,4S,6aR)-3-ethyl-2-oxohexahydro-1H-thieno[3,4-d]imidazol-4-yl)pentanoate (Biotin Derivative 6)

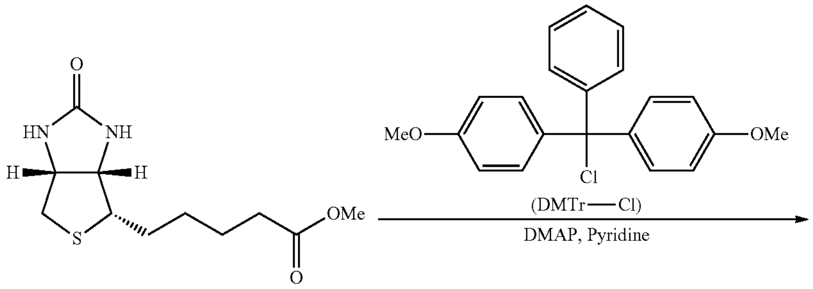

62

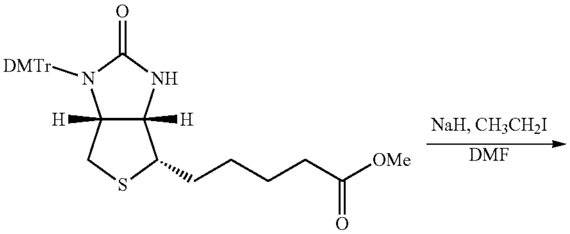

73

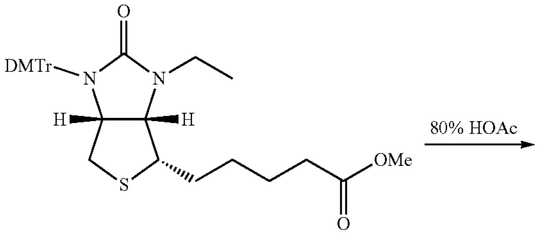

74

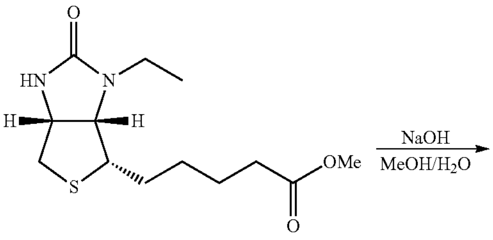

75

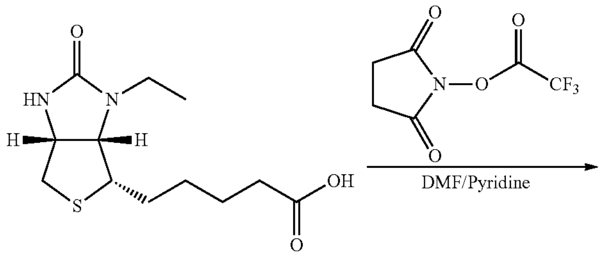

76

-continued

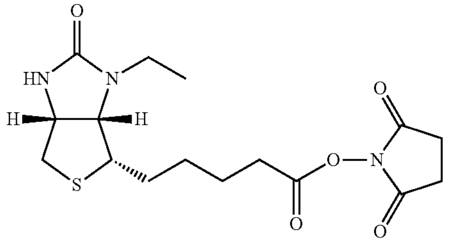

6

Biotin methyl ester 62 was selectively protected by dimethoxytrityl chloride (DMTr-Cl) to give 73, followed by alkylation with iodoethane to yield 74. The DMTr protecting group was cleaved by 80% acetic acid to give 75. The methyl ester 75 was hydrolyzed to free acid 76, which was then converted to NHS ester 6.

Example 6: Preparation of 2,5-dioxopyrrolidin-1-yl 21-((3aS,4S,6aR)-3-ethyl-2-oxohexahydro-1H-thieno[3,4-d] imidazol-4-yl)-17-oxo-4,7,10,13-tetraoxa-16-azahenicosan-1-oate (Biotin Derivative 17)

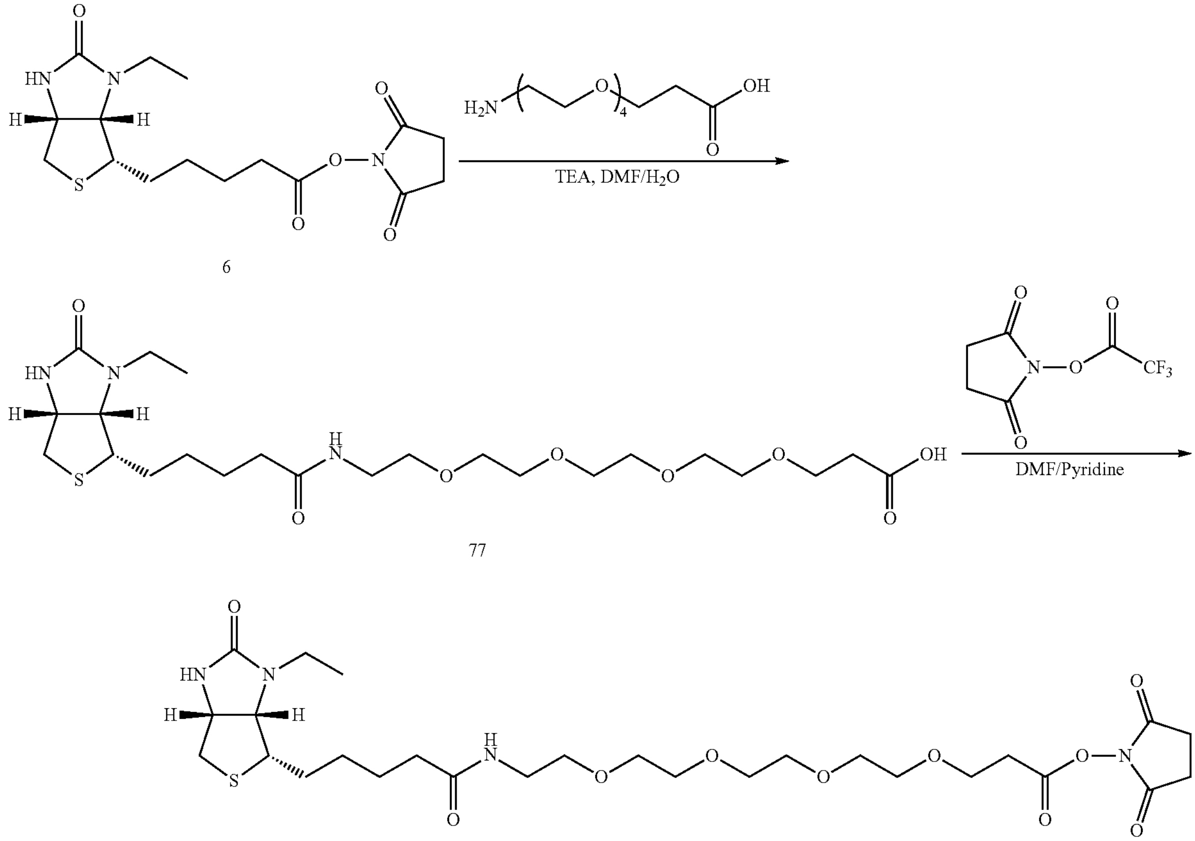

6

77

17

Biotin derivative 6 as prepared above was reacted with amino-$(PEG)_4$-acid to yield 77, which was then converted to NHS ester 17.

Example 7: Preparation of 2,5-dioxopyrrolidin-1-yl 6-((4R,5S)-5-methyl-2-thioxoimidazolidin-4-yl) hexanoate (Biotin Derivative 18)

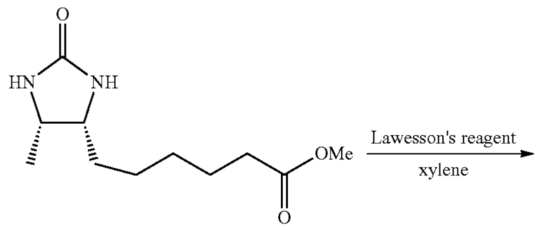

78

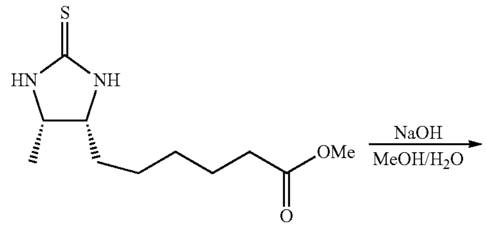

79

-continued

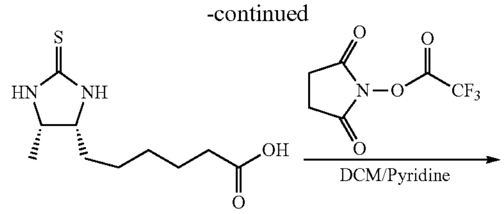

80

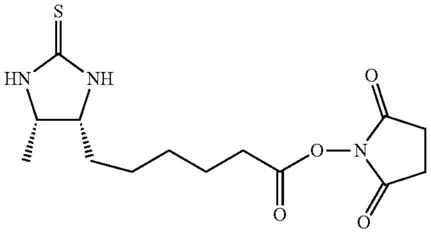

18

DSB methyl ester 78 was converted to 79 by Lawesson's reagent. The methyl ester 79 was hydrolyzed to free acid 80, which was then converted to NHS ester 18.

Example 8: Preparation of 2,5-dioxopyrrolidin-1-yl 22-((4R,5S)-5-methyl-2-thioxoimidazolidin-4-yl)-17-oxo-4,7,10,13-tetraoxa-16-azadocosan-1-oate (Biotin Derivative 20)

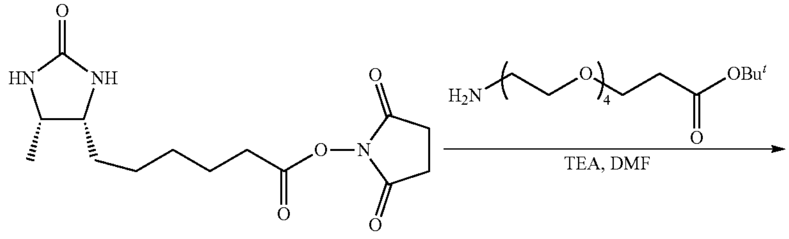

81

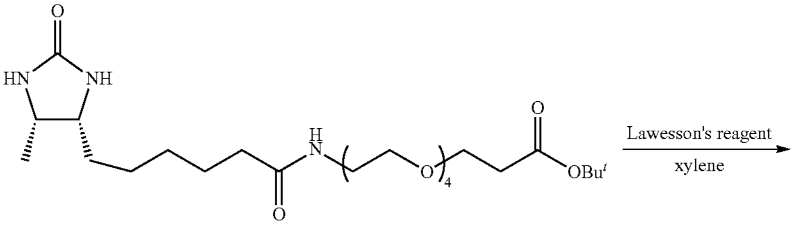

82

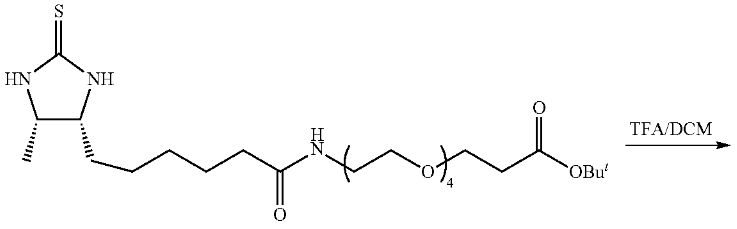

83

-continued

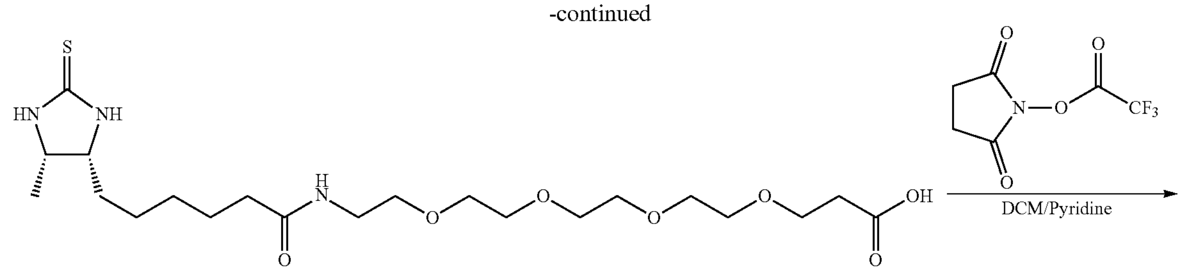

84

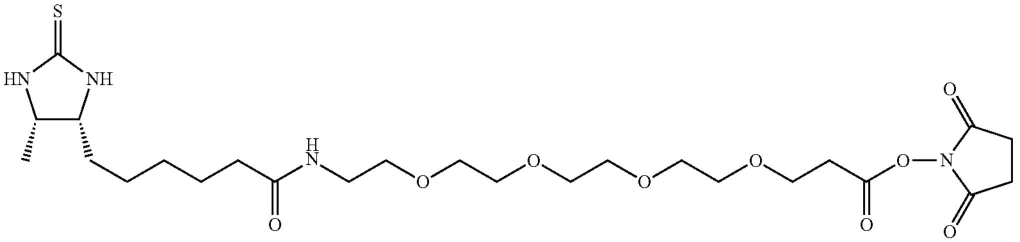

20

DSB NHS ester 81 was reacted with amino-$(PEG)_4$-acid tert-butyl ester to yield 82, which was converted to 83 by Lawesson's reagent. The tert-butyl ester was deprotected by TFA to give free acid 84, which was then converted to NHS ester 20.

Example 9: Preparation of 2-(6-amino-3-iminio-4,5-disulfonato-3H-xanthen-9-yl)-5-(((S)-23-(((2,5-dioxopyrrolidin-1-yl)oxy)carbonyl)-1-((3aS,4S,6aR)-3-ethyl-2-oxohexahydro-1H-thieno[3,4-d] imidazol-4-yl)-5,21-dioxo-9,12,15,18-tetraoxa-6,22-diazaheptacosan-27-yl)carbamoyl)benzoate (Biotin Derivative 21)

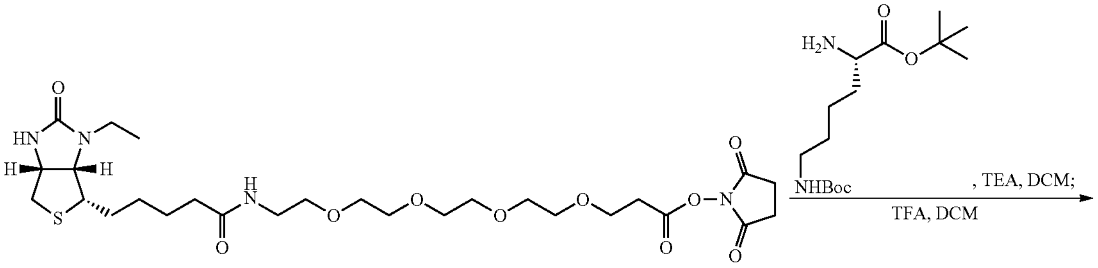

17

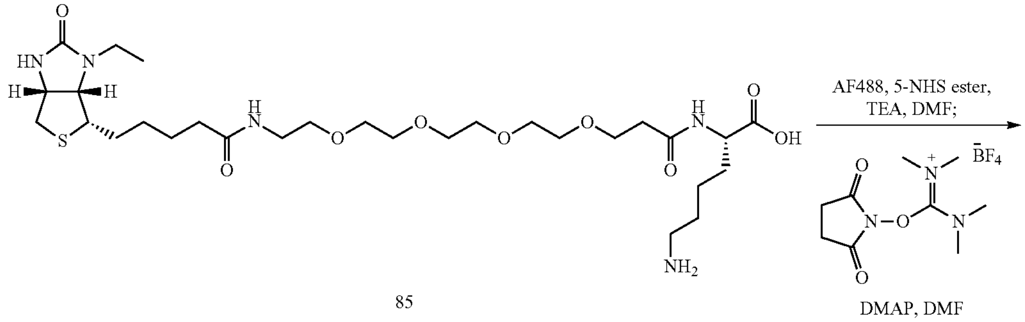

85

-continued

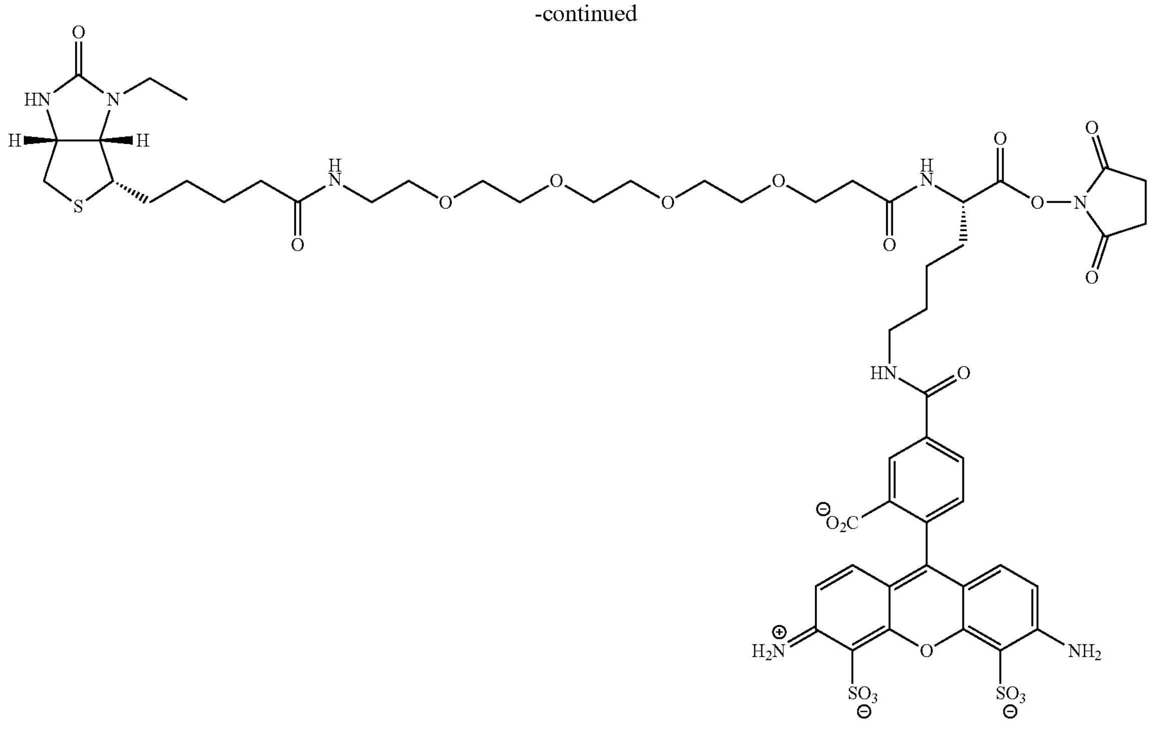

21

Biotin derivative 17 as prepared above was reacted with L-Lys(Boc)-O$^t$Bu, followed by deprotection by TFA to give biotin derivative 85. Then biotin derivative 85 was reacted with AF488, 5-NHS ester, followed by conversion to NHS ester 21.

Example 10: Preparation of N-(2-(2-(2-(2-azidoethoxy)ethoxy)ethoxy)ethyl)-5-((3aS,4S,6aR)-3-ethyl-2-oxohexahydro-1H-thieno[3,4-d]imidazol-4-yl) pentanamide (Biotin Derivative 23)

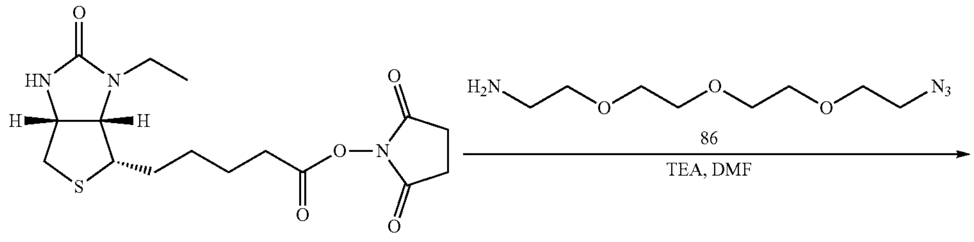

6

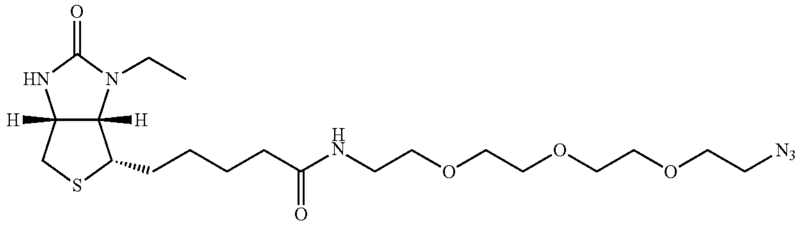

23

Biotin derivative 6 as prepared above was reacted with compound 86 to give biotin derivative 23.

Example 11: Preparation of 5-((3aS,4S,6aR)-3-ethyl-2-oxohexahydro-1H-thieno[3,4-d]imidazol-4-yl)-N-(3,6,9,12-tetraoxapentadec-14-ynyl)pentanamide (Biotin Derivative 24)

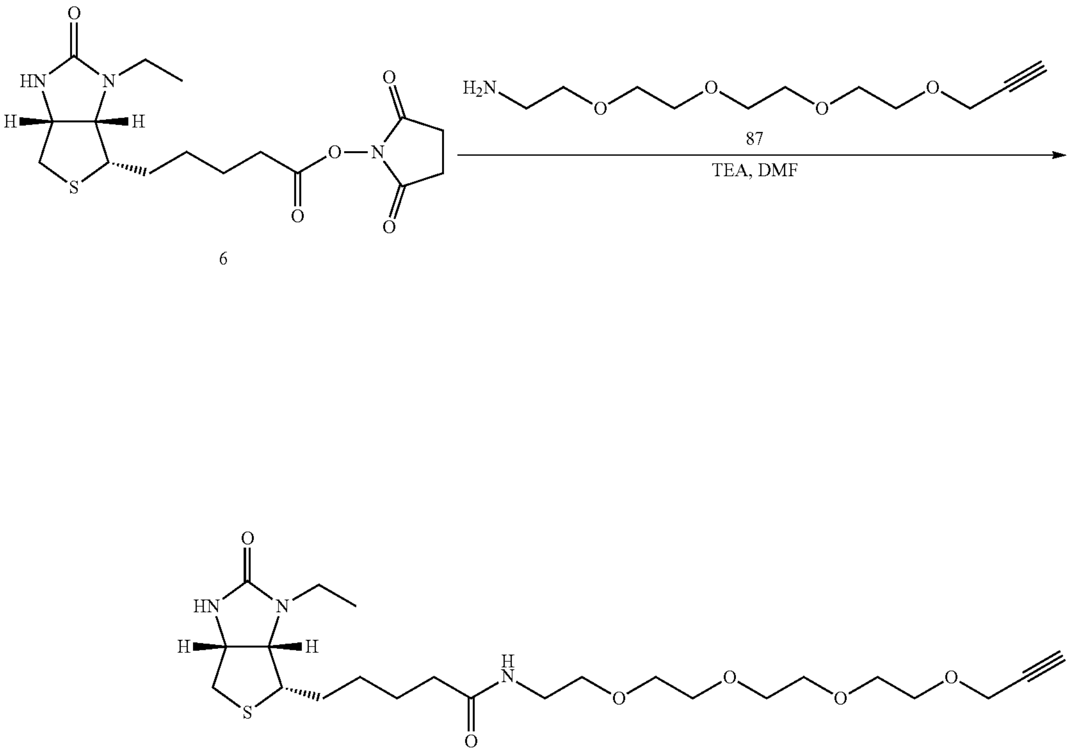

24

Biotin derivative 6 as prepared above was reacted with compound 87 to give biotin derivative 24.

Example 12: Preparation of Antibody-Linked Biotin Derivatives

A series of biotin derivative conjugates of goat anti-mouse IgG (GAM) were prepared by standard methods. See, e.g., Haugland et al., Meth. Mol. Biol. 45: 205 (1995). The goat anti-mouse antibody was labeled with Alexa Fluor® 488 Dye (Invitrogen) prior to conjugation to the biotin derivatives to facilitate later detection. An exemplary method for protein conjugation with succinimidyl esters of the invention is as follows. One skilled in the art can vary the ratios of biotin derivative to protein, protein concentration, time, temperature, buffer composition, etc. while making a desired conjugate. A solution of protein is prepared at ~10 mg/mL in 0.1 M sodium bicarbonate. The biotin derivative is dissolved in a suitable solvent such as DMF or DMSO at ~10 mg/mL. Predetermined amounts of the biotin derivative is added to the protein solution with stirring. A molar ratio of 20 equivalents of biotin derivative to 1 equivalent of protein is typical, though the optimal amount varies with the particular biotin derivative, and can be determined by one skilled in the art. The reaction mixture is incubated at room temperature for one hour or on ice for several hours. The biotin derivative-protein conjugate is typically separated from free unreacted reagents by size-exclusion chromatography, such as on a Bio-Rad P-30 resin equilibrated with phosphate-buffer saline (PBS).

Antibody-linked biotin derivatives are referred to as "1-Ab," "2-Ab," "3-Ab," etc. The structures of the antibody-linked biotin derivatives are shown below in Table 5.

Example 13: Analysis of Capture and Detachment Efficiency of Antibody-Linked Biotin Derivatives One-half nil of antibody-linked biotin derivative (0.1 mg/ml in PBS buffer) was incubated with 100 μl of M280 Streptavidin Dynabeads (10 mg/ml) and mixed at RT for 10 minutes. The tube was placed on a magnet for 1 minute. The supernatant was carefully removed. The tube was then removed from the magnet, and 0.5 ml PBS buffer was added, and the beads were resuspended by gentle pipetting 5 times. The tube was placed on the magnet for 1 minute. The supernatant was carefully removed. The PBS buffer wash was repeated twice. The tube was removed from the magnet and the beads were carefully resuspended in 0.5 nil of fresh elution buffer containing 5 mM biotin or 5 mM bis-biotin in PBS, and mixed at room temperature for 5 minutes. The tube was placed on the magnet for 1 minute. The supernatant was carefully removed. The efficiencies of capture and detachment were measured by the fluorescence intensity of the supernatant.

The results of that experiment are shown in Table 5.
TABLE 5
| Capture and detachment efficiency of antibody-lined biotin derivatives | | |
|---|---|---|
| Biotin derivative | Capture | Detachment |
| 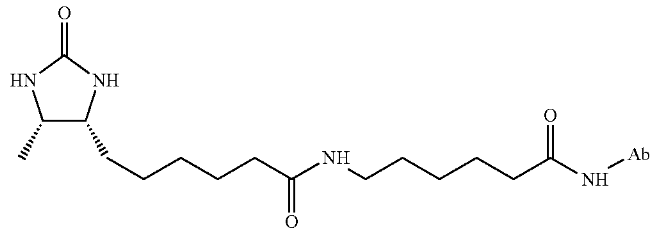 DSB-X-Ab | 97% | 16% |
| 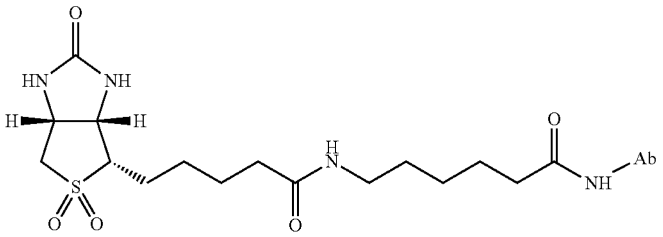 1-Ab | 60% | 35% |
| 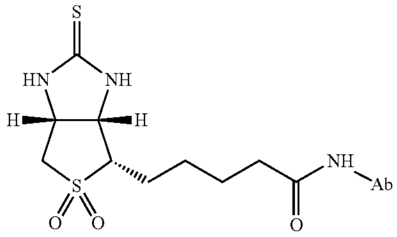 2-Ab | 17% | 8% |
| 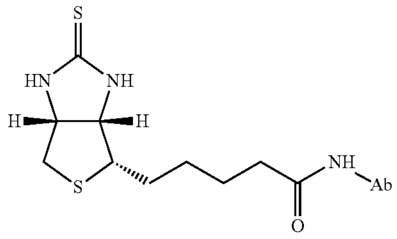 3-Ab | 86% | 75% |
| 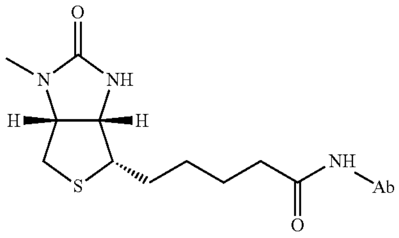 4-Ab | 55% | 85% |

TABLE 5-continued
| Capture and detachment efficiency of antibody-lined biotin derivatives | | |
|---|---|---|
| Biotin derivative | Capture | Detachment |
| 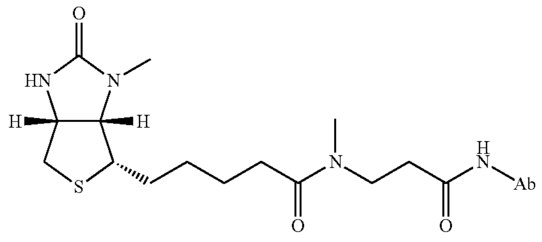 114-Ab | 84% | 76% |
| 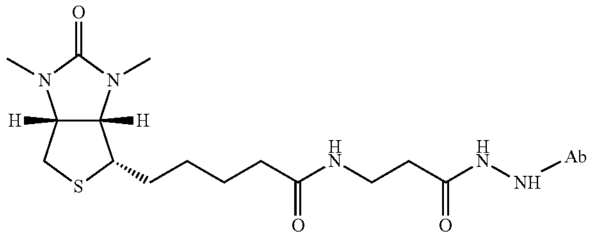 2,5-dioxopyrrolidin-1-yl 3-(5-((3aS,4S,6aR)-1,3-dimethyl-2-oxohexahydro-1H-thieno[3,4-d]imidazol-4-yl)pentanamido)propanoate-Ab | 0% | n/a |
| 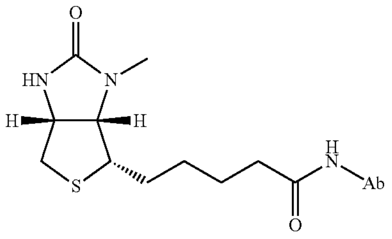 5-Ab | 82% | 64% |
| 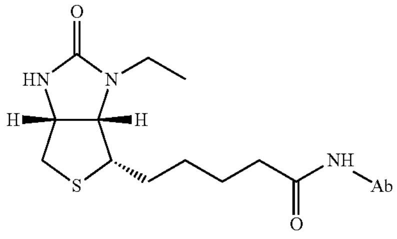 6-Ab | 94% | 84% |
| 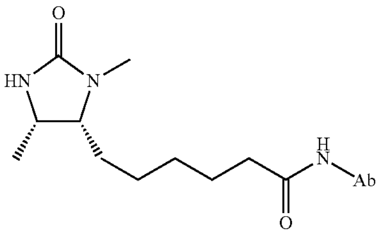 9-Ab | 70% | 85% |

TABLE 5-continued
| Capture and detachment efficiency of antibody-lined biotin derivatives | | |
|---|---|---|
| Biotin derivative | Capture | Detachment |
| 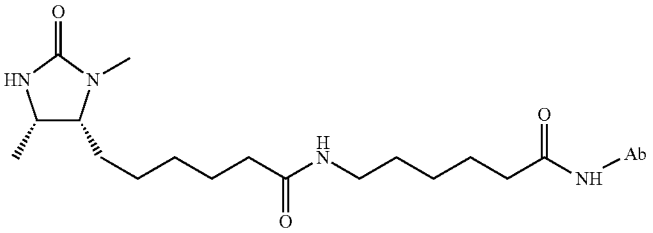 10-Ab | 76% | 92% |
| 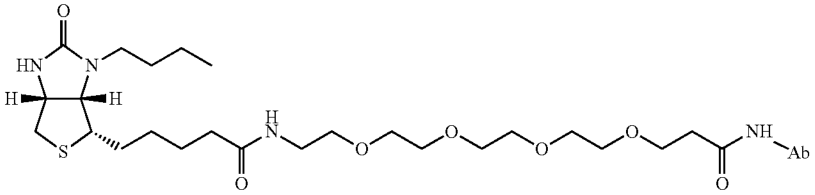 11-Ab | 90% | 92% |
| 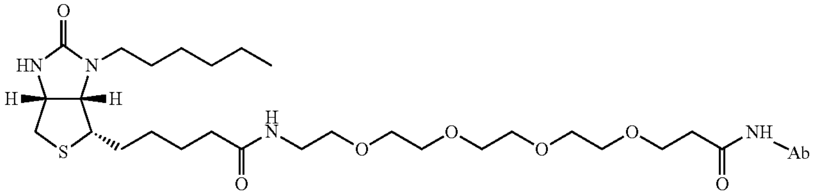 12-Ab | 98% | 95% |
| 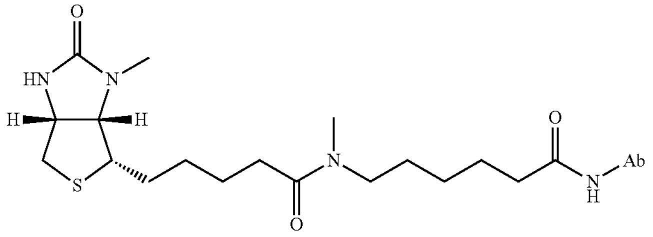 113-Ab | 94% | 65% |
| 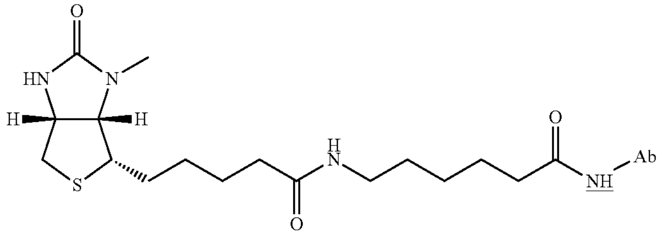 14-Ab | 98% | 60% |
| 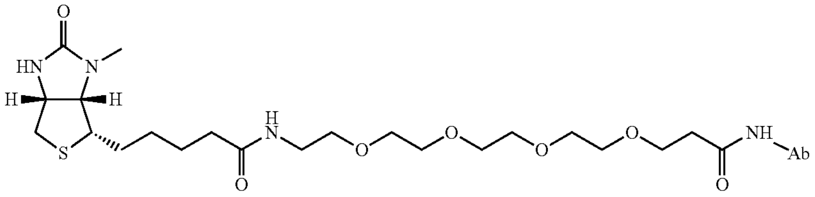 15-Ab | 100% | 55% |

TABLE 5-continued
| Capture and detachment efficiency of antibody-lined biotin derivatives | | |
|---|---|---|
| Biotin derivative | Capture | Detachment |
| 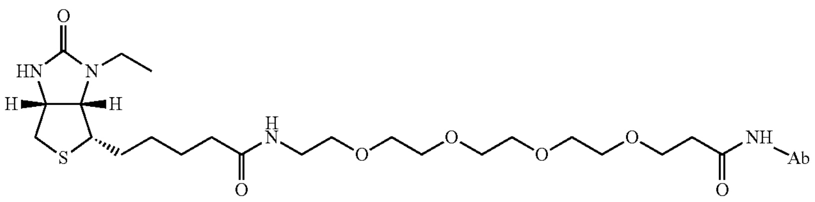 17-Ab | 97% | 100% |
| 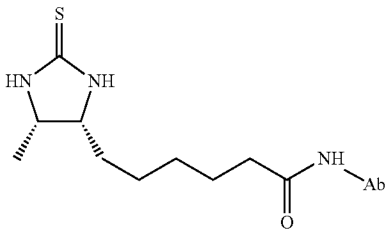 18-Ab | 75% | 85% |
| 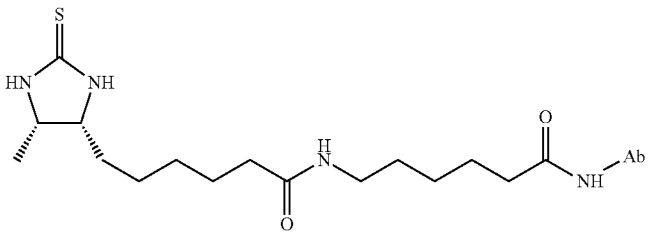 19-Ab | 84% | 92% |
| 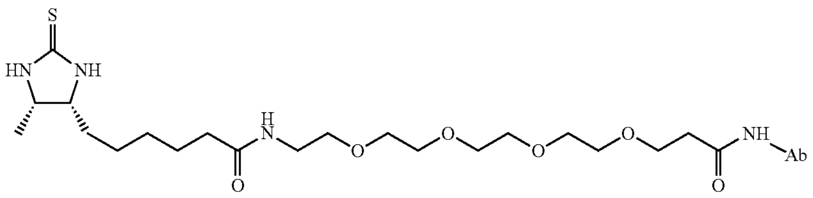 20-Ab | 92% | 95% |

TABLE 5-continued
| Capture and detachment efficiency of antibody-lined biotin derivatives | | |
|---|---|---|
| Biotin derivative | Capture | Detachment |
| 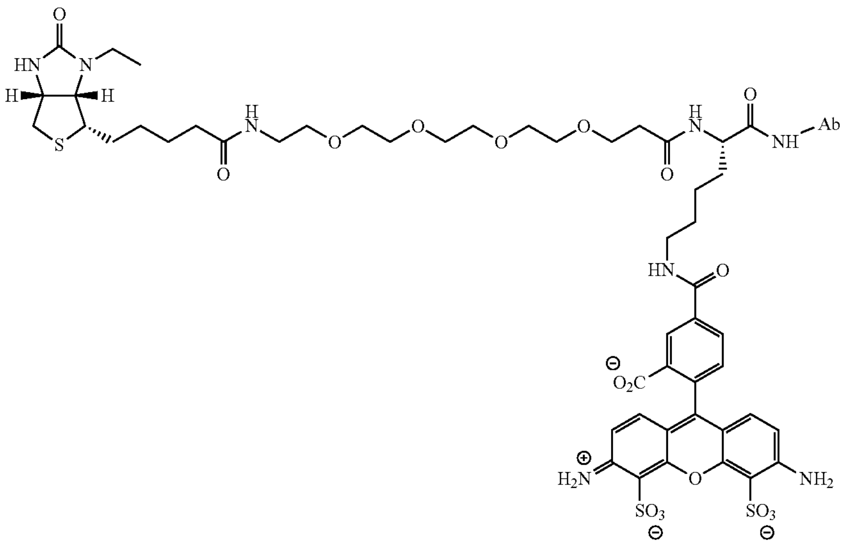 21-Ab | 97% | 99% |
| 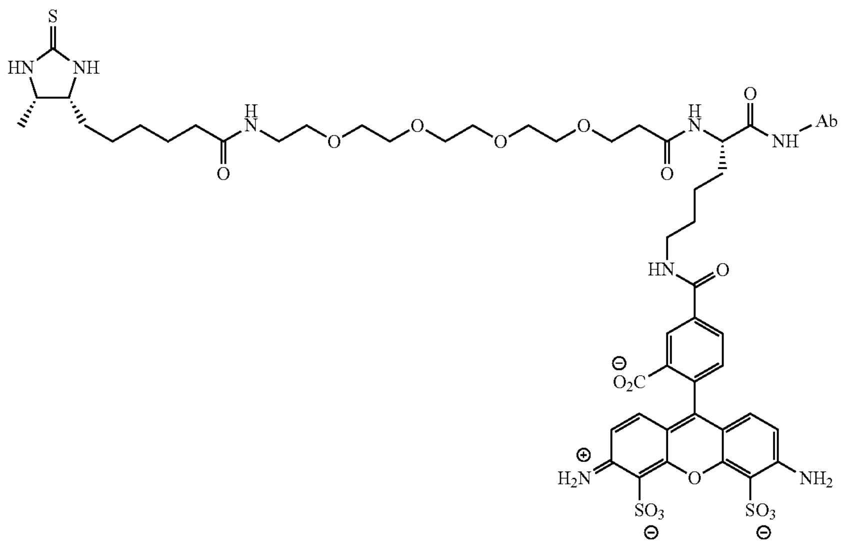 22-Ab | 94% | 95% |

Example 14: Effect of Molar Ratio of Labeling on Capture and Detachment Efficiency Antibodies were labeled with biotin derivatives 14, 17, and 20, using the method described in Example 12. The labeling was carried out at various initial molar ratios of the biotin derivative to antibody. The method described in Example 13 was then used to determine the effect of initial molar ratio of labeling on capture and detachment efficiency. The results of that experiment are shown in Table 6.

TABLE 6

Capture and detachment efficiency of varying labeling molar ratio of biotin derivatives to antibody

| Biotin derivative | Initial Molar Ratio (biotin derivative to antibody) | Capture | Detach. |
|---|---|---|---|
| 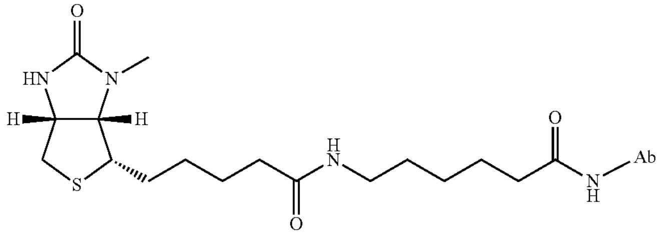 14-Ab | 5 | 97% | 78% |
| 14-Ab | 10 | 98% | 75% |
| 14-Ab | 20 | 97% | 62% |
| 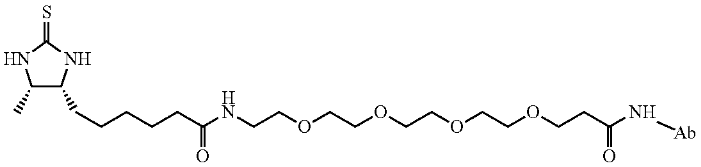 20-Ab | 5 | 55% | 70% |
| 20-Ab | 10 | 70% | 75% |
| 20-Ab | 20 | 80% | 76% |
| 20-Ab | 30 | 94% | 96% |
| 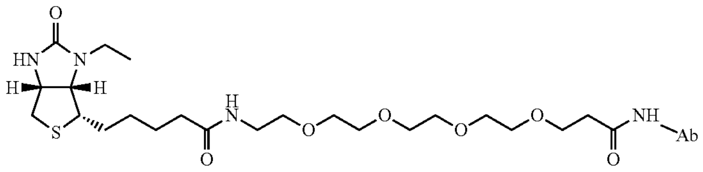 17-Ab | 5 | 75% | 96% |
| 17-Ab | 10 | 80% | 94% |
| 17-Ab | 20 | 97% | 99% |
| 17-Ab | 30 | 100% | 97% |

The results show that initial molar ratios of labeling, from about 10 to about 30, has little effect on the capture and detachment efficiency for biotin derivatives 14 and 17. For biotin derivative 20, increasing the molar ratio of labeling can increase the capture and release efficiency.

Example 15: Determination of Rate Constants and Binding Affinity Using BioLayer Interferometry In BioLayer Interferometry (BLI), a layer of molecules bound to the tip of an optic fiber creates an interference pattern in white light reflected from the layer of molecules. A change in the number of molecules bound to the tip of the optic fiber causes a shift in that interference pattern that can be measured. The wavelength shift is a direct measure of the thickness of the layer of molecules. Further, because the shift can be measured in real-time, rates of association and dissociation can be determined. See, e.g., Concepcion et al., *Combinatorial Chemistry and High Throughput Screening,* 12, 791-800 (2009); Lotze, et al., United States Patent Application 20090147264; Abdiche et al., *Anal. Biochem.,* 377(2), 209-217 (2008).

The rate constants and binding affinity of certain biotin derivatives for streptavidin were determined using BLI, as follows. The streptavidin biosensor tips from ForteBio were prewet for 30 min in water prior to use. All interaction analyses were conducted at 25° C. in kinetic buffer. The 96-well microplates used in the Octet were filled with 200 µl of samples or buffer per well and agitated at 1000 rpm. Three different concentrations of antibody-linked biotin derivative samples were added to 96-well microplate in duplicate, and a buffer solution was also added to 96-well microplate as a reference control. The association curve was generated by dipping the streptavidin biosensor tips into the sample well and incubated at 25° C. for 500 seconds at 1000 rpm. The dissociation curve was generated by dipping the streptavidin biosensor tips into the kinetic buffer well and incubated at 25° C. for 500 seconds at 1000 rpm. The kinetic data was obtained using the Data Analysis Octet software.

The results of that experiment are shown in Table 7.

TABLE 7

Binding constants of antibody-linked biotin derivatives

| Biotin derivative | Capture | Detach. | $K_D$ (M) | $K_{on}$ (1/Ms) | $K_d$ (1/sec) |
|---|---|---|---|---|---|
| Biotin-Ab | 100% | 0% | $5.95 \times 10^{-15}$ | $2.41 \times 10^{7}$ | $1.43 \times 10^{-7}$ |
| DSB-Ab | 98% | 10% | $3.54 \times 10^{-13}$ | $1.30 \times 10^{6}$ | $4.58 \times 10^{-7}$ |
| 1-Ab | 60% | 35% | $1.26 \times 10^{-10}$ | $1.30 \times 10^{5}$ | $1.65 \times 10^{-5}$ |
| 3-Ab | 86% | 75% | $4.54 \times 10^{-10}$ | $1.56 \times 10^{5}$ | $7.10 \times 10^{-5}$ |
| 4-Ab | 55% | 85% | $3.92 \times 10^{-9}$ | $1.03 \times 10^{4}$ | $4.04 \times 10^{-5}$ |
| 10-Ab | 76% | 92% | $1.52 \times 10^{-9}$ | $1.73 \times 10^{5}$ | $2.63 \times 10^{-4}$ |
| 14-Ab | 98% | 60% | $1.44 \times 10^{-11}$ | $3.43 \times 10^{5}$ | $4.91 \times 10^{-6}$ |
| 21-Ab | 97% | 99% | $2.56 \times 10^{-11}$ | $3.43 \times 10^{5}$ | $4.91 \times 10^{-6}$ |
| 22-Ab | 94% | 95% | $3.34 \times 10^{-9}$ | $7.85 \times 10^{4}$ | $2.62 \times 10^{-4}$ |
| 11-Ab | 90% | 92% | $5.65 \times 10^{-10}$ | $1.14 \times 10^{5}$ | $6.42 \times 10^{-5}$ |
| 12-Ab | 98% | 95% | $8.79 \times 10^{-12}$ | $3.61 \times 10^{5}$ | $3.17 \times 10^{-6}$ |

The results show that a dynamic diversity of biotin derivatives has been developed with the binding affinity range from $1\times10^{-13}$ M to $1\times10^{-8}$ M. Desired capture and detachment efficiencies can therefore be obtained by choosing appropriate biotin derivatives.

Example 16: Isolation of Antibody-Linked Biotin Derivative from Cell Lysate

To determine if a tunable biotin derivative will function in a cell lysate, goat anti-mouse IgG/biotin derivative 21 conjugate was chosen to validate the protein purification from cell lysate. The cell lysate was prepared by suspending the Jurkat cells (~$3\times10^7$) in 1 ml of Tris Buffer containing 0.5% SDS and sonicating for 1 minute to make about 2 mg/ml total protein. The goat anti-mouse IgG conjugate 21-Ab (100 μg) was mixed with 0.5 ml of cell lysate and vortexed for 30 seconds. 100 μl of streptavidin coated agarose was added, and incubated for 5 minutes at room temperature under rolling and tilting, followed by centrifugation for 3 minutes at 10,000×g. The supernatant was removed. One ml PBS buffer was added to the streptavidin beads, and mixed for 3 minutes at RT, followed by centrifugation for 3 minutes at 10,000×g. The supernatant was removed. The PBS washing step was repeated twice. 500 μl of 3 mM biotin solution was added to the streptavidin beads and incubated for 5 minutes at RT under rolling and tilting, followed by centrifugation for 3 minutes at 10,000×g. The goat anti-mouse IgG conjugate 21-Ab was recovered in the supernatant. The recovery efficiency was measured by the fluorescent intensity. The purity of isolated protein was checked by protein gel stain.

Figure 1B:
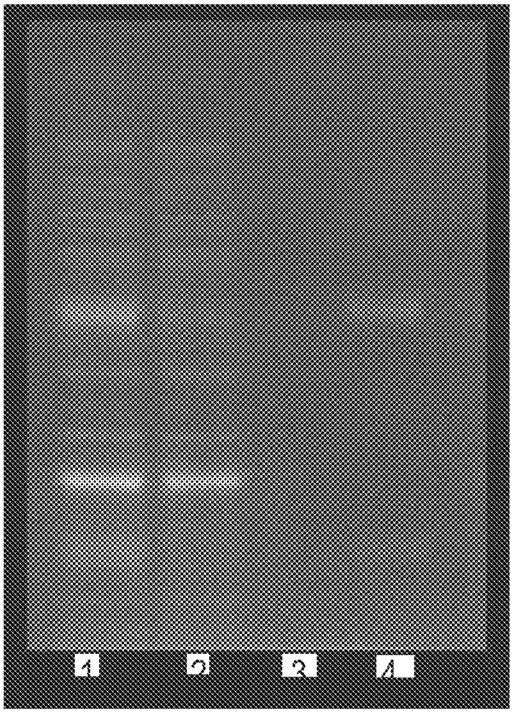

The results are shown in FIG. 1A and FIG. 1B. FIG. 1A shows the fluorescence labeled protein distribution in the tube before the capture and after the capture, then after release from streptavidin coated agarose. FIG. 1B shows the protein gel stain of cell lysate mixture, supernatant, washing, and purified protein.

Example 17: Isolation of T Cells from Peripheral Blood Mononuclear Cells

To determine if an antibody-linked biotin derivative can be used to isolate CD3+ T cells, an anti-CD3 antibody was labeled with biotin derivative 17. Peripheral blood mononucleocytes (PBMCs) were isolated from anti-coagulated peripheral blood or leukocyte enriched buffy coat using standard procedure. Isolation Buffer ($Ca^{2+}$ and $Mg^{2+}$ free phosphate buffered saline (PBS) supplemented with 0.1% BSA and 2 mM EDTA) was prepared. The PBMCs were suspended with Isolation Buffer at $1\times10^8$ cells/ml. 500 μl (~$5\times10^7$ cells) of the PBMCs suspension, was mixed with 25 μl anti-CD3 antibody labeled with biotin derivative 17 for 10 minutes at 2-8° C. Two ml Isolation Buffer was added to wash cell, followed by centrifugation for 8 minutes at 350×g. The supernatant was removed and discarded. One ml Isolation Buffer was added and the cell pellet was resuspended.

75 μl of resuspended M280 Streptavidin Dynabeads (10 mg/ml) was added and mixed at room temperature for 15 minutes. The tube was placed on the magnet for 1 minute. The supernatant was carefully removed and discarded. The tube was removed from the magnet, and 1 ml Isolation Buffer was added, and the bead-bound cells were suspended by gentle pipetting 5 times. The tube was placed on the magnet for 1 minute. The supernatant was carefully removed and discarded. The tube was removed from the magnet and the bead-bound cells was resuspended in 1 ml of fresh 5 mM biotin buffer in Isolation Buffer, and incubated for 10 minutes at room temperature under rolling and tilting. The tube was placed on the magnet for 1 minute, and the supernatant containing the bead-free cells was transferred to a new tube, and was again placed on the magnet for 1 minute to remove any residual beads. The supernatant containing the bead-free cells was transferred to a new tube, and 2 ml Isolation Buffer was added, followed by centrifugation for 8 minutes at 350×g. The supernatant was discarded and the cell pellet was resuspended in preferred medium (such as MEM, DMEM, or RPMI). The viability and purity of isolated CD3+ T cells was checked by Flow Cytometry.

Figure 2:
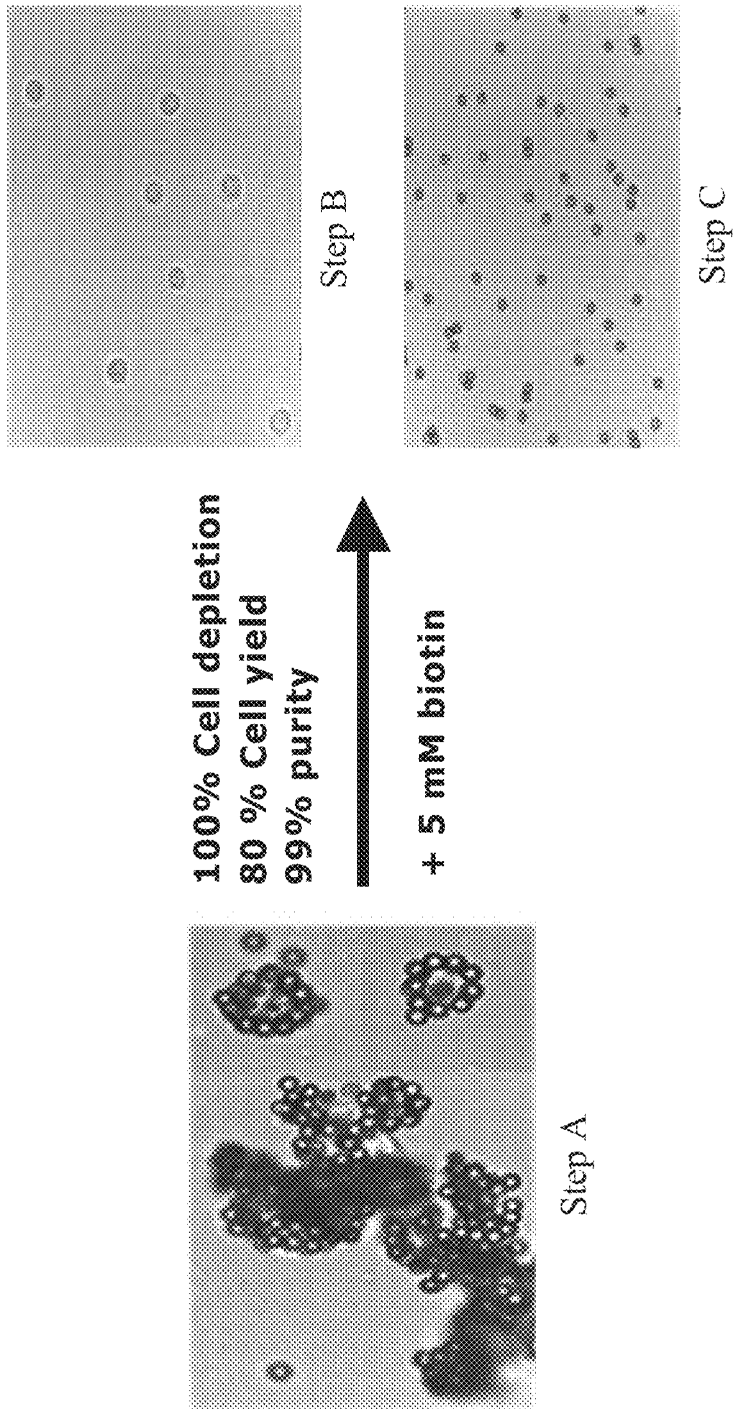
FIG. 2 shows isolation of CD3+ T cells from a mononuclear cell pool using an anti-CD3 antibody linked to a biotin derivative 17. Step A shows the CD3+ T cells from a mononuclear cell pool, bound to anti-CD3 antibody labeled with biotin derivative 17, the complexes of which are bound to M280 Strepavidin Dynabeads. Step B shows the isolated CD3+ T cells, which have been disassociated from the M280 Strepavidin Dynabeads. Step C shows the M280 Streptavidin Dynabeads after dissociation of CD3+ T cell/anti-CD3 antibody complexes. (The sizes of the disassociated CD3+ T cell complexes shown in Step B and the disassociated M280 Strepavidin Dynabeads shown in Step C are not to the same scale as FIG. 1A.)

The results are shown in FIG. 2. FIG. 2, Step A shows the mononuclear cell pool incubated with anti-CD3 antibody labeled with biotin derivative 17, which is then bound to M280 Streptavidin Dynabeads. FIG. 2, Step B shows the isolated CD3+ T cells following dissociation of biotin derivative 17 from the M280 Streptavidin Dynabeads. FIG. 2, Step C shows the free M280 Streptavidin Dynabeads after elution with biotin solution. In that experiment, 100% of the CD3+ T cells were depleted from the mononuclear cell pool, as determined by flow cytometry. Further, 80% of the CD3+ T cells were recovered, and the recovered CD3+ T cells were 99% pure.

Example 18: Preparation of AlexaFluor 488 Derivative of Compound 17

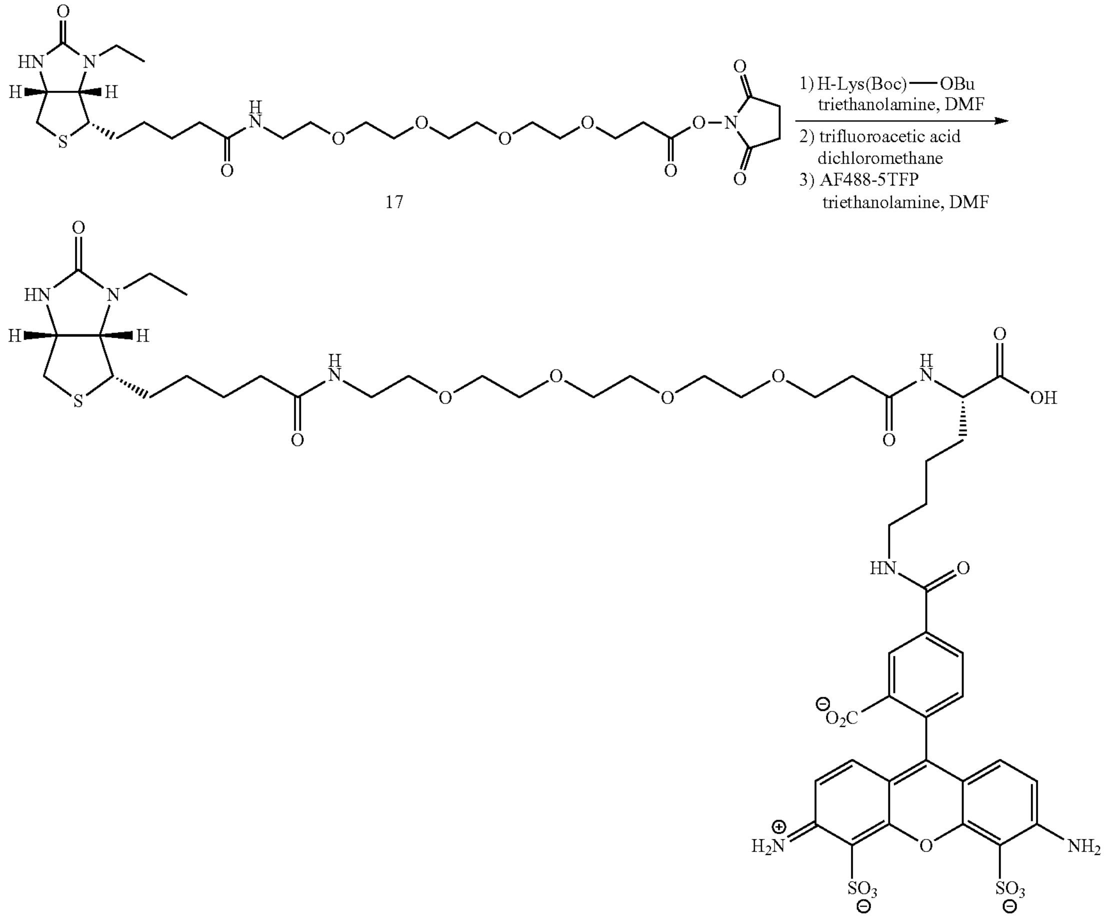

17

117

Example 19: Binding Affinity and Reversibility of Binding of Compound 117 with Strepavidin In order to evaluate the binding affinity and reversibility of N3'-ethyl biotin with streptavidin, a simple fluorescent binding and release assay was designed. Briefly, N3'-ethyl biotin-AF488 conjugate 117 was incubated with M-280 Streptavidin Dynabeads in pH 7.4 PBS buffer. After 25 min incubation at room temperature, the magnetic beads were separated from the supernatant, which was used to measure the capture efficiency, by measuring the fluorescent intensity of the supernatant solution to determine the amount that was not captured. Then, the N3'-ethyl biotin 117 bound magnetic beads were washed with PBS buffer to remove weak or non specific binding. The reversibility was tested by incubating the N3'-ethyl biotin 117 bound magnetic beads with 2 mM biotin in PBS buffer at room temperature for 5 min, then the magnetic beads were concentrated by a magnet, and the fluorescent intensity in the solution was measured to determine the amount that was released. As a control, biocytin-AF488 conjugate was also tested in the same assay format. As shown below, the N3'-ethyl biotin displays high binding efficiency and the binding is fully reversible with biotin competing reagent under non-denaturing conditions.

| Compound | Capture efficiency | Release efficiency |
|---|---|---|
| Biocytin | 96 ± 2% | <5% |
| 117 | 94 ± 3% | 95 ± 4% |

The details of fluorescent capture and release assay were as follows. 100 μL of M280 Streptavidin Dynabeads (10 mg/mL, Invitrogen) was transferred to a 1.5 mL centrifuge tube, and washed with 500 μL PBS three times. 500 μL of N3'-Ethyl biotin-AF488 conjugate 117 (0.2 μM in PBS buffer, pH 7.4) was added and mixed under rolling and tilting at room temperature for 25 minutes. The tube was placed on the magnet for 1 minute, to concentrate the magnetic beads on the magnet. The supernatant was carefully removed and saved for measuring the capture efficiency, by measuring the fluorescent intensity of the supernatant solution. The tube was removed from the magnet, and 500 μL PBS was added, then the beads were resuspended by gentle pipetting 5 times. The tube was placed on the magnet for 1 minute. The supernatant was carefully removed. The PBS washing was repeated one more time. The tube was removed from the magnet and the beads were carefully resuspended in 500 μL of 2 mM biotin in PBS (pH 7.4), with mixing under rolling and tilting at room temperature for 5 minutes. The tube was placed on the magnet for 1 minute. The supernatant was carefully removed and saved for measuring the release efficiency, by measuring the fluorescent intensity of the supernatant solution.

Example 20: Kinetic Measurement of Rate Constants

Figure 3:
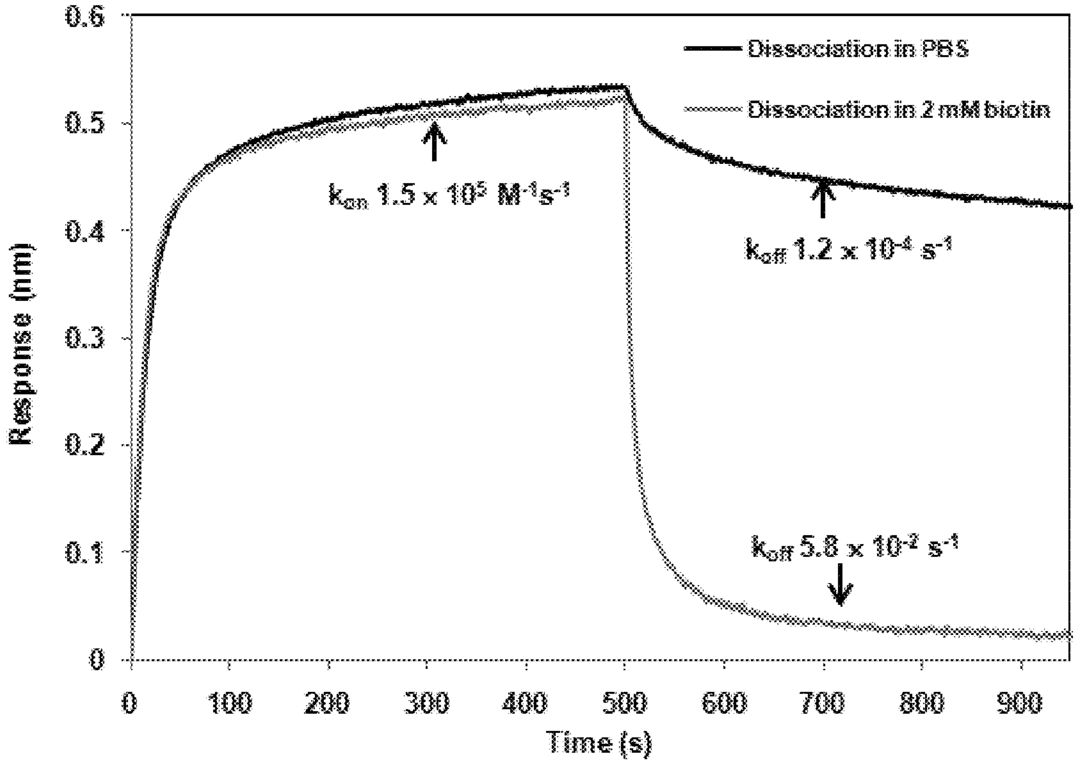
FIG. 3 shows the association and dissociation curves between N3'-ethyl biotin and streptavidin on ForteBio system.

The binding constant and on-and-off rate constant of N3'-ethyl biotin with streptavidin were tested using a label-free ForteBio system. The N3'-ethyl biotin 117 was covalently immobilized to amine reactive sensor tips from ForteBio. To generate the association curve, the N3'-ethyl biotin labeled biosensor tips were incubated with streptavidin at 25° C. The dissociation curve was determined by incubating the streptavidin bound sensor tips in PBS buffer described above, as well as in PBS buffer containing 2 mM biotin at 25° C. As shown in FIG. 3, the N3'-ethyl biotin shows fast on-rate with streptavidin ($k_{on}$~$1.5\times10^{5}$ $M^{-1}S^{-1}$), and relative slow off-rate from streptavidin in PBS buffer ($k_{off}$~$1.2\times10^{-4}$ $S^{-1}$). The dissociation constant $k_D$ of N3'-ethyl biotin is about 0.8 nM. In the presence of 2 mM biotin, the N3'-ethyl biotin displays fast off-rate ($k_{off}$~$5.8\times10^{-2}$ $S^{-1}$), thus leads complete dissociation from streptavidin.

The details of fluorescent capture and release assay were follows. All interaction analyses were conducted at 25° C. in kinetic buffer (PBS, 0.1% BSA, 0.05% Tween-20, pH 7.2). The amine reactive biosensor tips from ForteBio were prewet for 20 min in water prior to use. The prepared samples and buffers were added to a 96-well microplate at 200 μL per well according the following sample layout, and the entire 96-well plate was agitated at 1000 rpm. Eight biosensor tips were performed the kinetic assay in parallel. Each amine reactive biosensor tip was equilibrated in MES buffer for 5 min, then activated with EDC/NHS for 5 min. The activated biosensor tip was labeled with 2 mM N3'-ethyl biotin 117 for 10 min, then quenched with 1 M ethanolamine for 5 min. The N3'-ethyl biotin 117 immobilized biosensor tip was incubated in kinetic buffer for 5 min to generate baseline, then incubated with 2 μg/mL streptavidin in kinetic buffer or kinetic buffer (control) at 1000 rpm for 10 min to generate association curve, followed by incubation with kinetic buffer or 2 mM biotin in kinetic buffer at 1000 rpm for 10 min to generate dissociation curve. The ForteBio Data Analysis Octet software was used to process the curve by subtracting sample curve from reference curve, and the kinetic data was calculated by fitting curve.

Example 21: Preparation of Propargyl Derivative of Compound 21

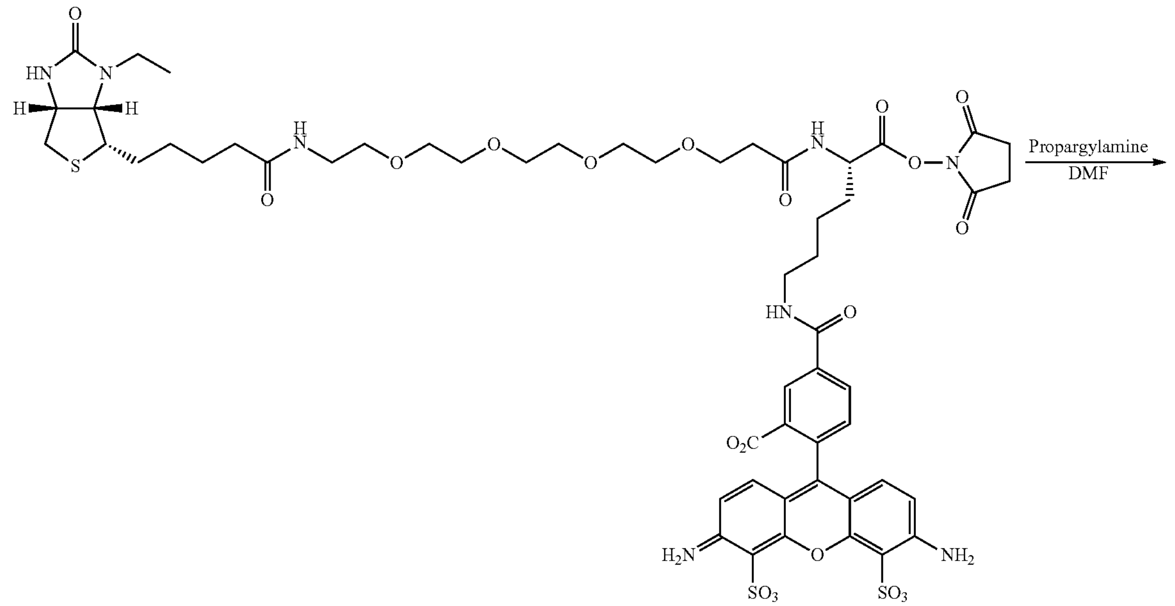

-continued

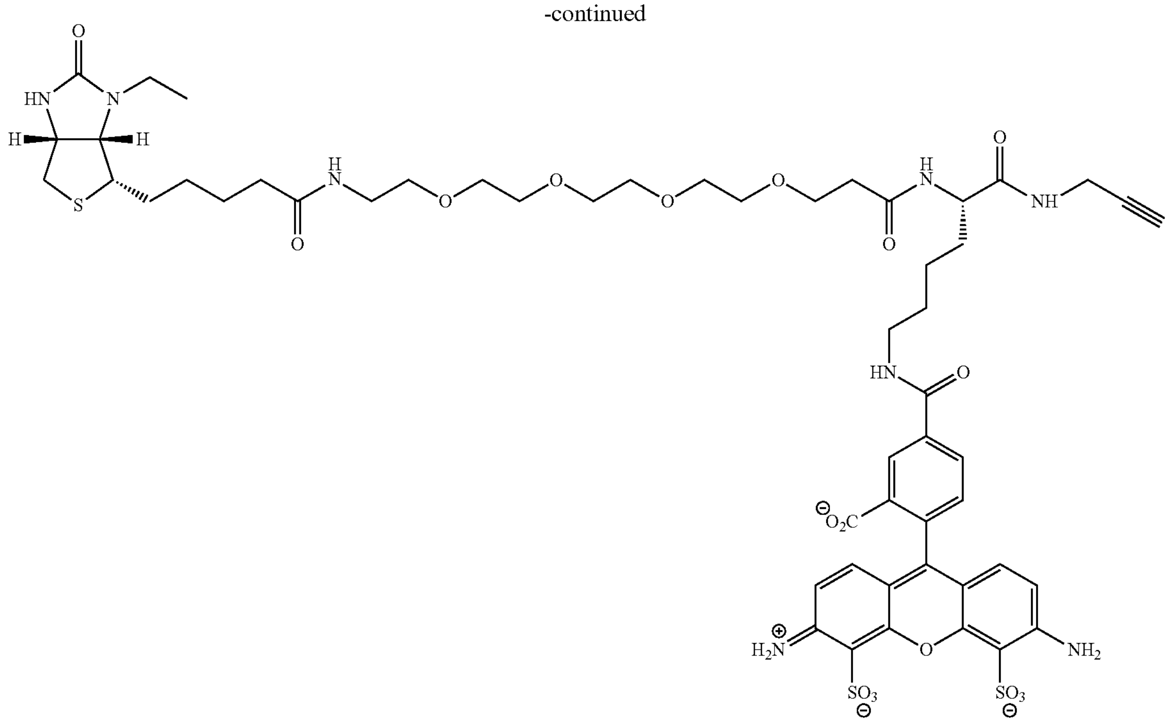

118

Example 22: Use of N3'-Ethyl Biotin Alkyne 118 for Labeling, Detection and Isolation in a Biological System The azido sugar labeling system was used to demonstrate the ability of N3'-ethyl biotin alkyne 118 for efficient labeling, detection, and isolation in a biological system.

Protein Labeling and Detection in Cells.

HeLa cells were cultured on glass coverslips in 10 mL Minimum Essential Medium (MEM) supplemented with 10% fetal bovine serum (FBS) at four 100 mm tissue culture dishes. To each tissue culture dish, 10 μL of $Ac_4$GlcNAz (100 mM in DMSO), $Ac_4$GalNAz (100 mM in DMSO), $Ac_4$ManNAz (100 mM in DMSO; Life Technologies, San Diego, CA, SKU #s C33367, C33367 and CC33366, respectively), and DMSO were added, respectively. The dishes were incubated at 37° C. humidified incubator with 5% $CO_2$ for 24 h. After incubation, the media was removed, and the HeLa cells were washed with 10 mL DPBS with 1% FBS twice. Then, the HeLa cells were fixed with 3.7% formaldehyde in PBS for 15 min at room temperature and washed with 10 mL DPBS with 1% FBS once. The HeLa cells were permeabilized with 0.5% Triton X-100 in PBS for 15 min at room temperature, then washed with 10 mL DPBS with 1% FBS once. The HeLa cells were labeled with 10 μM of N3'-ethyl biotin alkyne 118 in the presence of 100 μM $CuSO_4$, 500 μM tris(3-hydroxypropyltriazolylmethyl)amine (THPTA), and 2.5 mM sodium ascorbate in DPBS with 1% FBS at room temperature for 30 min. For control experiment, the HeLa cells were also labeled with 10 μM of N3'-ethyl biotin alkyne 118 without $CuSO_4$. After labeling, the HeLa cells were washed again with DPBS with 1% FBS twice, and incubated with a nuclear stain Hoechst 33342 (1:5000 dilution) in DPBS with 1% FBS for 10 min. The cells were washed with DPBS with 1% FBS three times, and $eH_2O$ once. After the coverslips were air-dried, the coverslips were mounted in Cytoseal onto microscopy slides. Fluorescent images were captured on a Zeiss Axioskop 2 fluorescence microscope with 40× objective equipped with a Hamamatsu ORCA-ER CCD camera using excitation and emission filters from Omega Optical. The nuclear stain Hoechst 33342 was imaged using a 365±5 nm band-pass filter for excitation and a 400±5 nm cutoff filter for emission. The Alexa Fluor 488 fluorophore was imaged using a 480±10 nm band-pass filter for excitation and a 510±10 nm band-pass filter for emission. Exposure times of 20 and 50 ms, for the nuclear stain and Alexa Fluor 488 (AF488) dye channels, respectively, were used for image collection. All raw images were processed using Slidebook software with identical leveling.

Figure 4:
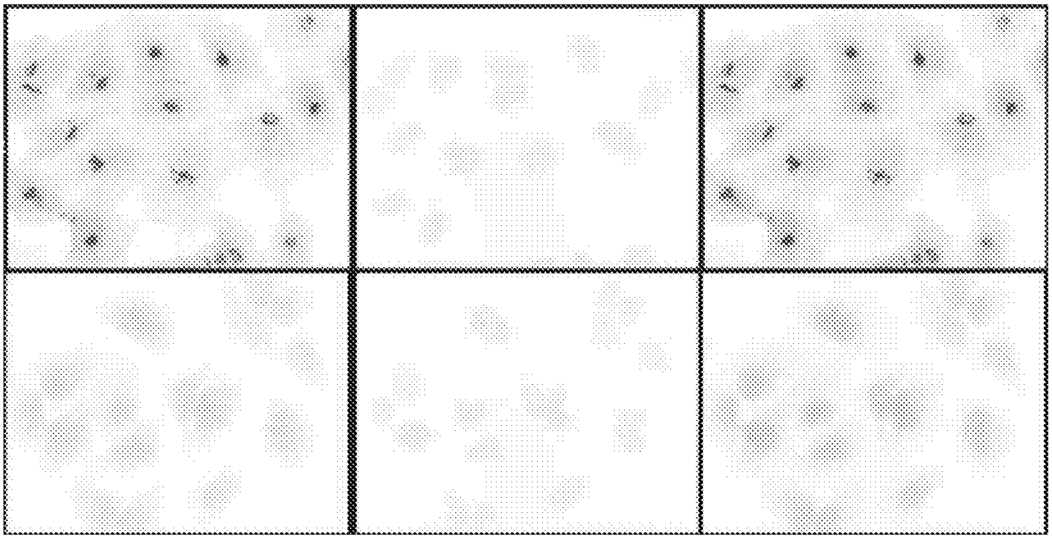
FIG. 4 shows the fluoresence microscopy of HeLa cells labeled with N3'-ethyl biotin alkyne 118. Cells incubated with $Ac_4$MaNAz supplemented media (top) or unsupplemented media (bottom) were labeled N3'-ethyl biotin alkyne 118 in the presence of Cu(I)/THPTA as catalyst. Fluorescence signal from AF488 (left), the nuclear stain, Hoechst 33342, (center) and the merged images (right) are shown.
Figure 5:
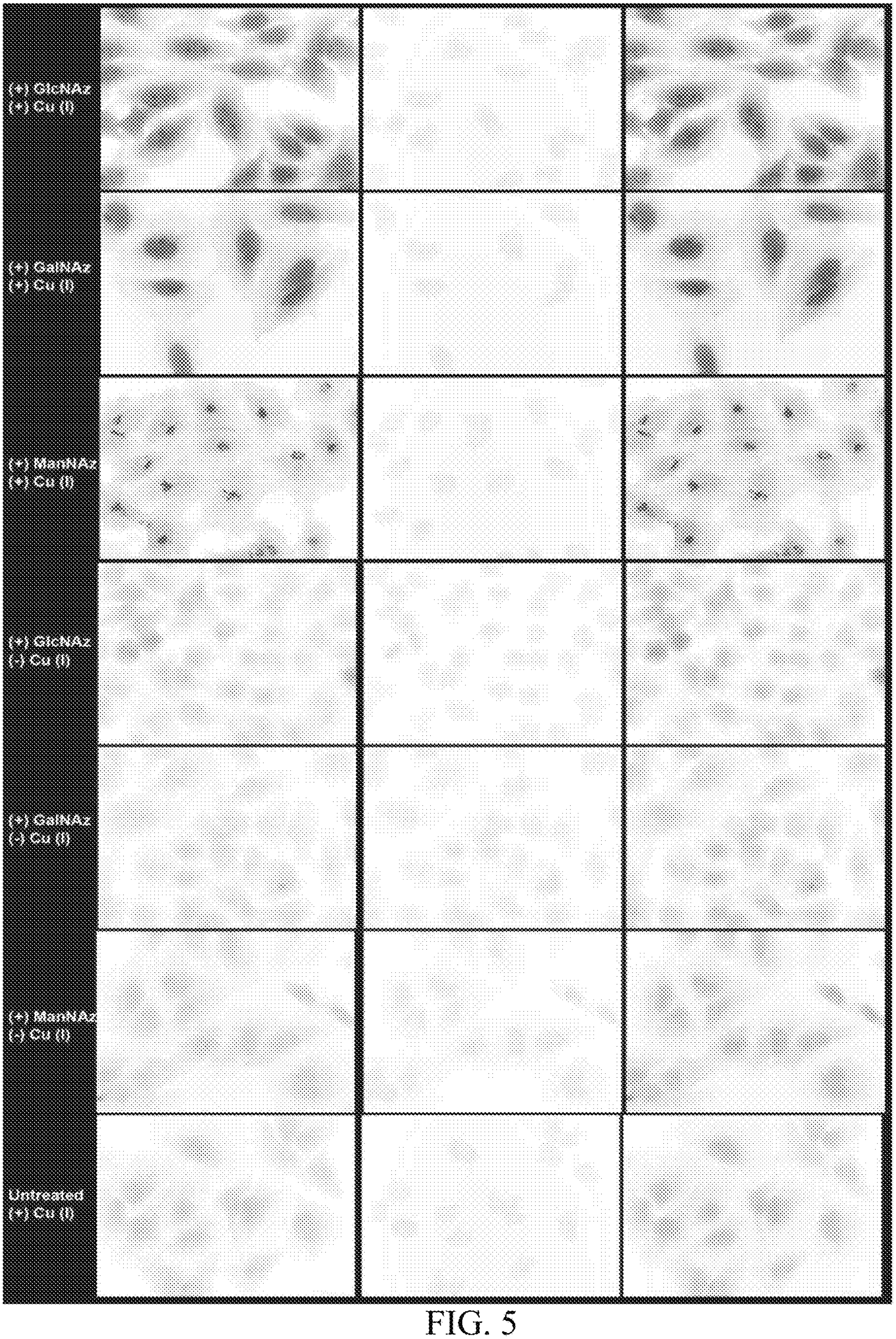
FIG. 5 shows the fluoresence microscopy of HeLa cells labeled with N3'-ethyl biotin alkyne 118. Cells incubated with $Ac_4$GlcNAz, $Ac_4$GalNAz, or $Ac_4$MaNAz supplemented media (top) were labeled N3'-ethyl biotin alkyne 118 in the presence of Cu(I)/THPTA as catalyst (rows 1-3) or in absence Cu(I) (rows 4-6). Cells not incubated with $Ac_4$GlcNAz, $Ac_4$GalNAz, or $Ac_4$MaNAz were treated with N3'-ethyl biotin alkyne 118 in the presence of Cu(I)/THPTA as catalyst as a control (row 7). Fluorescence signal from AF488 (left), the nuclear stain, Hoechst 33342, (center) and the merged images (right) are shown.

The cells incubated with azido sugars show increased fluorescence signal when compared to control cells that were not incubated with azido sugar, as shown in FIG. 4 and, indicating the labeling of cells with N3'-ethyl biotin alkyne 118 via formation of triazole linkage. The enhancement of fluorescence signal is only observed in the presence of both catalyst Cu(I) and azido glycans. The Cu(I) chelating ligand, THPTA, facilitates the reaction and protects protein damage, but is not necessary for labeling of cells. Cells incubated with Ac4MaNAz supplemented media (top) or unsupplemented media (bottom), as shown in FIG. 4, were labeled N3'-ethyl biotin alkyne 118 in the presence of Cu(I)/THPTA as catalyst. Fluorescence signal from AF488 (left), the nuclear stain, Hoechst 33342, (center) and the merged images (right) are shown. These results demonstrate N3'-ethyl biotin alkyne 118 is an efficient reagent for labeling and detection in cells.

Protein Isolation.

In order to isolate azido sugar containing glycoproteins from cell mixture, the Jurkat cells were cultured in $Ac_4$GlcNAz supplemented media for 24 h. In this culturing, Jurkat cells were cultured in 100 mL RPMI 1640 media supplemented with 10% FBS at two T175 tissue culture flasks. When cell density reached ~10×10$^6$ cells/mL, 100 μL of $Ac_4GlcNAz$ (100 mM in DMSO) and DMSO (control) were added, respectively. The flasks were incubated at 37° C. humidified incubator with 5% $CO_2$ for 24 h. After incubation, the Jurkat cells were collected by centrifugation at 600×g for 5 min, and washed with PBS five times. The cell pellet was suspended in PBS to adjust the cell density at 50×10$^6$ cells/mL, and transferred 1 mL each to 1.5 mL tube. The cells were collected again by centrifugation at 600×g for 5 min. Then, 1 mL of 0.5% SDS/PBS was added to each tube, and lysated by sonication. The cell lysate was prepared at ~3 mg/mL in 0.5% SDS/PBS.

Cell lysate was incubated with N3'-ethyl biotin alkyne 118 or biotin alkyne in the presence of $CuSO_4$, THPTA, and sodium ascorbate at room temperature as described below. N3'-Ethyl biotin alkyne 118 and biotin alkyne (Invitrogen) were used to perform parallel protein enrichment experiments. Biotin alkyne has the structure:

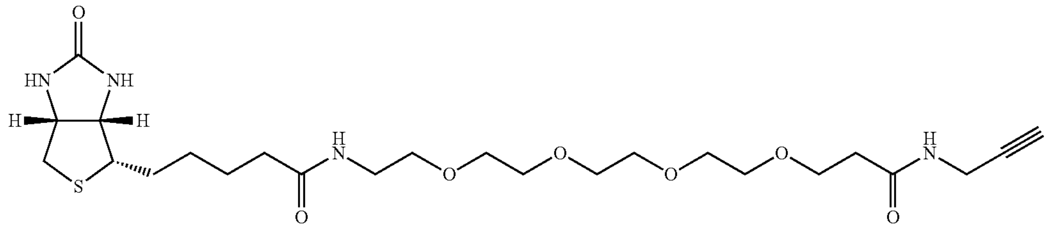 [SMILES: C#CCNC(=O)CCOCCOCCOCCOCCNC(=O)CCCC[C@@H]1SC[C@@H]2NC(=O)N[C@@H]21]

The cell lysate (500 μL, $Ac_4GlcNAz$ treated or untreated) were incubated with 50 μM of N3'-ethyl biotin alkyne 118 or biotin alkyne in the presence of 0.5 mM $CuSO_4$, 2.5 mM THPTA, and 5 mM sodium ascorbate in 0.5% SDS/PBS at room temperature for 1 h, respectively. For control experiment, the cell lysate were also incubated with 50 μM of N3'-ethyl biotin alkyne 118 or biotin alkyne without $CuSO_4$, respectively.

After click labeling, the proteins were enriched with streptavidin agarose at room temperature. After incubation to perform the click labeling, 500 μL MeOH and 150 μL $CHCl_3$ were added to each tube. The tube was vortexed and centrifuged at 10,000 rpm for 4 min. The solution was removed and the pellet was washed with MeOH five times, then resolubilized in 500 μL of 0.5% SDS/PBS. 200 μL of Streptavidin agarose (Invitrogen) was added to each tube and incubated at room temperature for 1 h. The agarose beads were transferred to 2 mL spin column (Bio-Rad), and washed with 2 mL TEST (10 mM Tris, 1 mM EDTA, 1 M NaCl, 0.1% Tween-20, pH 7.4) five times. After washing step, the proteins labeled with N3'-ethyl biotin alkyne 118 were eluted out from streptavidin agarose using 2 mM biotin or 10 mM HCl in $H_2O$ (1 mL×3); the proteins labeled with biotin alkyne were eluted out by heating protein-bound streptavidin agarose in 1% SDS in $H_2O$ at 95° C. for 5 min. The eluate was collected and dried in a speed vac.

As a control, cell lysate was also incubated with N3'-ethyl biotin alkyne 118 or biotin alkyne without Cu(I) catalyst. Another control is using untreated cell lysate to perform the same isolation procedure.

Figure 6:
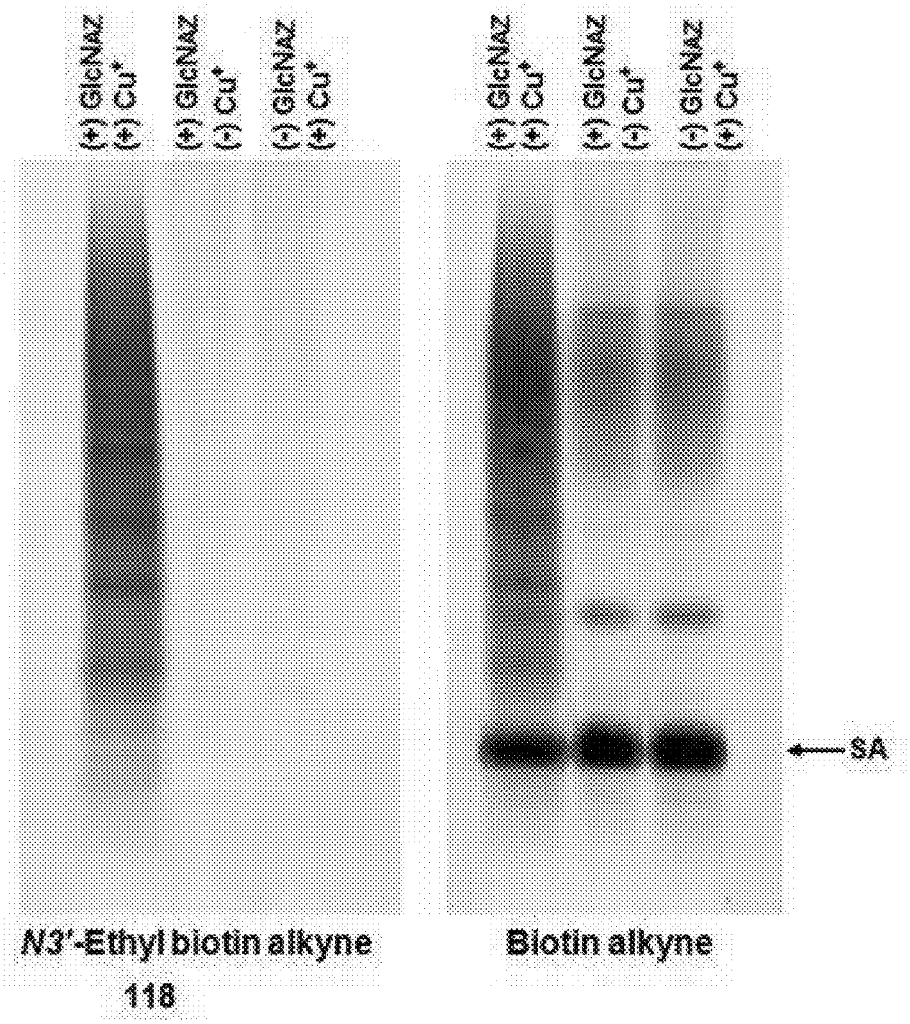
FIG. 6 shows the isolation of glycoproteins using click chemistry. Cell lysate was incubated with N3'-ethyl biotin alkyne 118 or biotin alkyne in the presence of Cu(I)/THPTA, captured by streptavidin agarose, washed, and eluted with either 10 mM HCl or 1% SDS in $H_2O$ at 95° C., respectively. The purified fractions were analyzed by a reducing 4-12% SDS-PAGE gel and stained with SYPRO-Ruby.

As shown in FIG. 6, both control experiments without Cu(I) catalyst, and without $Ac_4GlcNAz$ treatment, show very low background using N3'-ethyl biotin alkyne 118, indicating the azido containing glycoproteins were selectively isolated by labeling with N3'-ethyl biotin alkyne 118 via formation of triazole linkage, followed by capture with streptavidin agarose via interaction of N3'-ethyl biotin with streptavidin. One major problem using biotin alkyne is the isolated proteins are contaminated with streptavidin (SA), which is leached out from agarose beads by the harsh, denaturing condition. These results demonstrate using N3'-ethyl biotin has great advantage in gentle release to isolate clean proteins for downstream analysis.

Example 23: Cell Separation Using Strepavidin-N3'-Ethyl Biotin System

Applicants have identified certain biotin analogs which show optimal reversible interaction with streptavidin, that allows (1) fast and complete binding and (2) fast and complete release, under mild, physiological conditions. One of biotin analogs identified, named N3'-ethyl biotin ($k_D$~0.8 nM), has fast on-rate ($k_{on}$~1.5×10$^5$ $M^{-1}S^{-1}$), and also fast off-rate ($k_{off}$~5.8×10$^{-2}$ $S^{-1}$) in the presence of 1 mM bis-biotin competing reagent. Instead, biotin is almost irreversible under the same condition. These reversible interactions between N3'-ethyl biotin and streptavidin provide a unique method for reversible immobilization of N3'-ethyl biotinylated antibody on magnetic streptavidin beads for cell separation applications.

In order to evaluate cell separation efficiency using streptavidin-N3'-ethyl biotin system, the N3'-ethyl biotin 17 (shown below) was first conjugated with mouse anti-human CDx monoclonal antibodies (mAb). The mAbs were also labeled with AlexaFluor 488 (AF488) to allow for flow cytometry analysis.

17

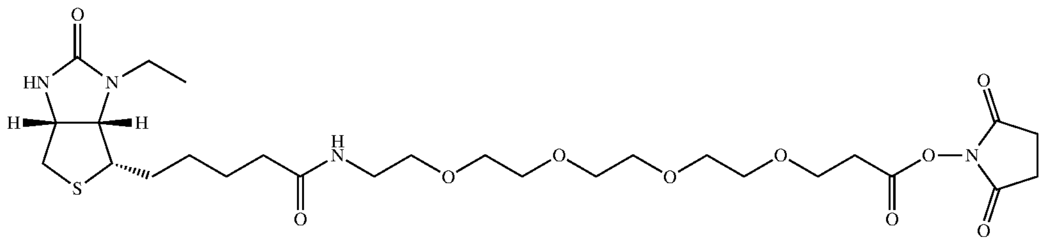

General Procedure of Antibody Labeling with N3'-Ethyl Biotin.

A solution of antibody (both primary and secondary antibody) was prepared at ~3 mg/mL in 0.1 M sodium bicarbonate. N3'-ethyl biotin succinimidyl ester 17 was dissolved in DMSO at ~20 mg/mL. A molar ratio of 10, 20, and 30 equivalents of N3'-ethyl biotin succinimidyl ester 17 was added to the protein solution with stirring (magnetic) at atmosphere, respectively. The reaction mixture was incubated at room temperature for one hour. The N3'-ethyl biotin-antibody conjugate was purified by spin column using BIO-RAD P-30 resin equilibrated with phosphate-buffer saline (PBS).

General Procedure of Antibody Labeling with AlexaFluor Dyes.

A solution of antibody (both primary and secondary antibody) was prepared at ~3 mg/mL in 0.1 M sodium bicarbonate. Alexa Fluor® dye succinimidyl ester was dissolved in DMSO at ~10 mg/mL. A molar ratio of 20 equivalents of Alexa Fluor® 488 succinimidyl ester (Life Technologies, San Diego, CA, SKU #A20000), while for Alexa Fluor® 647 succinimidyl ester (Life Technologies, San Diego, CA, SKU #A20006) a molar ratio of 8 was used. The succinimidyl ester was added to the protein solution with stirring (magnetic) at atmosphere. The reaction mixture was incubated at room temperature for one hour. The Alexa Fluor® dye-antibody conjugate was purified by spin column using BIO-RAD® P-30 resin equilibrated with phosphate-buffer saline (PBS).

Measurement of Degree of Labeling.

Determination of Degree of Labeling (DOL) of N3'-Ethyl Biotin.

The determination of accessible biotin analog in the antibody conjugates was tested using the commercial available FluoReporter® Biotin Quantitation Assay Kit (Life Technologies, San Diego, CA, SKU #F30755). Briefly, 2 mL of HABA/avidin complex was added into two separate test tubes. To each tube, 100 μL of PBS and N3'-ethyl biotin-antibody conjugate were added, respectively, and incubated for 10 min with gentle stirring. The absorbance of both samples was measured at 500 nm, and calculated the difference in absorbance between the two samples (ABS=Blank ABS−Sample ABS). The degree of labeling (DOL) of biotin analogs is calculated using following equation:

$$\text{DOL}=(\text{ABS}\times\text{BSF}\times\text{Mw protein}\times 1000)/(C\times 0.05)$$

BSF: conversion factor ($2.37\times10^{-8}$); C: concentration of protein (mg/mL).

Determination of Degree of Labeling (DOL) of AF488 and AF647.

A simple method for estimating the degree of labeling (DOL) is determined by direct measuring the protein absorbance at 280 nm and AF488 dye (AF647 dye) absorbance at the absorption maximum. The protein concentration is calculated as follows:

$$\text{Protein concentration}\,(M) = \frac{A_{280} - XA_{dye}}{\varepsilon_{protein}}$$

where the molar extinction coefficient (ε) of a typical IgG at 280 nm is 203,000 $cm^{-1}M^{-1}$. The molar extinction coefficient (ε) of AF488 dye at 494 nm is 71,000 $cm^{-1}M^{-1}$, and the correction factor (X) for AF488 dye is 0.11. The molar extinction coefficient (ε) of AF647 dye at 649 nm is 240,000 $cm^{-1}M^{-1}$, and the correction factor (X) for AF647 dye is 0.03.

The degree of labeling (DOL) is calculated as follows:

$$DOL = \frac{A_{dye}\varepsilon_{protein}}{(A_{280} - XA_{dye})\varepsilon_{dye}}$$

Preparation of Cells.

The cell separation was evaluated with a cell model system of human peripheral T lymphocytes (CD3+, CD4+, and $CD8^+$ cells).

The human peripheral blood mononuclear cells (PBMCs) were prepared by $NH_4Cl$ lysis from human peripheral blood obtained from healthy volunteer donors. $NH_4Cl$ lysis buffer (150 mM $NH_4Cl$, 10 mM $NaHCO_3$ and 1 mM EDTA) was prewarmed in 37° C. water bath. Each 5 mL whole blood was added with 45 mL $NH_4Cl$ lysis buffer in a 50 mL centrifuge tube, and was agitated for 15 min at room temperature. The sample was centrifuged at 350×g for 5 min, and supernatant was removed by pipette. The cell pellet was resuspended in 15 mL isolation buffer (DPBS, 0.1% BSA, 2 mM EDTA), and centrifuged again at 350×g for 5 min. Supernatant was removed by pipette, and the cell pellet was resuspended in 2 mL isolation buffer. Count cells and adjust cell concentration to $3\times10^7$ cells/mL.

General Procedure of Cell Separation.

Figure 7A:
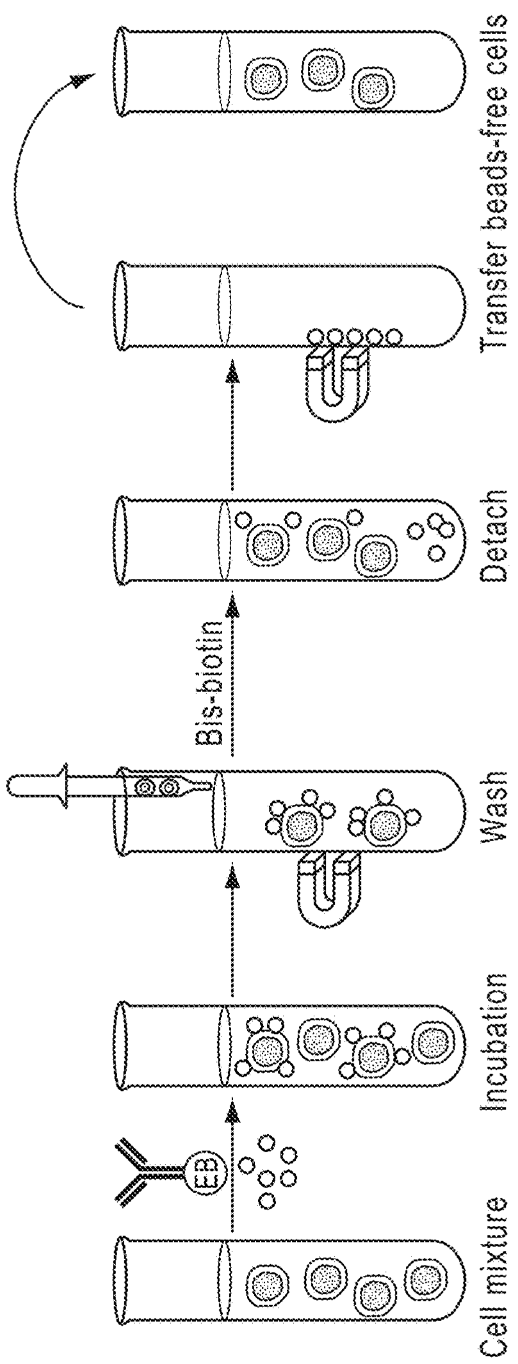
FIG. 7A shows an illustration of cell separation workflow.
Figure 7B:
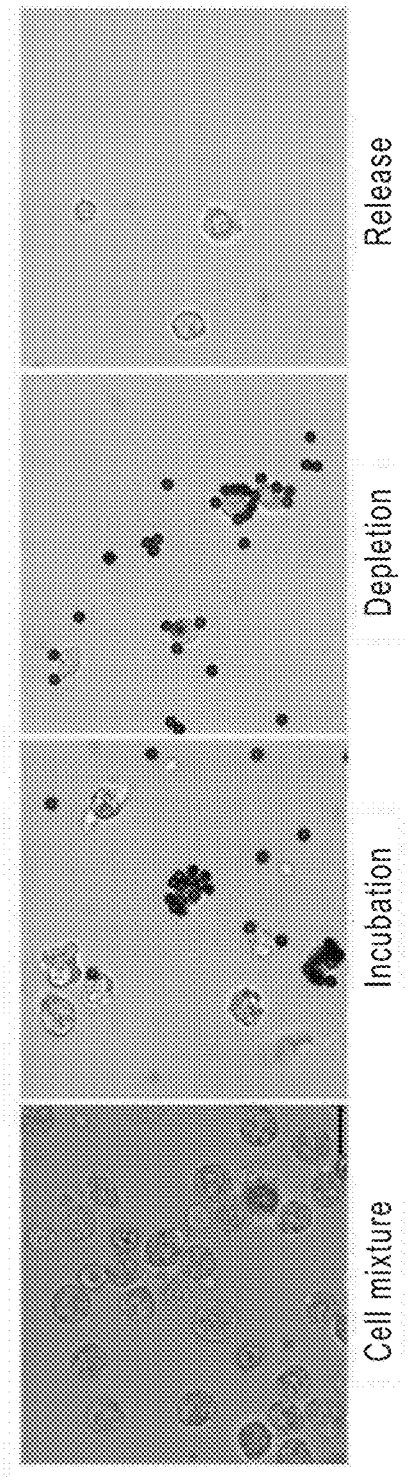
FIG. 7B shows cell imaging at different separation stages. Scale bar, 10 μm.
Figure 7C:
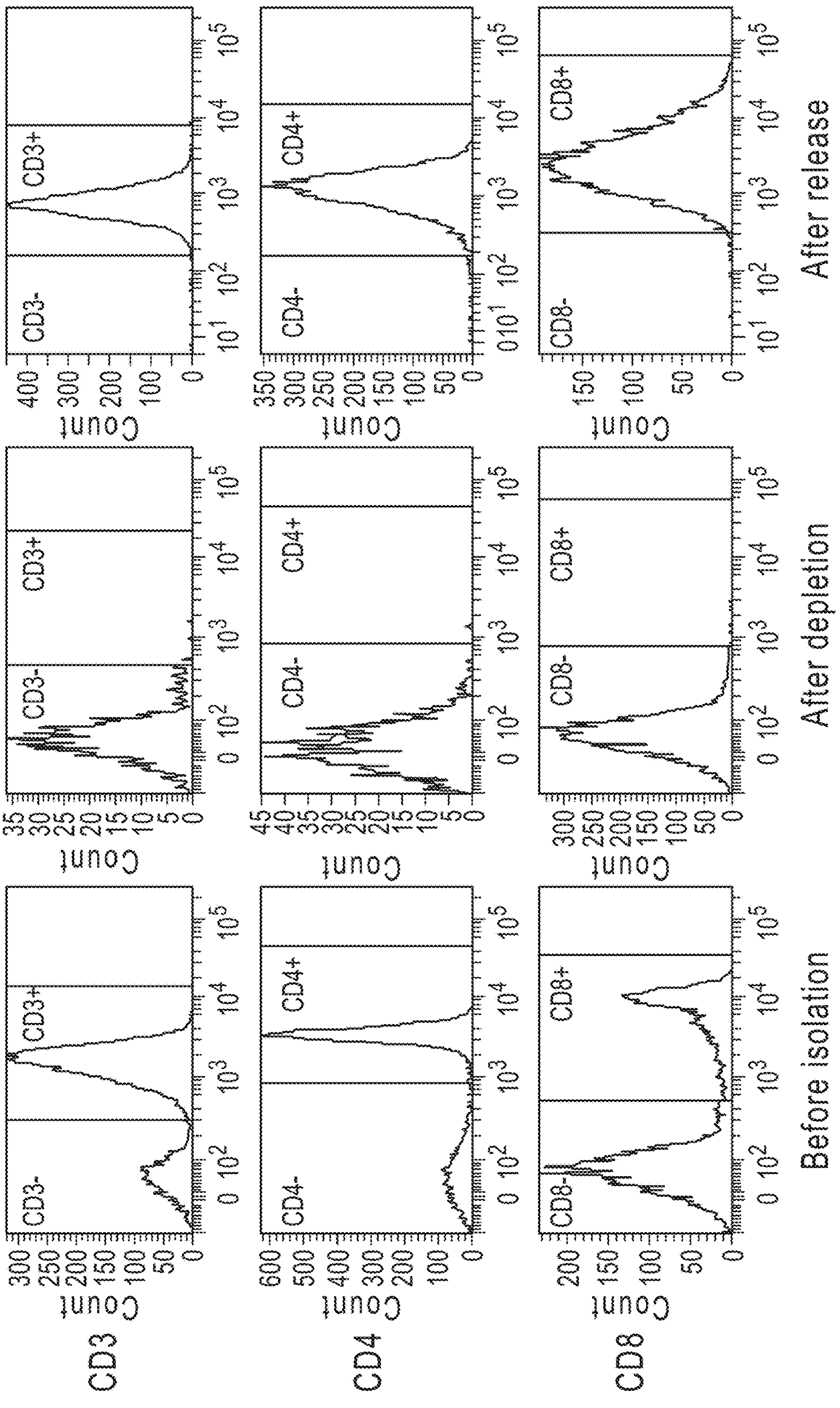
FIG. 7C shows flow histograms of cells based on three different cell surface markers (CD3, CD4, and CD8) at pre-isolation, after depletion, and after release, respectively.

Briefly, PBMCs ($3\times10^7$ cells) were first incubated with mouse anti-human CDx (CD3, CD4, and CD8) mAb-N3'-ethyl biotin 17 conjugate on ice for 10 min, respectively. Then streptavidin M280 Dynabeads® magnetic beads (Life Technologies, San Diego, CA, SKU #112-05D) were added and incubated for 10 min under rolling and tilting at room temperature. The cell mixture was placed on a magnet for 1 min, and the supernatant was removed. The magnetic labelled cells were washed, and then the cells were released from magnetic beads by incubating with 1 mM bis-biotin for 5 min. The amount and viability of isolated cells were measured by Countess® automated cell counter (Life Technologies, San Diego, CA, SKU #C10227). The depletion efficiency and purity of cells were analysed by flow cytometry. The results are summarized in FIGS. 7A-7C and the table below. By demonstrating the feasibility of cell separation based on three different cell surface markers, a simple work-flow (two step incubations, one step wash, and one step detachment, FIG. 7A has been developed. The whole cell separation process can be done in less than 30 min to achieve high recovery (>80%), high purity (>92%), and high viability (>92%). By using streptavidin M280 Dynalbeads, each target cell was captured by multiple magnetic beads (FIG. 7B) through interactions between N3'-ethyl biotin and streptavidin, and can be easily separated by a simple magnet (FIG. 7B]) to achieve high depletion efficiency (98-100%, FIG. 7C). N3'-Ethyl biotinylated mAb was fast and complete released from the streptavidin magnetic beads using 1 mM bis-biotin under physiological conditions to give high recovery, high purity, and high viability of cells (FIG. 7C).

Recovery, purity, and viability of isolated cells.

| Method | Cell type | Recovery[a] | Purity[b] | Viability[a] |
|---|---|---|---|---|
| Primary Ab | CD3 | 87 ± 6% | 96 ± 2% | 96 ± 2% |
| Primary Ab | CD4 | 84 ± 8% | 92 ± 2% | 92 ± 3% |
| Primary Ab | CD8 | 72 ± 5% | 93 ± 3% | 93 ± 2% |
| Secondary Ab | CD3 | 92 ± 4% | 96 ± 2% | 97 ± 2% |
| Secondary Ab | CD4 | 88 ± 6% | 97 ± 2% | 94 ± 2% |
| Secondary Ab | CD8 | 82 ± 5% | 96 ± 2% | 95 ± 3% |

[a]Each recovery and viability is reported the mean of independent triplicate experiments based on Countess ® measurement.
[b]Each purity is reported the mean of independent triplicate experiments based on flow cytometry measurement. Error bars represent standard deviation of independent triplicate experiments.

Method One:

To a 1 mL PBMCs (~3×10$^7$ cells) in a 15 mL centrifuge tube was added 2 μL mouse anti-human CDx mAb-N3'-ethyl biotin 17 conjugate (1 mg/mL in PBS), and incubated on ice for 10 min. Then, 10 mL isolation buffer was added, and centrifuged at 350×g for 5 min. 8 mL Supernatant was carefully removed and discarded by pipette, and 70 μL streptavidin M280 Dynabeads® magnetic beads (15 mg/mL) were added and incubated for 10 min at room temperature under rolling and tilting. The tube was placed on a magnet for 1 min, and supernatant was removed. Then, the tube was removed from the magnet, and added 5 mL isolation buffer and resuspended the bead-bound cells by gentle pipetting 5 times. The tube was placed on a magnet for 1 min, and supernatant was removed. The wash step was repeated twice. After three washes, 1 mL release buffer (1 mM bis-biotin in isolation buffer) was added, and incubated for 5 min at room temperature under rolling and tilting. The suspension was mixed by pipetting 10 times, and the tube was placed on a magnet for 1 min. The supernatant containing the bead-free cells was transferred to a new tube, and centrifuged at 350×g for 5 min. The supernatant was removed and discarded, and the cell pellet was suspended in 1 mL isolation buffer.

Method Two:

To a 1 mL PBMCs (~3×10$^7$ cells) in a 15 mL centrifuge tube was added 2 μL mouse anti-human CDx mAb (1 mg/mL in PBS), and incubated on ice for 10 min. Then, 10 mL isolation buffer was added, and centrifuged at 350×g for 5 min. 8 mL Supernatant was carefully removed and discarded by pipette, and 70 μL goat anti-mouse (GAM) IgG-N3'-ethyl biotin 17 conjugate coated streptavidin M280 Dynabeads® magnetic beads (prepared by incubation 10 μg GAM IgG-N3'-ethyl biotin conjugate 17 per mg of streptavidin M280 Dynabeads® magnetic beads, 15 mg/mL) was added and incubated for 10 min at room temperature under rolling and tilting. The tube was placed on a magnet for 1 min, and supernatant was removed. Then, the tube was removed from the magnet, and added 5 mL isolation buffer and resuspended the bead-bound cells by gentle pipetting 5 times. The tube was placed on a magnet for 1 min, and supernatant was removed. The wash step was repeated twice. After three washes, 1 mL release buffer (1 mM bis-biotin in isolation buffer) was added, and incubated for 5 min at room temperature under rolling and tilting. The suspension was mixed by pipetting 10 times, and the tube was placed on a magnet for 1 min. The supernatant containing the bead-free cells was transferred to a new tube, and centrifuged at 350×g for 5 min. The supernatant was removed and discarded, and the cell pellet was suspended in 1 mL isolation buffer.

General Procedure of Cell Counting and Viability Testing by Countess® Automated Cell Counter.

10 μL of cell sample and 10 μL trypan blue stain solution were mixed by pipette. 10 μL of the sample mixture was added to the chamber ports on one side of the Countess® cell counting chamber slide. Then, the Countess® cell counting chamber slide was inserted into the slide inlet on the instrument. The cell concentration and viability were simultaneously recorded by the instrument.

General Procedure of Cell Analysis by Flow Cytometry.

The cell analysis was performed using a BD® LSR II Flow Cytometry (Becton Dickinson, Franklin Lakers, NJ). The blank PBMCs were used as a control sample to set up forward angle light scatter (FSC), side angle light scatter (SSC), and photomultiplier tube (PMT) voltage to get nice population of lymphocytes, monocytes, and granulocytes. The same instrument settings were used to run the antibody labeled PBMCs, collecting 20,000 events for each sample. The AF488 signals were collected using an excitation laser at 488 nm and an emission filter at 515-545 nm. The AF647 signals were collected using an excitation laser at 633 nm and an emission filter at 650-670 nm.

Example 24: Cell Separation Based on Dual Cell Surface Markers Using Biotin and Biotin Analog with Different Binding Affinity Human peripheral T lymphocytes based on dual cell surface markers ($CD3^+$ and $CD4^+$) were chosen to demonstrate cell separation. Anti-CD4 mAb was labelled with the biotin molecule and AlexaFluor 647 (AF647) (for flow cytometry analysis purpose); and labelled anti-CD3 mAb with N3'-ethyl biotin 17 and AlexaFluor 488 (AF488). PBMCs (3×10$^7$ cells) were incubated with anti-CD4 mAb-biotin conjugate and anti-CD3 mAb-N3'-ethyl biotin 17 conjugate simultaneously on ice for 10 min. Then streptavidin M280 Dynabeads® magnetic beads were added and incubated for 10 min at room temperature. After washing step to remove unbound reagents, the magnetic labeled cells were selectively released by incubating with 1 mM bis-biotin for 5 min to yield beads-free $CD3^+CD4^-$ cells.

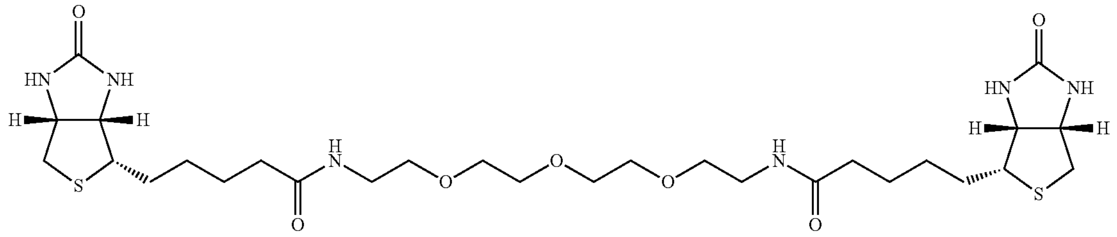

Bis-Biotin

Figure 8:
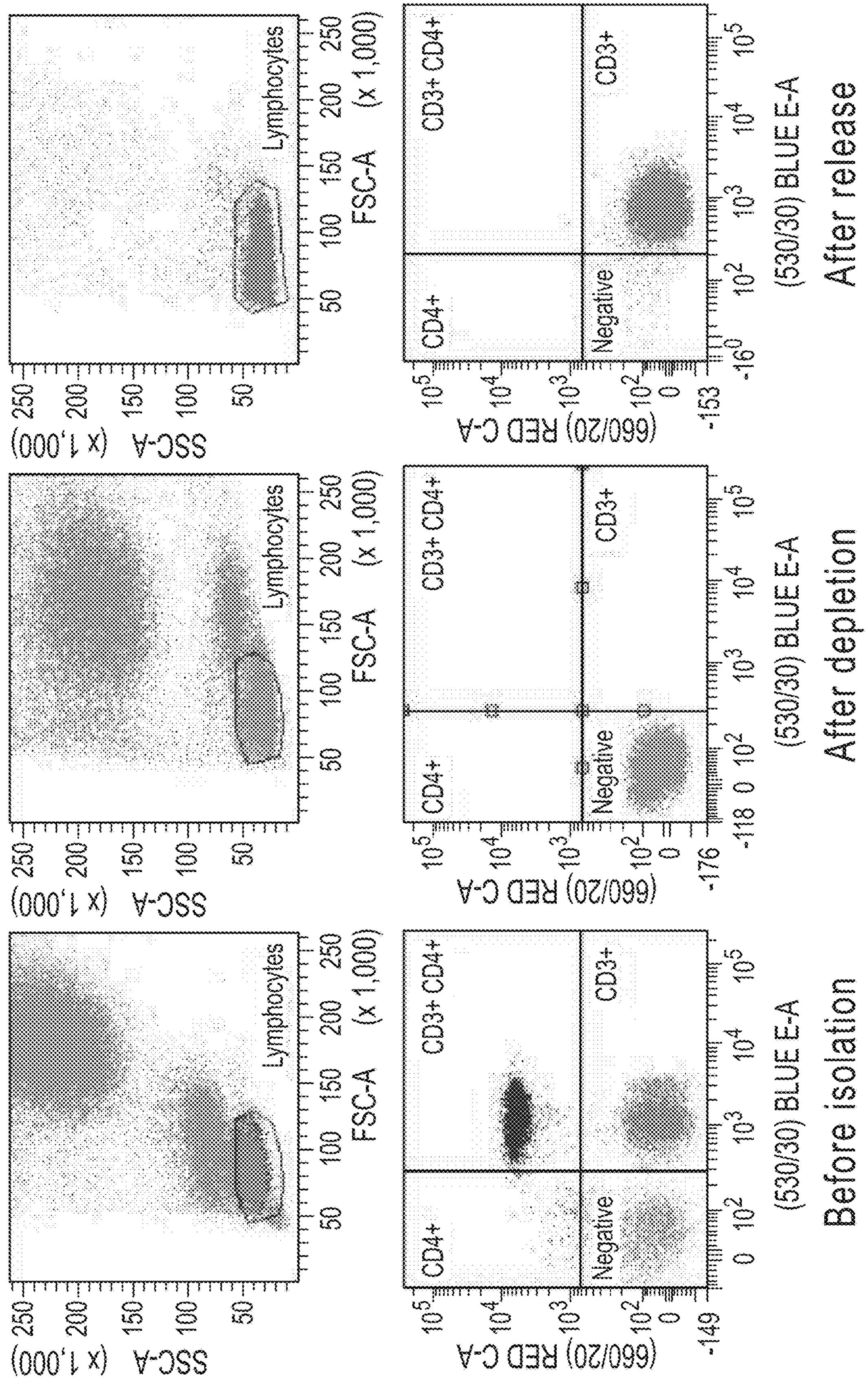
FIG. 8 shows flow histograms of cells based on dual cell surface markers (CD3 and CD4) at pre-isolation, after depletion, and after release. Population of lymphocytes, monocytes, and granulocytes shown on top. Subpopulation of lymphocytes based on CD3 and CD4 cell surface markers shown at bottom.

As shown in FIG. 8, after incubation with biotinylated anti-CD4 mAb and N3'-ethyl biotinylated anti-CD3 mAb, the cells either $CD3^+$ or $CD4^+$ have been captured by streptavidin M280 Dynabeads® magnetic beads with depletion efficiency (~100%). After incubating with 1 mM bis-biotin, $CD3^+CD4^-$ cells were selectively detached from magnetic beads with 80±5% recovery, 92±3% purity and 95±2% viability, and $CD4^+$ cells remain bound to magnetic beads. The results demonstrate that the N3'-ethyl biotin can be selectively detached from streptavidin without interfering biotin-streptavidin interactions by control of release condition. This provides a simple one-step cell selection method based on dual cell surface markers.

Although the disclosed teachings have been described with reference to various applications, methods, and compositions, it will be appreciated that various changes and modifications may be made without departing from the teachings herein. The foregoing examples are provided to better illustrate the present teachings and are not intended to limit the scope of the teachings herein. Certain aspects of the present teachings may be further understood in light of the following claims.

We claim:

1. A method of labeling a protein, comprising the steps of:

a. providing a biotin derivative of Formula (I):

(I)

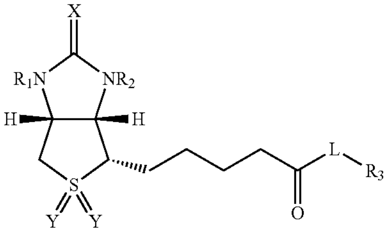

wherein:

X is O;

$R_1$ is selected from H and a derivative group;

$R_2$ is selected from H and a derivative group;

Y is absent;

L is a linker;

$R_3$ is a reactive group;

wherein $R_1$ is H and $R_2$ is a derivative group, or $R_2$ is H and $R_1$ is a derivative group;

b. providing a sample comprising a protein, the protein comprising a complementary group capable of reacting with the reactive group; and c. contacting the biotin derivative with the sample to provide a biotin derivative-labeled protein.

2. The method of claim 1, further comprising the steps of:

a. providing a biotin-binding moiety comprising a detectable moiety; and b. contacting the biotin-binding moiety with the biotin derivative-labeled protein.

3. The method of claim 2, wherein the biotin-binding moiety is an avidin or a streptavidin.

4. The method of claim 2, wherein the detectable moiety is selected from a chromophore, a fluorescent dye, a fluorescent protein, a nanocrystal, an enzyme, a molecule comprising a radioisotope, and a radioisotope.

5. The method of claim 1, wherein $R_1$ is a derivative group.

6. The method of claim 5, wherein $R_1$ comprises 1 to 3 carbon atoms.

7. The method of claim 1, wherein the linker comprises a detectable moiety.

8. The method of claim 7, wherein the detectable moiety is selected from a chromophore, a fluorescent dye, a fluorescent protein, a nanocrystal, an enzyme, and a radioisotope.

9. The method of claim 1, wherein the reactive group is an isothiocyanate, a sulfonyl chloride, a 4,6-dichlorotriazinyl, a carboxylate, a halo acetyl, a hydrazide, a succinimidyl ester, a phenol ester, a maleimide, an iodoacetamide, an azide, or an alkyne.

10. The method of claim 1, wherein L is

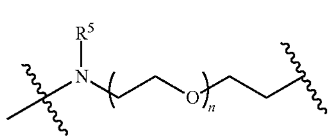

or

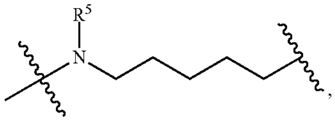

, wherein $R^5$ is H or a saturated or unsaturated straight or branched chain carbon radical having 1 to 8 carbon atoms;

each wavy line represents a point of attachment; and n is an integer from 0 to 20.

11. The method of claim 1, wherein the derivative group is a $C_1$-$C_{12}$ saturated or unsaturated straight or branched chain alkyl group.

12. The method of claim 1, wherein the biotin derivative is selected from:

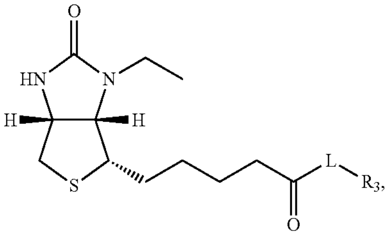
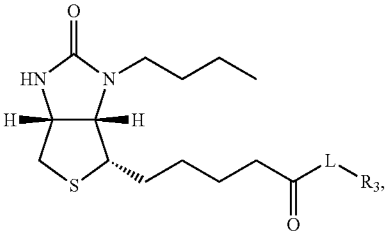
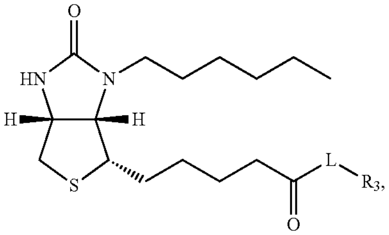
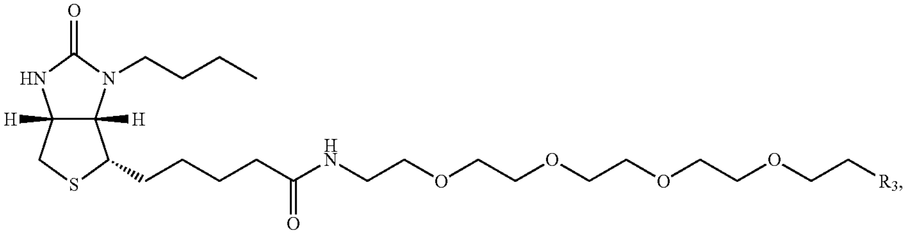
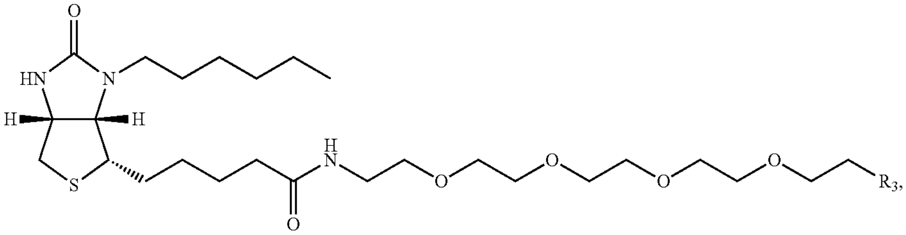
and
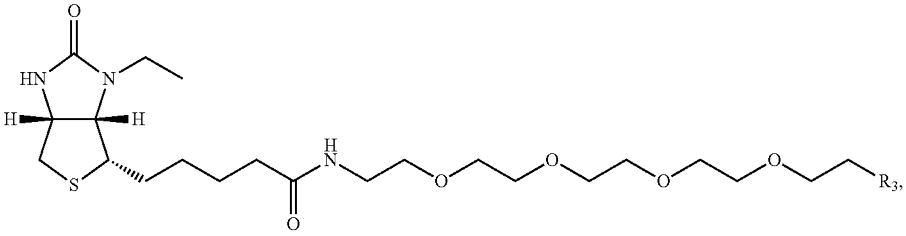
wherein L and $R_3$ are as defined in claim 1.
13. The method of claim 1, wherein the biotin derivative is selected from:
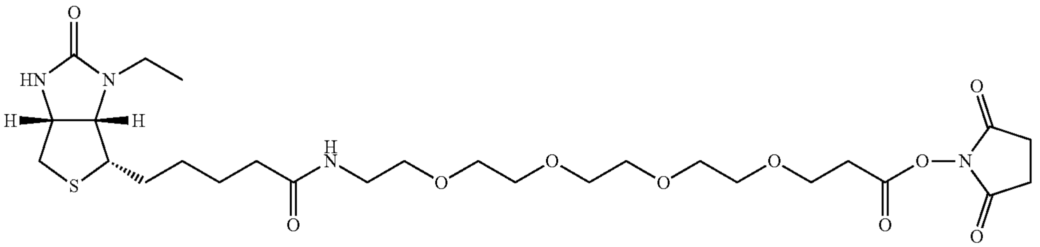
, -continued
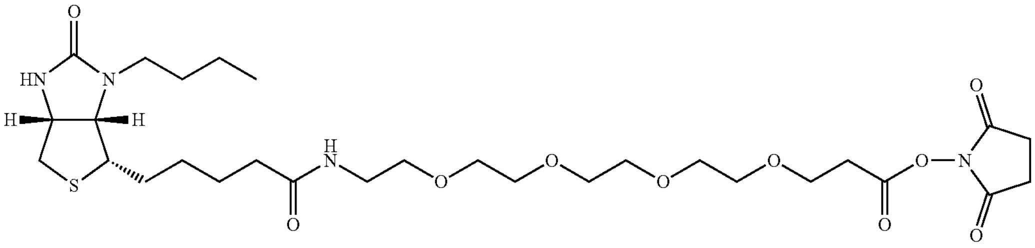
,
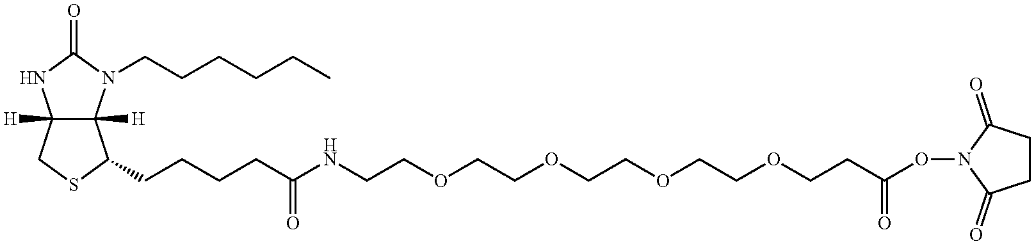
,
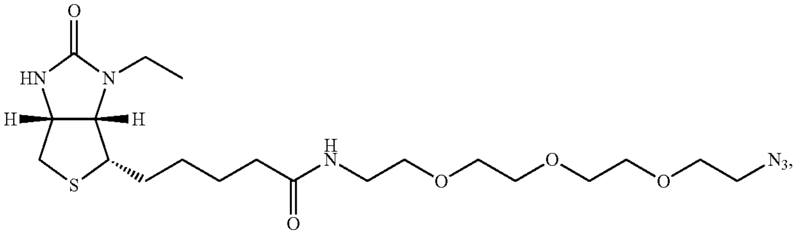
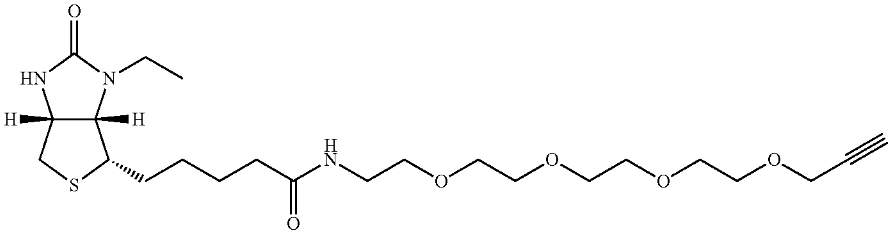
,
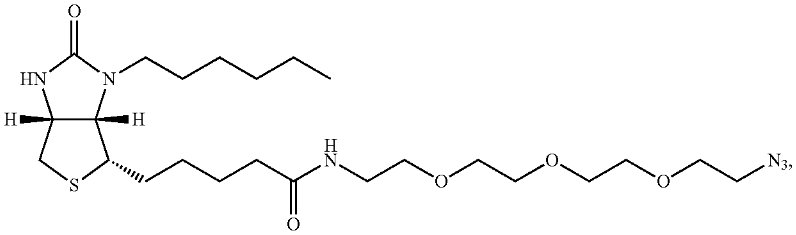
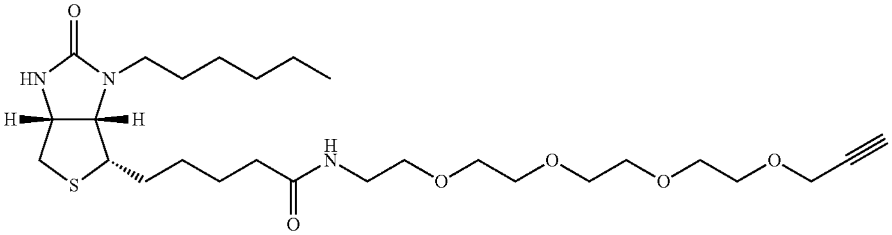
, and
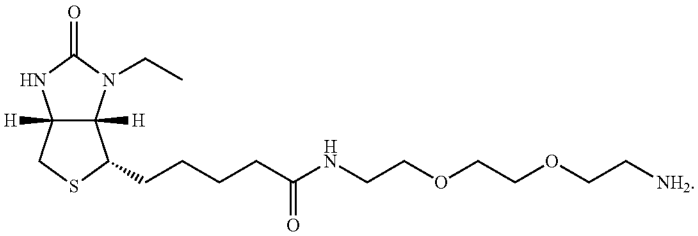

14. The method of claim 7, wherein the biotin derivative is
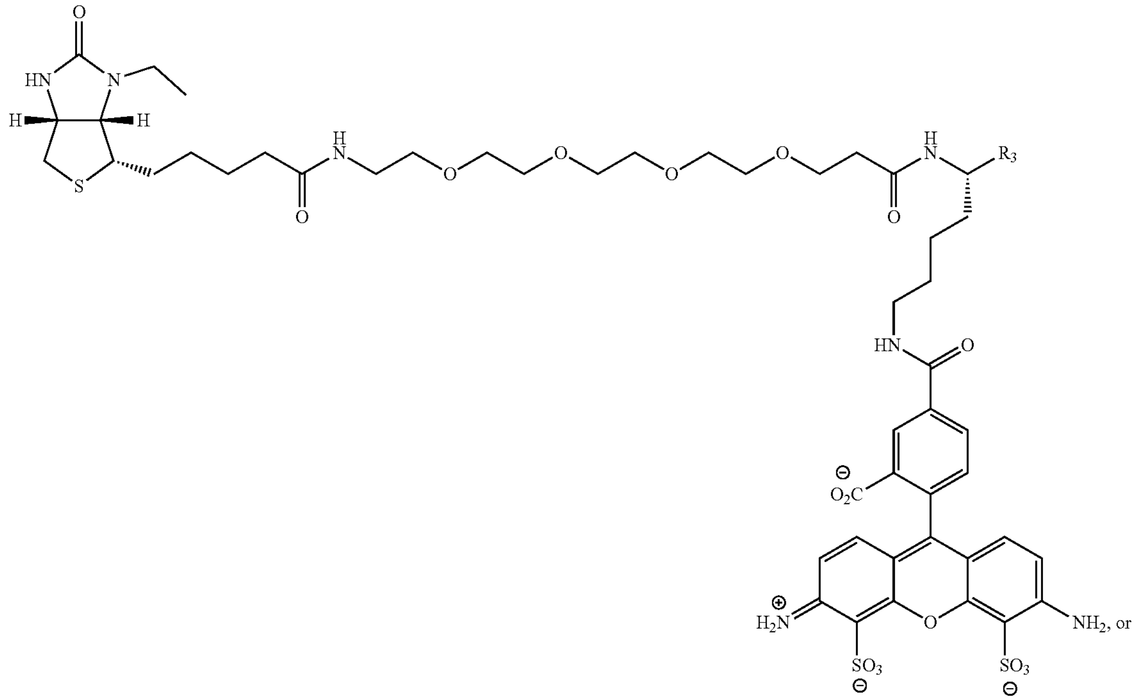
NH2, or
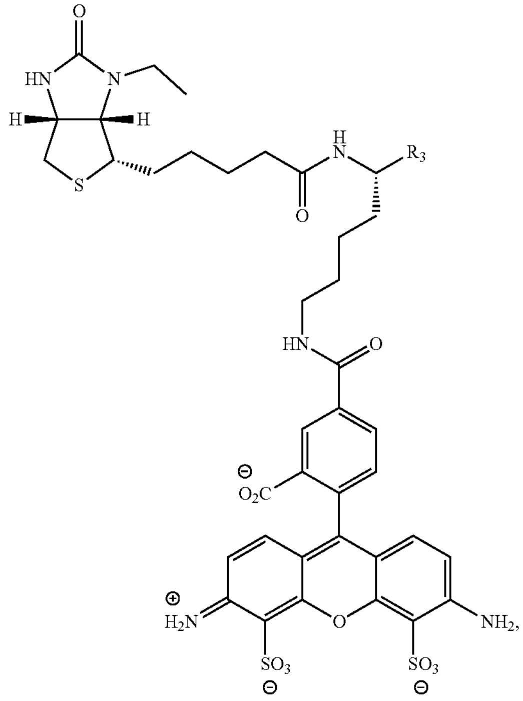
wherein $R_3$ is a reactive group.

15. The method of claim 7, wherein the biotin derivative is:
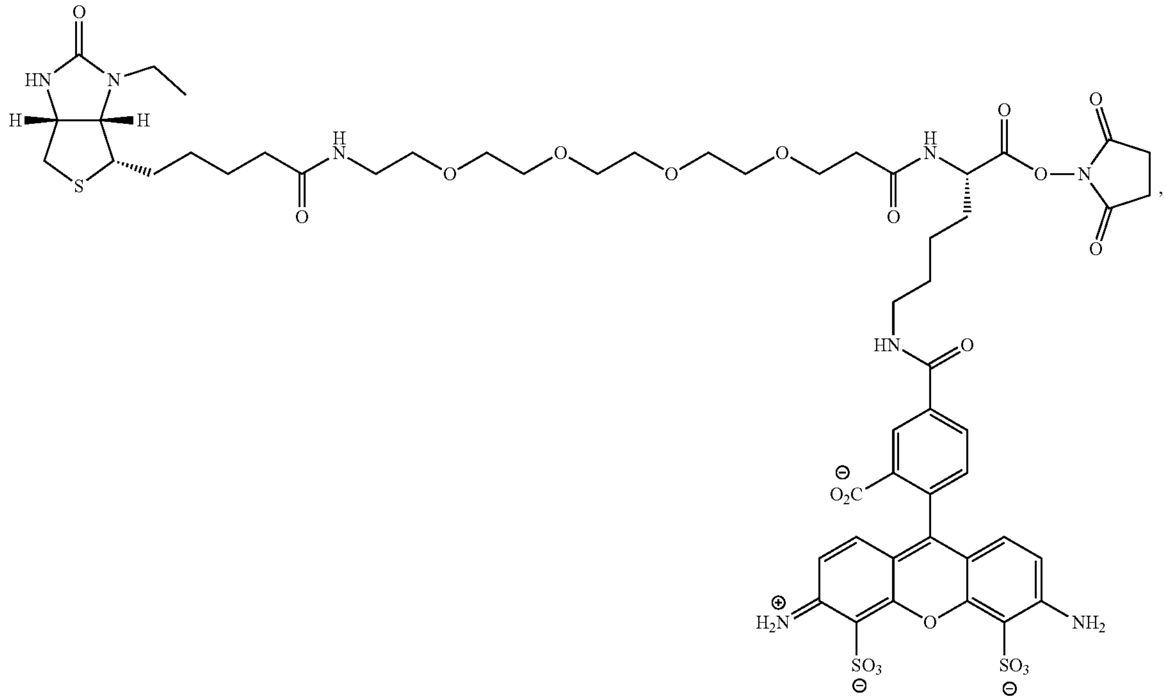
, or
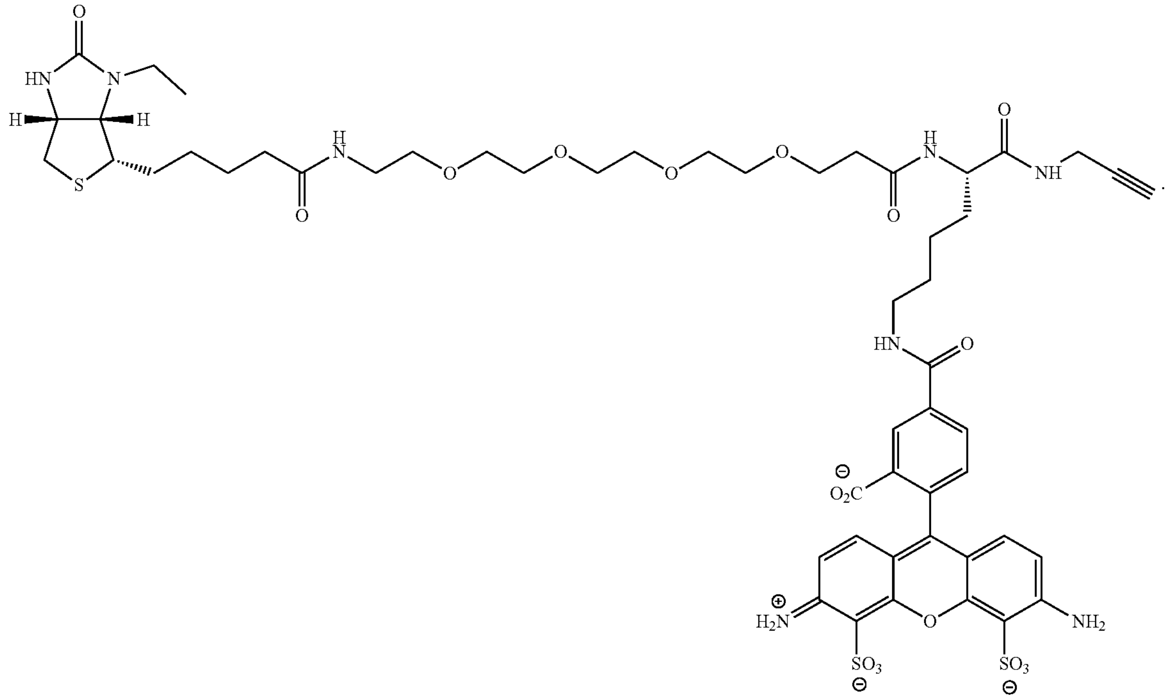
.
* * * * *